(12) United States Patent
Cai et al.

(10) Patent No.: US 8,349,867 B2
(45) Date of Patent: Jan. 8, 2013

(54) QUINOLINE COMPOUNDS, INTERMEDIATES, PREPARATION METHODS AND USES THEREOF

(75) Inventors: Zhengyan Cai, Shanghai (CN); Weicheng Zhou, Shanghai (CN); Qun Hao, Shanghai (CN)

(73) Assignee: Shanghai Institute of Pharmaceutical Industry, Shanghai (CN)

( * ) Notice: Subject to any disclaimer, the term of this patent is extended or adjusted under 35 U.S.C. 154(b) by 193 days.

(21) Appl. No.: 12/517,049

(22) PCT Filed: Dec. 6, 2007

(86) PCT No.: PCT/CN2007/003469
§ 371 (c)(1),
(2), (4) Date: May 14, 2012

(87) PCT Pub. No.: WO2008/077305
PCT Pub. Date: Jul. 3, 2008

(65) Prior Publication Data
US 2011/0046379 A1    Feb. 24, 2011

(30) Foreign Application Priority Data
Dec. 27, 2006   (CN) .......................... 2006 1 0148118

(51) Int. Cl.
*A61K 31/44*   (2006.01)
*C07D 405/06*  (2006.01)

(52) U.S. Cl. ........................................ 514/312; 546/153
(58) Field of Classification Search .................. None
See application file for complete search history.

(56) References Cited

OTHER PUBLICATIONS

Cai et al., Synthesis and HMG CoA reductase inhibition of 4-thiophenyl quinolines as potential hypocholesterolemic agents, 15(24) Bioorg. & Med. Chem. 7809-7829 (2007).*
Vippagunta et al., "Crystalline Solids", 48 Adv. Drug Delivery Rev. 3-26 (2001).*

* cited by examiner

*Primary Examiner* — Janet Andres
*Assistant Examiner* — Timothy R Rozof
(74) *Attorney, Agent, or Firm* — Birch, Stewart, Kolasch & Birch, LLP.

(57) ABSTRACT

A kind of quinoline compounds as formula A, pharmaceutical accepted solvates, optical isomers or polymorphisms thereof. The intermediates of formula D. in which, $R_1$, $R_2$ and $R_3$ is independently H, halo or the subustitents of formula H, in which, R is H, halo, $C_1$~$C_4$alkyl, $C_1$~$C_4$alkoxyl. The preparation methods and the uses for the manufacture of a medicament of inhibiting the HMG CoA reductase and treating the diseases relating to the high blood fat. Compared with the fluvastatin, rosuvatatin, pitavastatin disclosed in the prior arts, present quinoline compounds have better activity of inhibiting HMG CoA reductase. Present quinoline compounds can be used for treating the diseases relating to the high blood fat.

13 Claims, No Drawings

QUINOLINE COMPOUNDS, INTERMEDIATES, PREPARATION METHODS AND USES THEREOF

FIELD OF THE TECHNOLOGY

The present invention pertains to the art of synthesis technology in medicinal chemistry. More particularly, this invention is related to novel quinoline compounds and their intermediates, preparation methods and applications in pharmaceutical field.

BACKGROUND

Hypocholesterolemic agents have evolved rapidly when hypercholesterolemia is well recognized as a primary risk factor in atherosclerotic diseases and coronary heart diseases. A class of drugs, such as 3-hydroxy-3-methylglutaryl CoA reductase (HMG CoA reductase) inhibitors, the statins, are currently potent hypocholesterolemic agents. (Cai Z-Y, Zhou W—C. Progresses in researches of HMG CoA reductase inhibitors, *Chinese Journal of New Drugs*, 2006, 15 (22): 1907-1911). The launched drugs, lovastatin, simvastatin, pravastatin, fluvastatin, atorvastatin, rosuvastatin, and pitavastatin are currently available hypocholesterolemic agents. However, as far as human requirement is concerned, there is a need to develop new potent hypocholesterolemic drugs.

The structure of the fully synthetic statins is characterized by desmethylmevalonic acid or the lactone, the pharmacophore which is connected to a lipophilic ring, such as hexahydronaphthalene, indole, pyrrole, pyrimidine, or quinoline. Systematical QSAR study on quinoline statin compounds, such as pitavastatin, show desmethylmevalonic acid linked through a trans-ethylene group to position 3 in quinoline exhibited good activity in inhibiting HMG CoA reductase. The introduction of chloro, methyl or methoxy etc. to the 6-, 7- or 8-position of the quinoline nucleus may increase the inhibitory potency. (Cai Z-Y, Zhou W-C. Progresses in researches of HMG CoA reductase inhibitors, *Chinese Journal of New Drugs*, 2006, 15 (22): 1907-1911). So far in the known quinolines as HMG CoA inhibitors, the aryl group such as 4-fluorophenyl, is directly linked to position 4 in quinoline, the derivatives from 4-thiohenyl have not been reported.

DETAILED DESCRIPTION OF THE INVENTION

An object of the present invention is directed to a novel quinoline compound of the formula A, and its pharmaceutically acceptable solvate, stereoisomers or polymorphism that provide the HMG CoA reductase inhibition activities and that can be used as hypocholesterolemic agents.

The quinoline compound of the formula A in this present invention is designed with pitavastatin as a leading compound. The pharmacophore moiety, desmethylmevalonic lactone, is connected to position 3 in the quinoline nucleus, and the nucleus is flanked at position 4 by substituted thiophenyl as a lipophilic group, and at position 6, 7, 8 by different group, such as substituted thiophenyl or halogen.

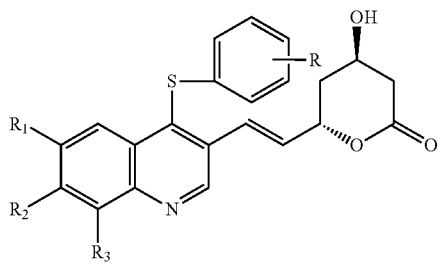

A

Wherein
$R_1$, $R_2$ and $R_3$ are each independently selected from the group consisting of hydrogen, halogen, the group shown in formula H,

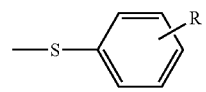

H

Wherein
R is selected from the group consisting of hydrogen, halogen, C1~4 alkyl or C1~4 alkoxy.

The halogen in this invention is selected from the elements consisting of F, Cl, Br or I, and more preferred element is F or Cl. R is selected from the group consisting of methyl, ethyl, propyl, isopropyl, cyclopropyl, methoxy, ethoxy, propoxy or isopropoxy.

In another preferred embodiment, the quinoline compound in this invention may be selected from the following:

(4R,6S)-6-[(E)-2-(6,7,8-trifluoro-4-(4-isopropylthiophenyl) quinoline-3-yl)-ethenyl]-3,4,5,6-tetrahydro-4-hydroxy-2H-pyran-2-one;

(4R,6S)-6-[(E)-2-(6-fluoro-4,7-di-(3-methoxythiophenyl) quinoline-3-yl)-ethenyl]-3,4,5,6-tetrahydro-4-hydroxy-2H-pyran-2-one;

(4R,6S)-6-[(E)-2-(4, 6,7,8-tetra-(3-methoxythiophenyl) quinoline-3-yl)-ethenyl]-3,4,5,6-tetrahydro-4-hydroxy-2H-pyran-2-one;

(4R,6S)-6-[(E)-2-(6-fluoro-4,7-di-(thiophenyl)quinoline-3-yl)-ethenyl]-3,4,5,6-tetrahydro-4-hydroxy-2H-pyran-2-one;

(4R,6S)-6-[(E)-2-(6,7,8-trifluoro-4-(4-fluorothiophenyl) quinoline-3-yl)-ethenyl]-3,4,5,6-tetrahydro-4-hydroxy-2H-pyran-2-one;

(4R,6S)-6-[(E)-2-(7-chloro-6-fluoro-4-(3-methoxythiophenyl)quinoline-3-yl)-ethenyl]-3,4,5,6-tetrahydro-4-hydroxy-2H-pyran-2-one;

(4R,6S)-6-[(E)-2-(6-fluoro-4,7-di-(4-isopropylthiophenyl) quinoline-3-yl)-ethenyl]-3,4,5,6-tetrahydro-4-hydroxy-2H-pyran-2-one;

(4R,6S)-6-[(E)-2-(6,7,8-trifluoro-4-thiophenylquinoline-3-yl)-ethenyl]-3,4,5,6-tetrahydro-4-hydroxy-2H-pyran-2-one;

(4R,6S)-6-[(E)-2-(6-fluoro-4,7,8-tri-(4-fluorothiophenyl) quinoline-3-yl)-ethenyl]-3,4,5,6-tetrahydro-4-hydroxy-2H-pyran-2-one Or (4R,6S)-6-[(E)-2-(4-(4-isopropylthiophenyl)quinoline-3-yl)-ethenyl]-3,4,5,6-tetrahydro-4-hydroxy-2H-pyran-2-one.

The pharmaceutically acceptable solvate in this invention is the hydrate, and solvate with C1~4 alcohol or other organic solvents.

Another object of the present invention is directed to the intermediate of the formula D.

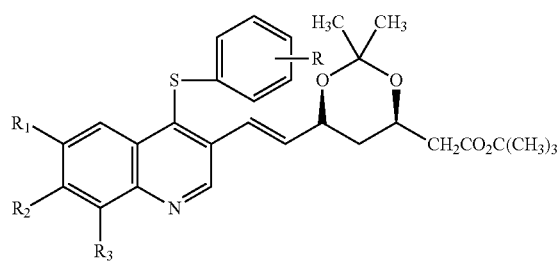

D

Wherein
$R_1$, $R_2$ and $R_3$ are each independently selected from the group consisting of hydrogen, halogen, the group shown in formula H,

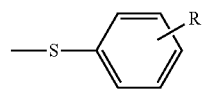

H

Wherein
R is selected from the group consisting of hydrogen, halogen, C1~4 alkyl or C1~4 alkoxy.

The halogen in this invention is selected from the element consisting of F, Cl, Br or I, and more preferred element is F or Cl. R is selected from the group consisting of methyl, ethyl, propyl, isopropyl, cyclopropyl, methoxy, ethoxy, propoxy or isopropoxy.

A further object of the present invention is directed to the preparation of intermediate of the formula D, which is comprising that compound B is reacted with compound C, tert-butyl (3R,5S)-6-oxo-3,5-dihydroxy-3,5-O-isopropylidene-hexanoate, by Wittig-Horner reaction under basic condition in organic solvent.

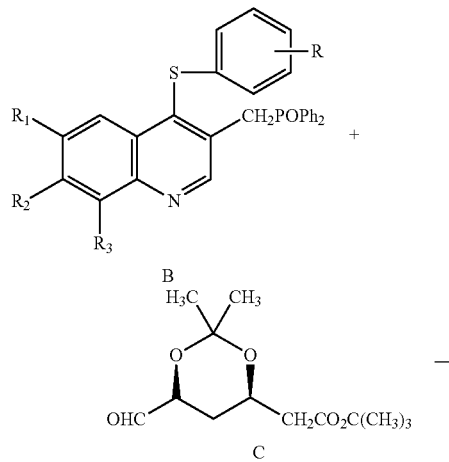

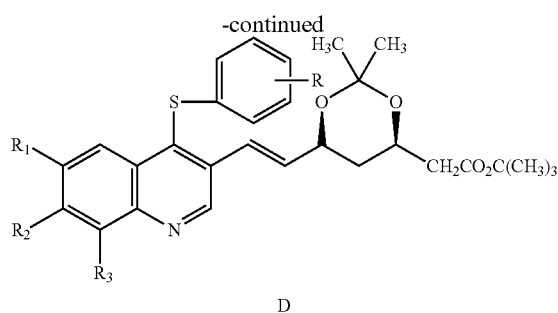

D

Wherein
$R_1$, $R_2$ and $R_3$ are each independently selected from the group consisting of hydrogen, halogen, the group shown in formula H,

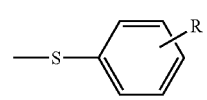

H

Wherein
R is selected from the group consisting of hydrogen, halogen, C1~4 alkyl or C1~4 alkoxy.

The compound Bis prepared by the method shown in below:

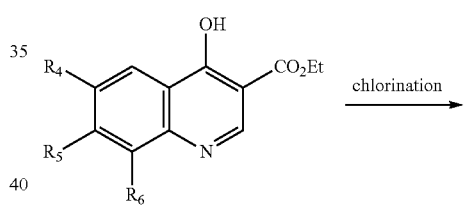

chlorination

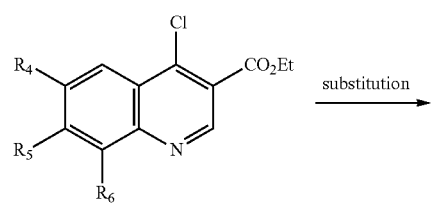

substitution

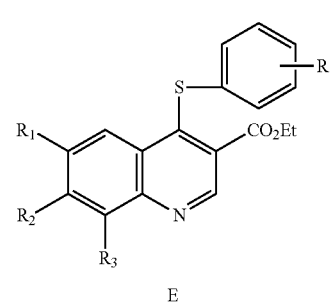

E

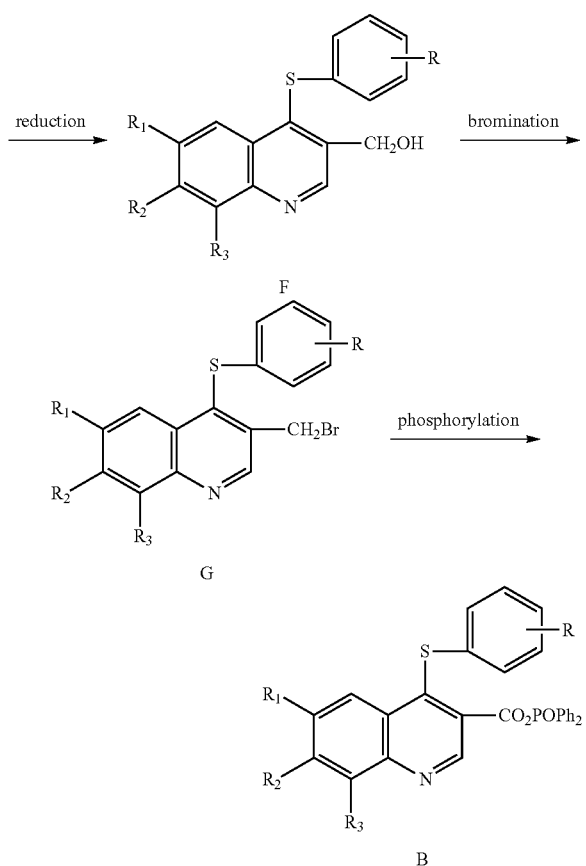

Wherein $R_1$, $R_2$, $R_3$ and R are defined as the above. $R_4$, $R_5$ and $R_6$ are each independently selected from the group consisting of hydrogen or halogen.

The novel quinoline compound A is synthesized in optically pure forms by the general method as follows:

1. Chlorination and Aromatic Nucleophilic Substitution

The monosubstituted or multisubstituted compounds of formula E are prepared with ethyl 4-hydroxy-6,7,8-trisubstituted-quinoline-3-carboxylates as the starting materials by chlorination with $POCl_3$ and aromatic nucleophilic substitution under basic condition. The solvent in aromatic nucleophilic substitution is THF, EtOAc, toluene, DMF, or DMSO etc. The nucleophiles are the corresponding thiophenols. The base used in the reaction is selected from $Et_3N$, pyridine, $Na_2CO_3$, $K_2CO_3$, NaOH, NaH, and n-BuLi etc. The temperature of reaction is −30° C.~150° C. The 4-monosubstituted, 4,7-disubstituted, 4,7,8-trisubstituted or 4,6,7,8-tetrasubstituted compound of formula E is highly regiospecifically prepared under different condition, such as different substrate, different mol ratio of substrate and nucleophilic agents, base, solvent and reaction temperature. Characterizations of compounds E are shown in Tables 31-40.

2. Reduction

Compound F is prepared from compound E by reducing agents via reduction under organic solvent. The organic solvent is selected from benzene, toluene, THF, methanol, ethanol etc. The organic solvent is also selected from the mixture of two solvents mentioned above. The reducing agent is selected from diisobutylaluminum hydride (DIBAL-H), $KBH_4/ZnCl_2$, $LiAlH_4$, $LiAlH_4/LiCl$, $NaBH_4$, $NaBH_4/LiCl$ etc. The preferred organic solvent is toluene. The optimal reducing agent is diisobutylaluminum hydride (DIBAL-H). The optimal reaction temperature is 0° C.~20° C. Characterizations of compounds F are shown in Tables 41-50.

3. Bromination:

Bromination of the compound F with $PBr_3$ affords the bromide G. The solvent for the reaction is selected from THF, t-BuOMe, $CH_2Cl_2$, $CHCl_3$, toluene etc, and the optimal solvent is $CH_2Cl_2$. The reaction temperature is 0° C.~100° C., and the optimal reaction temperature is 0° C.~30° C.

4. Phosphorylation:

The compound G is converted to the corresponding phosphorus compound B with $Ph_2POEt$. The solvent is selected from THF, t-BuOMe, $CH_2Cl_2$, $CHCl_3$, toluene etc, and the preferred solvent is toluene. The reaction temperature is 20☐~150☐, and the optimal reaction temperature is 100° C.~120° C. Characterizations of compound G and B are shown in Tables 51~60.

Wittig-Hornor reaction in this invention is the widely-known technology. The details of the Wittig-Hornor reaction in this invention are as follows: compound B is reacted with compound C, tert-butyl (3R,5S)-6-oxo-3,5-dihydroxy-3,5-O-isopropylidene-hexanoate under basic condition in organic solvent.

The solvent is selected from THF, $Et_2O$, t-BuOMe, toluene etc., and the optimal solvent is THF. The alkaline is selected from lithium 2,2,6,6-tetramethylpiperidine, lithium diisopropylamide, lithium bis(trimethylsilyl)amide, lithium n-butyl, NaH etc, and the optimal alkaline is lithium 2,2,6,6-tetramethylpiperidine.

The preferred conditions for the Wittig-Hornor reaction is that the optimal reaction temperature is −100° C.~50° C., and preferably between −78° C. and 25° C. The optimal reaction time was 20~48 hours. The mol ratio of compound B, compound C and alkaline is 1:1:1~1:2:4, and more preferred is 1:1.2:1.5. Characterizations of compound D are shown in Tables 1~10.

Another object of the present invention is directed to the preparation of quinoline compound. The compound D is deprotected and lactonized with acid in solvent to give the target compounds A. The acid is selected from $CH_3COOH$, $CF_3COOH$ or HCl, and more preferred is $CF_3COOH$. The volume percentage of the acid in solvent is 5~40%, and more preferred is 20%. The optimal reaction temperature is 0° C.~80° C., and more preferred is 25° C. The optimal reaction time is 1~8 hours. The solvent is selected from one or more of THF, t-BuOMe, $CH_2Cl_2$, $CHCl_3$, toluene etc., and more preferred is $CH_2Cl_2$. Characterizations of compound D are shown in Tables 11~30.

Yet another object of the present invention is directed to the quinoline compound, and its pharmaceutically acceptable solvate, stereoisomers or polymorphism which is prepared for inhibition of HMG CoA reductase and useful in the treatment of the hypercholesterolemic.

The present invention provides pharmaceutical compositions which comprise quinoline compound A and any other pharmaceutically acceptable carriers. The carriers include conventional drug carries in the pharmaceutical art, for instance, diluents or excipients such as water; binders such as cellulose derivatives, gelatin or polyvinylpyrrolidone, etc; fillers such as starch; disintegrants such as calcium carbonate or sodium bicarbonate. Additionally, other excipients such as essence and/or sweetener can be included.

A variety of dosage forms can be prepared with the pharmaceutical compositions comprising quinoline compound A of the invention as active ingredients by conventional methods in the medical field. The solid dosage forms such as tablets, powders or capsules can be prepared for oral usage. The injection is prepared for injection usage. The content of the compound A of the present invention in the formulation is 0.1%~99.9% (w/w), and more preferred is 0.5~90% (w/w).

The dosage forms comprising quinoline compound A of the invention as active ingredients may be prepared for intravenous injection, subcutaneous injection or oral usage, which can be administered to patients who need such therapy. The conventional dose is 1~100 mg/kg/day, according to the disease and patients' age.

The advantages of this invention are that: as compared with the drugs known in the art, such as fluvastatin, rosuvastatin or pitavastatin, the quinoline compound A of the present invention is provided with more potent in inhibiting HMG CoA reductase which can be used to treat the related disease of hypercholesterolemic.

EMBODIMENTS OF THE INVENTION

Other features of the invention will become apparent in the course of the following description of exemplary embodiments which are given for illustration of this invention and are not intended to be limiting thereof.

Preparation Example 1

Ethyl 4-chloro-6,7,8-trifluoroquinoline 3-carboxylate

A solution of ethyl 4-hydroxy-6,7,8-trifluoroquinoline-3-carboxylate (59.0 g) and POCl$_3$ (500 ml) was refluxed for 8 h. Excess POCl$_3$ was distilled off, the residue was removed into the mixture of ice and water. Solid NaHCO$_3$ was added into the mixture to pH 7~8 and the precipitated solid was isolated by filtration. The crude was recrystallized by toluene to afford the title compound (41.3 g, 65.6% yield), mp: 110-112° C. ethyl 4-chloro-quinoline-3-carboxylate, ethyl 6-fluoro-4,7-dichloroquinoline-3-carboxylate, and ethyl 4,7-dichloro-quinoline-3-carboxylate, were prepared in the manner analogous to the method described above, when ethyl 4-hydroxy-quinoline-3-carboxylate, ethyl 4-hydroxy-6-fluoro-7-chloro-quinoline-3-carboxylate, and ethyl 4-hydroxy-7-chloro-quinoline-3-carboxylate were used as the starting material respectively.

Preparation Example 2

Ethyl 4-substituted thiophenyl-quinoline-3-carboxylate (E1~4)

A mixture of ethyl 4-chloro-quinoline-3-carboxylate (8.0 g, 34 mmol), 4-fluoro thiophenol (5.2 g, 41 mmol) and triethylamine (6.9 g, 68 mmol) in THF (80 mL) was stirred at room temperature for 30 min. The insoluble material was filtered off. The filtrate was concentrated, and the residue was recrystallized with toluene/petroleum ether to afford ethyl 4-(4-fluoro-thiophenyl-quinoline-3-carboxylate (10.0 g, E2). Ethyl 4-thiophenyl-quinoline-3-carboxylate (E1), ethyl 4-(3-methoxy-thiophenyl-quinoline-3-carboxylate (E3), and ethyl 4-(4-isopropyl-thiophenyl-quinoline-3-carboxylate (E4), were prepared in the manner analogous to the method described above, when 4-fluoro-thiophenol was replaced with thiophenol, 3-methoxy-thiophenol, and 4-isopropyl-thiophenol respectively. The data of yield, melting points (Mp.) and $^1$H-NMR spectra of compound E1-4 was shown in Table 1.

Preparation Example 3

Ethyl 7-chloro-4-substituted thiophenyl-quinoline-3-carboxylate (E5~8)

Compounds of E5~8 were prepared in the manner analogous to the method of Preparation example 2, when ethyl 4,7-dichloro-quinoline-3-carboxylate was reacted with thiophenol, 4-fluoro-thiophenol, 3-methoxy-thiophenol, and 4-isopropyl-thiophenol respectively. The data of yield, melting points (Mp.) and $^1$H-NMR spectra of compound E5-8 was shown in Table 2.

Preparation Example 4

Ethyl 6-fluoro-7-chloro-4-substituted thiophenyl-quinoline-3-carboxylate (E9~12)

Compounds of E9~12 were prepared in the manner analogous to the method of Preparation example 2, when ethyl 6-fluoro-4,7-dichloro-quinoline-3-carboxylate was reacted with thiophenol, 4-fluoro-thiophenol, 3-methoxy-thiophenol, and 4-isopropyl-thiophenol respectively. The data of yield, melting points (Mp.) and $^1$H-NMR spectra of compound E9~12 was shown in Table 3.

Preparation Example 5

Ethyl 6,7,8-trifluoro-4-substituted thiophenyl-quinoline-3-carboxylate (E13~16)

A solution of triethylamine (0.9 g, 8.6 mmol) in THF (60 ml) was dropped into a mixture of ethyl 4-chloro-6,7,8-trifluoro-quinoline-3-carboxylate (5.0 g, 17.3 mmol), and 4-fluoro-thiophenol (2.2 g, 17.3 mmol) in THF (50 ml) at −15° C. The mixture was stirred for 1 h at this temperature before quenching with water and ethyl acetate. The organic layer was separated, washed with brine, dried over Na$_2$SO$_4$, and concentrated. The residue was purified by flash chromatography (silica gel, petroleum ether-EtOAc, 10:1) to provide the title compound as a yellow solid, E14, (4.0 g, 60.0%). mp: 126-8° C.

Compounds E13, E15, and E16 were prepared in the manner similar to the method described above, when 4-fluoro-thiophenol was replaced with thiophenol, 3-methoxy-thiophenol, and 4-isopropyl-thiophenol respectively. The data of yield, melting points (Mp.) and $^1$H-NMR spectra of compound E13~16 was shown in Table 4.

Preparation Example 6

Ethyl 4,7-disubstituted-thiophenyl-quinoline-3-carboxylate (E17~20)

3-Methoxythiophenol (10.8 g, 77 mmol) was added to a mixture of NaH (60%, 3.0 g, 75 mmol) in DMF (30 ml) at 0° C. The resulting mixture was stirred at 0° C. for 0.5 h and then 4,7-dichloro-quinoline-3-carboxylate (7.0 g, 25.9 mmol) was added. The mixture was stirred at 60° C. for 0.5 h. The reaction mixture was transferred to a separatory funnel. Ethyl acetate and water were added. The organic layer was separated, washed with brine, dried over Na$_2$SO$_4$, and concentrated. The resulting oil was purified by silica gel chromatography (petroleum ether-EtOAc, 6:1) to provide the title compound, E19, (10.9 g, 88.1%) as an oil.

Compounds E17, E18, and E20 were prepared in the manner similar to the method described above, when 3-methoxythiophenol was replaced with thiophenol, 4-fluoro-thiophenol, and 4-isopropyl-thiophenol respectively. The data of yield, melting points (Mp.) and $^1$H-NMR spectra of compound E17~20 were shown in Table 5.

Preparation Example 7

Ethyl 6-fluoro 4,7-disubstituted-thiophenyl-quinoline-3-carboxylate (E21~24)

A mixture of ethyl 6-fluoro 4,7-dichloro-quinoline-3-carboxylate (6.0 g, 20.8 mmol), 3-methoxy-thiophenol (5.8 g, 41.6 mmol) in DMF (20 ml) was stirred at room temperature for 0.5 hour and then cooled to 0° C. Anhydrous $K_2CO_3$ (20.0 g, 145 mmol) was added into the mixture and stirred for 1 hour below 10° C. The solid was isolated by filtration and washed with EtOAc. The filtrate was transferred to a separatory funnel, and ethyl acetate and water were added. The organic layer was separated, washed with brine, dried over $Na_2SO_4$, and concentrated. The resulting oil was purified by silica gel chromatography (petroleum ether-EtOAc, 6:1) to provide the title compound, E23, (6.2 g, 60.0%) as oil.

Compounds E21, E22, and E24 were prepared in the manner analogous to the method described above, when 3-methoxy-thiophenol was replaced with thiophenol, 4-fluoro-thiophenol, and 4-isopropyl-thiophenol respectively. The data of yield, melting points (Mp.) and $^1$H-NMR spectra of compound E21~24 were shown in Table 6.

Preparation Example 8

Ethyl 6,8-difluoro-4,7-disubstituted-thiophenyl-quinoline-3-carboxylate (E25~28)

About 7.7 ml $Et_3N$ was added to a solution of ethyl 6,7,8-trifluoro-4-chloro-quinoline-3-carboxylate (8.0 g, 27.4 mmol) and 4-isopropylthiophenol (8.4 g, 55 mmol) in THF (80 ml) at room temperature and stirred for 1 hour. The insoluble materials were filtered off, and the filtrate was evaporated in vacuum to give the crude product. Recrystallization from petroleum ether gave the compound, E28, as a yellow solid (7.4 g, 50.0%), mp: 75-77° C.

Compounds E25, E26, and E27 were prepared in the manner analogous to the method described above, when 4-isopropyl-thiophenol was replaced with thiophenol, 4-fluoro-thiophenol, and 3-methoxy-thiophenol respectively. The data of yield, melting points (Mp.) and $^1$H-NMR spectra of compound E25~28 were shown in Table 7.

Preparation Example 9

Ethyl 4,6,7-trisubstituted-thiophenyl-quinoline-3-carboxylate (E29~32)

Ethyl 6-fluoro-4,7-dichloro-quinoline-3-carboxylate (7.1 g, 27.4 mmol) and 4-isopropyl-thiophenol (13.7 g, 90.1 mmol) were suspended in DMF (80 ml). The mixture was heated to 60° C. and stirred until the material was dissolved. Cooled to 25° C. and added to anhydrous $K_2CO_3$ (37.8 g, 274 mmol), the mixture was stirred for 1 h at 25° C. The insoluble materials were filtered off, and the filtrate was transferred to a separatory funnel, and ethyl acetate and water were added. The organic layer was separated, washed with brine, dried over $Na_2SO_4$, and concentrated to dryness. The resulting oil was purified by silica gel chromatography (petroleum ether-EtOAc, 6:1) to provide the compound, E32, (14.9 g, 83.5%) as oil.

Compounds E29, E30, and E31 were prepared in the manner analogous to the method described above, when 4-isopropylthiophenol was replaced with thiophenol, 4-fluoro-thiophenol, and 3-methoxy-thiophenol respectively. The data of yield, melting points (Mp.) and $^1$H-NMR spectra of compound E29~32 were shown in Table 8.

Preparation Example 10

Ethyl 6-fluoro-4,7,8-trisubstituted-thiophenyl-quinoline-3-carboxylate (E33~36)

Anhydrous $K_2CO_3$ (37.8 g, 274 mmol) was added to a mixture of ethyl 6,7,8-trifluoro-4-chloro-quinoline-3-carboxylate (8.0 g, 27.4 mmol) and 4-isopropyl-thiophenol (13.7 g, 90.1 mmol) in DMF (80 ml) at 25° C. and stirred for 1 h. The insoluble materials were filtered off, and the filtrate was transferred to a separatory funnel, and ethyl acetate and water were added. The organic layer was separated, washed with brine, dried over $Na_2SO_4$, and concentrated to dryness. The resulting oil was purified by silica gel chromatography (petroleum ether-EtOAc, 6:1) to provide the compound, E36, (13.0 g, 65.8%) as oil.

Compounds E33, E34, and E35 were prepared in the manner analogous to the method described above, when 4-isopropylthiophenol was replaced with thiophenol, 4-fluoro-thiophenol, and 3-methoxy-thiophenol respectively. The data of yield, melting points (Mp.) and $^1$H-NMR spectra of compound E33~36 were shown in Table 9.

Preparation Example 11

Ethyl 4,6,7,8-tetrasubstituted-thiophenyl-quinoline-3-carboxylate (E37~40)

A mixture of ethyl 6,7,8-trifluoro-4-chloro-quinoline-3-carboxylate (8.0 g, 27.4 mmol), 4-isopropyl-thiophenol (18.7 g, 123.3 mmol), anhydrous $K_2CO_3$ (37.8 g, 274 mmol) in DMF (80 ml) was stirred at 60° C. for 1 hour. The insoluble materials were filtered off, and the filtrate was transferred to a separatory funnel and ethyl acetate and water were added. The organic layer was separated, washed with brine, dried over $Na_2SO_4$, and concentrated to dryness. The resulting oil was purified by silica gel chromatography (petroleum ether-EtOAc, 6:1) to provide the title compound, E40, (19.4 g, 84.3%) as oil.

Compounds E37, E38, and E39 were prepared in the manner analogous to the method described above, when 4-isopropylthiophenol was replaced with thiophenol, 4-fluoro-thiophenol, and 3-methoxy-thiophenol respectively. The data of yield, melting points (Mp.) and $^1$H-NMR spectra of compound E37~40 was shown in Table 10.

Preparation Example 12

4-Thiophenyl-quinoline-3-methanol (F1)

A suspension of $LiAlH_4$ (1.0 g, 29.4 mmol) and anhydrous LiCl (1.2 g, 29.4 mmol) in anhydrous THF (30 ml) was stirred for 0.5 h under an atmosphere of nitrogen at 00° C. The solution of E1 (3.2 g, 9.8 mmol) in anhydrous THF (10 ml) was added into the resulting suspension at 0° C. and stirred for 2 h before adding $Na_2SO_4.10H_2O$ slowly. The insolubable material was filtered. The filtrate was concentrated, and the residue was purified by silica gel chromatography (petroleum ether-EtOAc, 2:1) to provide the title compound (0.28 g, 10%).

Preparation Example 13

4-(4-Fluoro-thiophenyl) quinoline-3-methanol (F2)

A mixture of anhydrous $ZnCl_2$ (2.9 g, 21.4 mmol) and $KBH_4$ (2.3 g, 42.8 mmol) in THF (15 ml) was stirred at room temperature for 2 h. A solution of E2 (3.5 g, 10.7 mmol) in toluene (75 ml) was added and refluxed (95° C.) overnight. The reaction mixture was cooled to room temperature, the insoluble was filtered off, and the filter cake was washed with hot toluene. All the toluene was combined and washed with water, 0.1 mol/L NaOH, brine, dried over $Na_2SO_4$, and concentrated to dryness. The resulting oil was purified by silica gel chromatography (petroleum ether-EtOAc, 1:1) to provide the title compound F2 (0.3 g, 9.8%).

Preparation Example 14

4-(3-methoxy-thiophenyl)quinoline-3-methanol (F2)

$NaBH_4$ (1.2 g, 31.7 mmol) was added into a solution of E3 (5.0 g, 15.3 mmol) in EtOH (100 ml) at room temperature and stirred for 8 h. The insoluble material was filtered and the filtrate was concentrated to dryness. The residue was purified by silica gel chromatography (petroleum ether-EtOAc, 1:1.5) to provide the title compound F3 (1.3 g, 30%).

Preparation Example 15

7-Chloro-4-(4-fluoro-thiophenyl)quinoline-3-methanol (F6)

Anhydrous LiCl (0.14 g, 3.3 mmol) was added into a solution of E6 (1.0 g, 2.6 mmol) in EtOH (15 ml) and stirred for 5 min. at 0° C. $NaBH_4$ (0.13 g, 3.4 mmol) was added into the resulting mixture and stirred for 0.5 h at 0° C. The reaction mixture was stirred for 18 h at room temperature before concentration to dryness. Water and EtOAc was added to the residue and the organic layer was separated, washed with brine, dried over $Na_2SO_4$ and concentrated. The residue was purified by silica gel chromatography (petroleum ether-EtOAc, 1:1) to provide the title compound F6 (0.27 g, 30%).

Preparation Example 16

6,7,8-trifluoro-4-thiophenyl-quinoline-3-methanol (F13)

About 22 ml (55 mmol) of a 2.5 mol/L DIBAL-H in toluene was added to a solution of E13 (8.0 g, 21.9 mmol) in anhydrous toluene (80 ml) at 0° C. under an atmosphere of nitrogen. The resulting solution was stirred for 2 h at 00° C. before quenching with 6 mol/L HCl. The mixture was added to EtOAc and the organic layer was separated, washed with water, dried over $Na_2SO_4$ and concentration. Recrystallization from 95% ethanol to give the title compound as a solid (5.0 g, 70.6%), mp: 126~128° C.

Preparation Example 17

Preparation of compounds F1~40

Compounds, F1~40, were prepared in the manner similar to the method of Preparation example 16, when Compounds E1~40 were used as the material respectively. The data of yield, melting points (Mp.) and $^1$H-NMR spectra of compounds F1~40 were shown in Table 11~20.

Preparation Example 18

6,7,8-Trifluoro-4-thiophenyl-3-bromomethyl-quinoline (G13)

A solution of $PBr_3$ (8.4 g, 31 mmol) in $CH_2Cl_2$ (40 ml) was added to the mixture of F13 (5.0 g, 15.5 mmol) in $CH_2Cl_2$ (30 ml) at 0° C. The resulting mixture was stirred for 10 minutes at 0° C. and then for 2 hour at room temperature before quenching with a saturated aqueous $NaHCO_3$ solution to pH 8. The mixture was added to $CH_2Cl_2$ and the organic layer was separated, washed with water, dried over $Na_2SO_4$, and concentrated to obtain the title compound (5.2 g, 86.8%), mp: 98~100° C. which was used without further purification.

Preparation Example 19

Preparation of compounds G1~40

Compounds G1~40 were prepared in the manner similar to the method of Preparation example 18, when Compounds F1~40 were used as the material respectively. The data of yield, and melting points (Mp.) of compounds G1~40 were shown in Table 21~30.

Preparation Example 20

6,7,8-Trifluoro-4-thiophenyl-3(diphenylphosphorylmethyl)-quinoline (B13)

A solution of G13 (5.2 g, 13.4 mmol) and ethyl diphenylphosphinite (6.2 ml, 27 mmol) in toluene (25 ml) was refluxed for 2 h during which time the precipitated solid developed. After cooling to room temperature, the solid was isolated by filtration and washed with toluene. The product was then dried to obtain the title compound (6.6 g, 96.9% yield), mp: 244-245° C.

Preparation Example 21

Preparation of compounds B1~40

Compounds B1~40 were prepared in the manner similar to the method of Preparation example 20, when Compounds G1~40 were used as the material respectively. The data of yield and melting points (Mp.) of compounds G1~40 were shown in Table 21~30.

Preparation Example 22 tert-Butyl (3R,5S,6E)-7-[6,7,8-trifluoro-4-thiophenyl-quinoline-3-yl]-3,5-dihydroxy-3,5-O-isopropylidene-6-heptenoate (D13)

1.2 ml (3 mmol) of 2.5 mol/L hexane solution of n-BuLi was added to a solution of 2,2,6,6-tetramethylpiperidine (0.5 g, 3 mmol) in anhydrous THF (10 ml) at 0° C. and stirred for 15 minutes under an atmosphere of nitrogen. B13 (1.0 g, 2.0 mmol) was added to the resulting solution at 0° C. and stirred for 1 hour at room temperature. Compound C (0.61 g, 2.4 mmol) in anhydrous THF (2 ml) was added to the solution and stirred for overnight before quenching with saturated aqueous $NaHCO_3$ solution (20 ml) at 0° C. The resulting mixture was added to EtOAc and the organic layer was separated, washed with brine, dried over Na$_2$SO$_4$ and concentrated. The resulting oil was purified by silica gel chromatography (petroleum ether-EtOAc, 5:1) to provide the title compound (0.6 g, 55.8%) as a solid, mp: 169-171° C.

Preparation Example 23

Preparation of compounds D1~40

Compounds D1~40 were prepared in the manner similar to the method of Preparation example 22, when Compounds B1~40 were used as material respectively. The data of yield, melting points (Mp.) and $^1$H-NMR spectra of compounds D1~40 were shown in Table 31~50.

Preparation Example 24

(4R,6S)-6-[(E)-2-(4-thiophenylquinoline-3-yl)-ethenyl]-3,4,5,6-tetrahydro-4-hydroxy-2H-pyran-2-one (A1)

A solution of D1 (0.44 g, 0.86 mmol) and CF$_3$COOH (2 ml, 25.8 mmol) in CH$_2$Cl$_2$ (10 ml) was stirred at 0° C. for 8 h before quenching with a saturated aqueous NaHCO$_3$ solution. The mixture was added to EtOAc and the organic layer was separated, washed with water, dried over Na$_2$SO$_4$, and concentrated. The resulting oil was purified by silica gel chromatography (petroleum ether-EtOAc, 2:1) to provide the title compound (0.30 g, 91.7%) as white solid. mp: 102-104° C.

Preparation Example 25

(4R,6S)-6-[(E)-2-(6,7,8-trifluoro-4-thiophenylquinoline-3-yl)-ethenyl]-3,4,5,6-tetrahydro-4-hydroxy-2H-pyran-2-one (A13)

A solution of D13 (0.47 g, 0.86 mmol) and CF$_3$COOH (2 ml, 25.8 mmol) in CH$_2$Cl$_2$ (10 ml) was stirred at 80° C. for 1 h before quenching with a saturated aqueous NaHCO$_3$ solution. The mixture was added to EtOAc and the organic layer was separated, washed with water, dried over Na$_2$SO$_4$, and concentrated. The resulting oil was purified by silica gel chromatography (petroleum ether-EtOAc, 2:1) to provide the title compound (0.30 g, 81.4%) as white solid. mp: 177-178° C.

Preparation Example 26

(4R,6S)-6-[(E)-2-(4-(4-fluoro-thiophenylquinoline-3-yl)-ethenyl]-3,4,5,6-tetrahydro-4-hydroxy-2H-pyran-2-one (A2)

A solution of D2 (0.86 mmol) and concentrated HCl (4 ml) in t-BuOMe (10 ml) was stirred at 25° C. for 8 h before quenching with a saturated aqueous NaHCO$_3$ solution. The mixture was added to EtOAc and the organic layer was separated, washed with water, dried over Na$_2$SO$_4$, and concentrated. The resulting oil was purified by silica gel chromatography (petroleum ether-EtOAc, 2:1) to provide the title compound.

Preparation Example 27

(4R,6S)-6-[(E)-2-(4-(3-methoxy-thiophenylquinoline-3-yl)-ethenyl]-3,4,5,6-tetrahydro-4-hydroxy-2H-pyran-2-one (A3)

A solution of D3 (0.86 mmol) and CH$_3$COOH (0.5 ml) in CHCl$_3$ (10 ml) was stirred at 30° C. for 4 h before quenching with a saturated aqueous NaHCO$_3$ solution.

The mixture was added to EtOAc and the organic layer was separated, washed with water, dried over Na$_2$SO$_4$, and concentrated. The resulting oil was purified by silica gel chromatography (petroleum ether-EtOAc, 2:1) to provide the title compound.

Preparation Example 28

(4R,6S)-6-[(E)-2-(4-(4-isopropyl-thiophenylquinoline-3-yl)-ethenyl]-3,4,5,6-tetrahydro-4-hydroxy-2H-pyran-2-one (A4)

A solution of D4 (0.86 mmol) and CH$_3$COOH (0.5 ml) in toluene (10 ml) was stirred at 30° C. for 3 h before quenching with a saturated aqueous NaHCO$_3$ solution. The mixture was added to EtOAc and the organic layer was separated, washed with water, dried over Na$_2$SO$_4$, and concentrated. The resulting oil was purified by silica gel chromatography (petroleum ether-EtOAc, 2:1) to provide the title compound.

Preparation Example 29

Preparation of Compound of A-A40

Compounds A1~40 were prepared in the manner similar to the method of Preparation example 24, when Compounds D1~40 were used as material respectively. The data of yield, melting points (Mp.) and $^1$H-NMR spectra of compounds A1~40 were shown in Table 51~70.

Efficacy Example

HMG CoA Reductase Inhibition Assay of Some Quinoline Compounds A In Vitro

The HMG CoA reductase inhibitory activity of compounds A in vitro was assayed following the method of "Kim H J et al: Characterization of β-hydroxy-β-methylglutaryl coenzyme A reductase inhibitor from Pueraria thunbergiana, J Agric Food Chem 2005, 53:5882-5888".

The HMG CoA reductase was extracted from the liver of Male Holtzman-Sprague-Dawley rats.

The positive control experiment was made with rosuvastatin, pitavastatin, atorvastatin, and fluvastatin. The negative control experiment was made without any inhibitor. The blank control experiment was made without HMG CoA and inhibitor.

3-Hydroxy-3-methylglutaryl-CoA (HMG CoA) reductase catalyzes the reduction of 1 mol HMG CoA and 2 mol NADPH to afford mevalonic acid and NADP.

NADPH shows a maximum absorption at 340 nm, and NADP shows no absorption at 340 nm. The reduction rate determined in this study was measured by the descending rate of ultraviolet absorption value at 340 nm. After addition of the inhibitor, the inhibitory activity of inhibitor on the enzyme can be calculated by the difference of ultraviolet absorption value. The in vitro HMG CoA reductase inhibition of some quinoline compounds in the invention was assayed by the method describe above.

The concentration of an inhibitor required to inhibit 50% of the HMG CoA reductase under the above assay conditions was defined as IC$_{50}$. The UV absorbance was measured in eight levels for each sample. A statistical analysis was performed by standard curve using mean values of triplicate measurements (n=3). The results were seen in Table 71.

The data of Table 71 showed that some quinoline compounds in this invention were more potent than fluvastatin, rosuvastatin or pitavastatin in HMG CoA reductase inhibition.

TABLE 1

Ethyl 4-substituted thiophenyl-quinoline-3-carboxylate (E1~4)

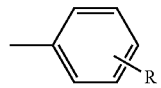

| No | R | Formula | Purification | yield % | Mp °C. | 2H | 8H | 5H | 6H | 7H | ⟨phenyl-R⟩ | Et |
|---|---|---|---|---|---|---|---|---|---|---|---|---|
| E1 | H | C₁₈H₁₅NO₂S | A | 88.9 | Oil | 9.07 s | 8.43 dd, J = 8.4, 1.2 | 8.14 d, J = 8.4 | 7.76-7.72 m | 7.55-7.51 m | 7.20-7.14 (m, 5H) | 4.25 (q, 2H, J = 7.2) 1.28 (t, 3H, J = 7.2) |
| E2 | p-F | C₁₈H₁₄FNO₂S | B | 89.9 | 52-4 | 9.05 s | 8.43 dd, J = 8.6, 0.8 | 8.14 d, J = 8.4 | 7.79-7.75 m | 7.59-7.55 m | 7.21 (dd, 2H, J = 11.8, 5.0) 6.93 (t, 2H, J = 6.4) | 4.30 (q, 2H, J = 7.6) 1.33 (t, 3H, J = 7.2) |
| E3 | m-OCH₃ | C₁₉H₁₇NO₃S | A | 90.2 | Oil | 9.06 s | 8.43 dd, J = 8.4, 1.2 | 8.13 dd, J = 8.8, 1.2 | 7.77-7.73 m | 7.57-7.52 m | 7.10 (t, 1H, J = 8.0) 6.75-6.67 (m, 3H) 3.66 (s, 3H) | 4.29 (q, 2H, J = 7.2) 1.31 (t, 3H, J = 7.2) |
| E4 | p-CH(CH₃)₂ | C₂₁H₂₁NO₂S | B | 98.0 | 44-6 | 9.03 s | 8.19 dd, J = 8.4, 0.8 | 8.13 d, J = 8.4 | 7.76-7.72 m | 7.56-7.52 m | 7.16-7.06 (m, 4H) 2.82 (t, 1H, J = 7.2) 1.18 (d, 6H, J = 6.8) | 4.21 (q, 2H, J = 6.8) 1.27 (t, 3H, J = 6.8) |

A: purified by silica gel chromatography (petroleum ether-EtOAc)
B: recrystalized by toluene/petroleum ether

TABLE 2

Ethyl 7-chloro-4-substituted thiophenyl-quinoline-3-carboxylate (E5~8)

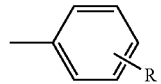

| | R | Formula | Purification | yield % | Mp °C. | 2H | 5H | 8H | 6H | ⟨phenyl-R⟩ | Et |
|---|---|---|---|---|---|---|---|---|---|---|---|
| E5 | H | C₁₈H₁₃ClNO₂S | B | 79.6 | 82-4 | 9.06 s | 8.37 d, J = 9.2 | 8.14 d, J = 2.0 | 7.48 dd, J = 9.2, 2.0 | 7.22-7.16 (m, 5H) | 4.26 (q, 2H, J = 7.2) 1.30 (t, 3H, J = 6.8) |
| E6 | p-F | C₁₈H₁₃ClFNO₂S | B | 97.1 | 91-4 | 9.04 s | 8.36 d, J = 9.2 | 8.13 d, J = 2.0 | 7.50 dd, J = 9.2, 2.0 | 7.21-7.18 (m, 2H) 6.95-6.91 (m, 2H) | 4.29 (q, 2H, J = 7.2) 1.32 (t, 3H, J = 7.2) |

TABLE 2-continued

Ethyl 7-chloro-4-substituted thiophenyl-quinoline-3-carboxylate (E5~8)

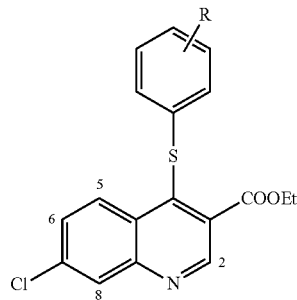

| | R | Formula | Purification | yield % | Mp °C | 2H | 5H | 8H | 6H | $^1$H-NMR δ ppm in CDCl$_3$ R-phenyl | Et |
|---|---|---|---|---|---|---|---|---|---|---|---|
| E7 | m-OCH$_3$ | C$_{19}$H$_{16}$ClNO$_3$S | A | 95.8 | 76-8 | 9.06 s | 8.35 d, J = 9.2 | 8.12 d, J = 2.0 | 7.47 dd, J = 9.2, 2.0 | 7.11-7.09 (m, 1H) 6.74-6.70 (m, 3H) 3.68 (s, 3H) | 4.29 (q, 2H, J = 6.8) 1.31 (t, 3H, J = 6.8) |
| E8 | p-CH(CH$_3$)$_2$ | C$_{21}$H$_{20}$ClNO$_2$S | B | 85.8 | 108-10 | 9.01 s | 8.40 d, J = 9.2 | 8.11 d, J = 2.0 | 7.47 dd, J = 9.2, 2.0 | 7.14-7.07 (m, 4H) 2.85-2.81 (m, 1H) 1.18 (d, 6H, J = 6.8) | 4.22 (q, 2H, J = 7.6) 1.28 (t, 3H, J = 7.2) |

A: purified by silica gel chromatography (petroleum ether-EtOAc)
B: recrystallized by toluene/petroleum ether

TABLE 3

Ethyl 6-fluoro-7-chloro-4-substituted thiophenyl-quinoline-3-carboxylate (E9~12)

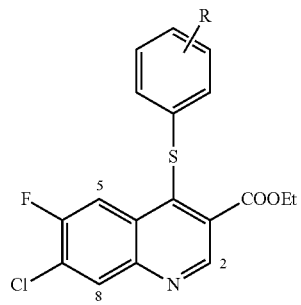

| No | R | Formula | Purification | yield % | Mp °C | 2H | 8H | 5H | $^1$H-NMR δ ppm in CDCl$_3$ R-phenyl | Et |
|---|---|---|---|---|---|---|---|---|---|---|
| E9 | H | C$_{18}$H$_{13}$ClFNO$_2$S | Petroleum ether | 91.7 | 94-6 | 9.02 s | 8.22, d, J = 7.6 | 8.14, d, J = 10.4 | 7.26-7.17 (m, 5H) | 4.28 (q, 2H, J = 7.2) 1.33 (t, 3H, J = 7.6) |
| E10 | p-F | C$_{18}$H$_{12}$ClF$_2$NO$_2$S | Petroleum ether | 88.5 | 100-2 | 9.00 s | 8.22 d, J = 6.8 | 8.13 d, J = 10.4 | 7.21 (dd, 2H, J = 11.8, 5.0) 6.95 (t, 2H, J = 7.6) | 4.31 (q, 2H, J = 7.2) 1.33 (t, 3H, J = 7.6) |
| E11 | m-OCH$_3$ | C$_{19}$H$_{15}$ClFNO$_3$S | A | 98.0 | 50-2 | 9.01 s | 8.20 d, J = 7.2 | 8.12 d, J = 10.4 | 7.15-7.11 (m, 1H) 6.74-6.71 (m, 3H) 3.69 (s, 3H) | 4.29 (q, 2H, J = 7.2) 1.28 (t, 3H, J = 7.6) |
| E12 | p-CH(CH$_3$)$_2$ | C$_{21}$H$_{19}$ClFNO$_2$S | B | 89.2 | 116-8 | 8.98 s | 8.20 d, J = 7.2 | 8.17 d, J = 10.4 | 7.15-7.09 (m, 4H) 2.84 (m, 2H) 1.20 (s, 3H), 1.19 (s, 3H) | 4.24 (q, 2H, J = 7.6) 1.29 (t, 3H, J = 7.2) |

A: purified by silica gel chromatography (petroleum ether-EtOAc)
B: recrystallized by toluene/petroleum ether

TABLE 4

Ethyl 6,7,8-trifluoro-4-substituted thiophenyl-quinoline-3-carboxylate (E13~16)

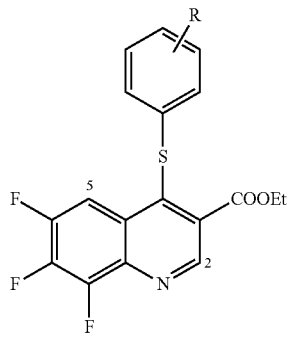

| No | R | Formula | yield* % | Mp °C. | 2H | 5H | [phenyl-R] | Et |
|---|---|---|---|---|---|---|---|---|
| E13 | H | $C_{18}H_{12}F_3NO_2S$ | 59.6 | 92-4 | 9.04 s | 8.05-7.99 m | 7.26-7.17 (m, 5H) | 4.27 (q, 2H, J = 7.2) 1.29 (t, 3H, J = 6.4) |
| E14 | p-F | $C_{18}H_{11}F_4NO_2S$ | 60.0 | 126-8 | 9.04 s | 8.05-8.00 m | 7.24-7.20 (m, 2H) 6.99-6.94 (m, 2H) | 4.30 (q, 2H, J = 7.2) 1.32 (t, 3H, J = 7.2) |
| E15 | m-OCH₃ | $C_{19}H_{14}F_3NO_3S$ | 55.8 | 70-2 | 9.07 s | 8.06-8.01 m | 7.16 (t, 1H, J = 8.0) 6.77-6.72 (m, 3H) 3.72 (s, 3H) | 4.31 (q, 2H, J = 7.2) 1.32 (t, 3H, J = 6.8) |
| E16 | p-CH(CH₃)₂ | $C_{21}H_{18}F_3NO_2S$ | 52.4 | 86-8 | 9.01 s | 8.08-8.03 m | 7.15-7.10 (m, 4H) 2.86-2.83 (m, 1H) 1.19 (d, 6H, J = 6.8) | 4.23 (q, 2H, J = 7.2) 1.28 (t, 3H, J = 7.2) |

*purified by silica gel chromatography (petroleum ether-EtOAc)

TABLE 5

Ethyl 4,7-disubstituted thiophenyl-quinoline-3-carboxylate (E17~20)

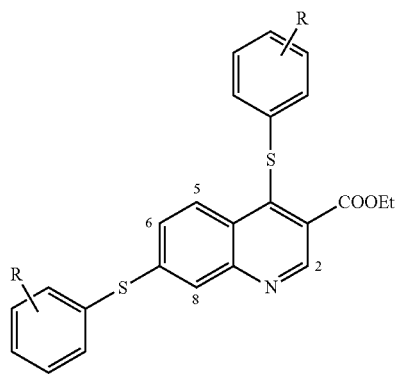

| No | R | Formula | yield* % | Mp °C. | 2H | 5H | 8H | 6H | [phenyl-R] | Et |
|---|---|---|---|---|---|---|---|---|---|---|
| E17 | H | $C_{24}H_{19}NO_2S_2$ | 80.0 | 98-100 | 8.98 s | 8.29 d, J = 9.2 | 7.76 d, J = 1.6 | 7.34 dd, J = 8.8, 1.6 | 7.56-7.54 (m, 2H), 7.42-7.40 (m, 3H), 7.22-7.15 (m, 5H) | 4.24 (q, 2H, J = 7.2) 1.28 (t, 3H, J = 7.6) |
| E18 | p-F | $C_{24}H_{17}F_2NO_2S_2$ | 91.2 | 68-70 | 8.96 s | 8.28 d, J = 9.2 | 7.66 s | 7.56 dd, J = 8.8, 5.6 | 7.56 (dd, 2H, J = 10.0, 5.2), 7.20-7.10 (m, 4H), 6.91 (t, 2H, J = 7.4) | 4.27 (q, 2H, J = 7.2) 1.30 (t, 3H, J = 7.2) |

TABLE 5-continued

Ethyl 4,7-disubstituted thiophenyl-quinoline-3-carboxylate (E17~20)

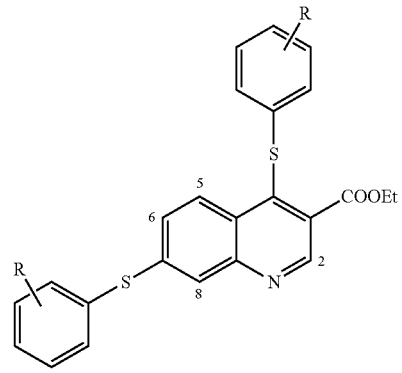

| No | R | Formula | yield* % | Mp °C. | 2H | 5H | 8H | 6H | $^1$H-NMR δ ppm in CDCl$_3$ | Et |
|---|---|---|---|---|---|---|---|---|---|---|
| E19 | m-OCH$_3$ | C$_{26}$H$_{23}$NO$_4$S$_2$ | 88.1 | Oil | 8.99 s | 8.29 d, J = 9.2 | 7.80 d, J = 2.0 | 7.36 dd, J = 8.8, 2.0 | 7.31 (t, 1H, J = 8.0), 7.14-7.07 (m, 3H), 6.95-6.92 (m, 1H), 6.73-6.68 (m, 3H), 3.78 (s, 3H), 3.68 (s, 3H) | 4.27 (q, 2H, J = 7.2) 1.30 (t, 3H, J = 7.2) |
| E20 | p-CH(CH$_3$)$_2$ | C$_{30}$H$_{31}$NO$_2$S$_2$ | 93.0 | Oil | 8.93 s | 8.32 d, J = 8.8 | 7.71 s | 7.34 dd, J = 9.2, 1.6 | 7.49 (d, 2H, J = 8.0), 7.28 (d, 2H, J = 8.4), 7.12-7.06 (m, 4H), 4.11 (q, 2H, J = 6.8), 2.95 (m, 1H), 2.83 (m, 1H), 1.31-1.14 (m, 15H) | |

*purified by silica gel chromatography (petroleum ether-EtOAc)

TABLE 6

Ethyl 6-fluoro-4,7-disubstituted thiophenyl-quinoline-3-carboxylate (E21~24)

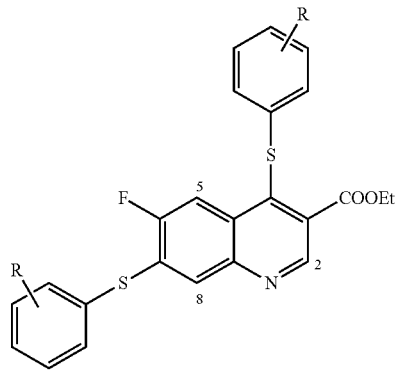

| No | R | Formula | Purification | yield % | Mp °C. | 2H | 5H | 8H | $^1$H-NMR δ ppm in CDCl$_3$ | Et |
|---|---|---|---|---|---|---|---|---|---|---|
| E21 | H | C$_{24}$H$_{18}$FO$_2$S$_2$ | A | 65.3 | Oil | 8.90 s | 8.02 d, J = 11.2 | 7.53 d, J = 8.0 | 7.60-7.57 (m, 2H), 7.46-7.44 (m, 3H), 7.25-7.15 (m, 5H) | 4.25 (q, 2H, J = 6.8) 1.27 (t, 3H, J = 7.2) |
| E22 | p-F | C$_{24}$H$_{16}$F$_3$NO$_2$S$_2$ | Toluene/ hexane | 89.0 | 146-8 | 8.89 s | 8.02 d, J = 10.8 | 7.45 d, J = 7.2 | 7.59 (dd, 2H, J = 7.0, 5.2), 7.22-7.15 (m, 4H), 6.94 (t, 2H, J = 7.6) | 4.28 (q, 2H, J = 7.2) 1.31 (t, 3H, J = 6.8) |
| | | | | | | | | | 7.36 (t, 1H, J = 8.0), 7.17-7.01 | 4.27 (q, 2H, |

TABLE 6-continued

Ethyl 6-fluoro-4,7-disubstituted thiophenyl-quinoline-3-carboxylate (E21~24)

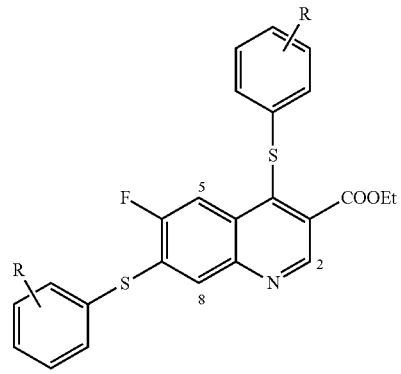

| No | R | Formula | Purification | yield % | Mp °C. | 2H | 5H | 8H | $\phantom{xxx}$R | Et |
|---|---|---|---|---|---|---|---|---|---|---|
| | | | | | | | | | $^1$H-NMR δ ppm in CDCl$_3$ | |
| E23 | m-OCH$_3$ | C$_{26}$H$_{22}$FNO$_4$S$_2$ | A | 60.0 | Oil | 8.92 s | 8.02 d, J = 11.2 | 7.56 d, J = 7.6 | (m, 3H), 7.00-6.97 (m, 1H), 6.74-6.70 (m, 3H) 3.80 (s, 3H), 3.69 (s, 3H) | J = 7.2) 1.27 (t, 3H, J = 6.8) |
| E24 | p-CH(CH$_3$)$_2$ | C$_{30}$H$_{30}$FNO$_2$S$_2$ | Toluene/ hexane | 77.7 | 88-90 | 8.86 s | 8.05 d, J = 11.2 | 7.53-7.50 (m, 3H), 7.32 (d, 2H, J = 8.0), 7.13-7.08 (m, 4H), 2.97 (t, 1H, J = 6.8), 2.84 (t, 1H, J = 6.8), 1.30 (d, 6H, J = 7.2), 1.20 (d, 6H, J = 6.8) | | 4.22 (q, 2H, J = 7.2) 1.26 (t, 3H, J = 7.2) |

A: purified by silica gel chromatography (petroleum ether-EtOAc)

TABLE 7

Ethyl 6,8-difluoro-4,7-disubstituted thiophenyl-quinoline-3-carboxylate (E25~28)

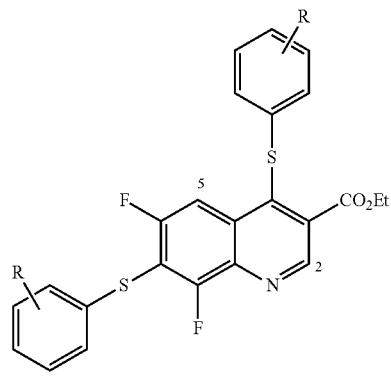

| No | R | Formula | Purification | Yield % | Mp °C. | 2H | 5H | $\phantom{xxx}$R | Et |
|---|---|---|---|---|---|---|---|---|---|
| | | | | | | | | $^1$H-NMR δ ppm in CDCl$_3$ | |
| E25 | H | C$_{24}$H$_{17}$F$_2$NO$_2$S$_2$ | A | 65.3 | 82-4 | 9.01 s | 7.93 dd, J = 10.2, 2.0 | 7.39-7.37 (m, 2H), 7.28-7.19 (m, 8H) | 4.25 (q, 2H, J = 7.2) 1.29 (t, 3H, J = 6.8) |
| E26 | p-F | C$_{24}$H$_{15}$F$_4$NO$_2$S$_2$ | B | 52.6 | 114-6 | 8.99 s | 7.91 dd, J = 9.0, 2.0 | 7.46 (dd, 2H, J = 8.6, 5.2), 7.23 (dd, 2H, J = 8.6, 4.8), 7.00-6.94 (m, 4H) | 4.28 (q, 2H, J = 7.2) 1.31 (t, 3H, J = 6.8) |

TABLE 7-continued

Ethyl 6,8-difluoro-4,7-disubstituted thiophenyl-quinoline-3-carboxylate (E25~28)

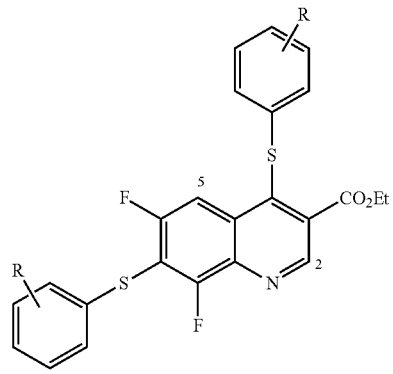

| No | R | Formula | Purification | Yield % | Mp ° C. | 2H | 5H | ¹H-NMR δ ppm in CDCl₃ ⟨C₆H₄-R⟩ | Et |
|---|---|---|---|---|---|---|---|---|---|
| E27 | m-OCH₃ | $C_{26}H_{21}F_2NO_4S_2$ | A | 60.0 | Oil | 9.02 s | 7.93 dd, J = 10.2, 1.2 | 7.18-7.13 (m, 2H), 6.94-6.91 (m, 2H), 6.78-6.73 (m, 4H), 3.73 (s, 3H), 3.71 (s, 3H) | 4.28 (q, 2H, J = 7.6) 1.31 (t, 3H, J = 7.2) |
| E28 | p-CH(CH₃)₂ | $C_{30}H_{29}F_2NO_2S_2$ | C | 50.0 | 75-7 | 8.97 s | 7.94 dd, J = 10.4, 2.0 | 7.35 (d, 2H, J = 8.0), 7.16-7.09 (m, 6H), 4.21 (q, 2H, J = 7.6), 2.88-2.83 (m, 2H), 1.29-1.19 (m, 15H) | |

A: purified by silica gel chromatography (petroleum ether-EtOAc)
B: recrystallized by petroleum ether-EtOAc.
C: recrystallized by petroleum ether

TABLE 8

Ethyl 4,6,7-trisubstituted thiophenyl-quinoline-3-carboxylate (E29~32)

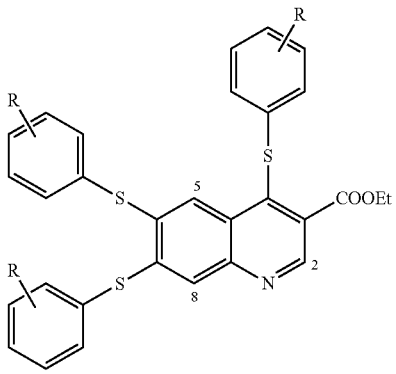

| No | R | Formula | Yield % | Mp ° C. | 2H | 8H | 5H | ¹H-NMR δ ppm in CDCl₃ ⟨C₆H₄-R⟩ | Et |
|---|---|---|---|---|---|---|---|---|---|
| E29 | H | $C_{30}H_{23}NO_2S_3$ | 90.2 | 110-3 | 9.10 s | 7.92 s | 7.88 s | 7.59-7.53 (m, 5H), 7.43-7.40 (m, 5H), 7.18 (d, 3H, J = 7.6), 6.88 (d, 3H, J = 7.6) | 4.29 (q, 2H, J = 6.8) 1.27 (t, 3H, J = 7.2) |

TABLE 8-continued

Ethyl 4,6,7-trisubstituted thiophenyl-quinoline-3-carboxylate (E29~32)

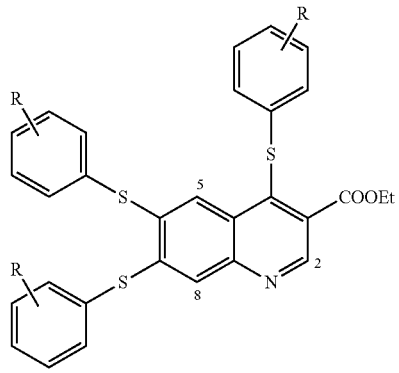

| No | R | Formula | Yield % | Mp °C. | 2H | 8H | 5H | R | Et |
|---|---|---|---|---|---|---|---|---|---|
| E30 | p-F | C₃₀H₂₀F₃NO₂S₃ | 88.0 | 118-22 | 8.87 s | 7.97 s | 7.44 s | 7.55 (dd, 2H, J = 7.0, 5.2), 7.34 (dd, 2H, J = 6.8, 5.2), 7.15 (t, 2H, J = 6.8), 7.04 (t, 2H, J = 8.4), 6.94 (dd, 2H, J = 7.0, 4.4), 6.85 (t, 2H, J = 8.4) | 4.30 (q, 2H, J = 6.8) 1.31 (t, 3H, J = 7.2) |
| E31 | m-OCH₃ | C₃₃H₂₉NO₅S₃ | 62.0 | Oil | 8.89 s | 8.18 s | 7.57 s | 7.34 (t, 1H, J = 8.0), 7.24-7.20 (m, 1H), 7.15-7.12 (m, 1H), 7.09 (t, 1H, J = 2.0) 7.00-6.97 (m, 1H), 6.74-6.70 (m, 3H) 3.80 (s, 3H), 3.69 (s, 3H) | 4.30 (q, 2H, J = 6.8) 1.31 (t, 3H, J = 7.2) |
| E32 | p-CH(CH₃)₂ | C₃₉H₁₄NO₂S₃ | 83.5 | Oil | 8.74 s | 7.98 s | 7.58 s | 7.51 (d, 2H, J = 8.0), 7.30 (d, 4H, J = 8.4), 7.19 (d, 2H, J = 8.4), 7.01 (d, 2H, J = 8.4), 7.76 (d, 2H, J = 8.0) | 4.27 (q, 2H, J = 7.2) 1.27 (t, 3H, J = 6.8) |

TABLE 9

Ethyl 6-fluoro-4,7,8-trisubstituted thiophenyl-quinoline-3-carboxylate (E33~36)

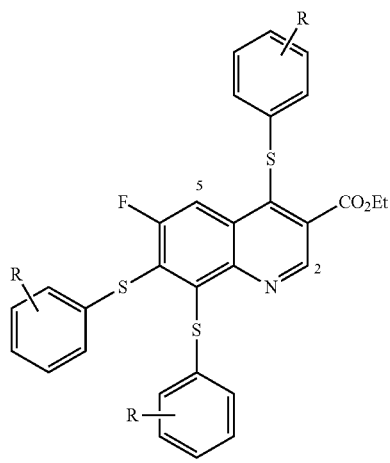

| No | R | Formula | Purification | Yield % | Mp °C. | 2H | 5H | R | Et |
|---|---|---|---|---|---|---|---|---|---|
| E33 | H | C₃₀H₂₂FNO₂S₃ | Toluene/ hexane | 69.1 | 128-30 | 9.05 s | 8.14 d, J = 10.8 | 7.26-7.11 (m, 15H) | 4.23 (q, 2H, J = 6.8) 1.26 (t, 3H, J = 7.2) |

TABLE 9-continued
Ethyl 6-fluoro-4,7,8-trisubstituted thiophenyl-quinoline-3-carboxylate (E33~36)
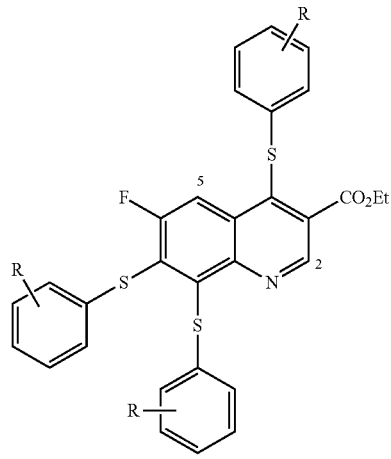
| No | R | Formula | Purification | Yield % | Mp °C. | 2H | 5H | ⟨aryl-R⟩ | Et |
|----|---|---------|--------------|---------|--------|-----|-----|----------|-----|
| E34 | p-F | $C_{30}H_{19}F_4NO_2S_3$ | EtOH | 89.3 | 80-3 | 9.03 s | 8.11 d, J = 10.4 | 7.28-7.21 (m, 6H), 6.97-6.87 (m, 6H) | 4.26 (q, 2H, J = 6.8) 1.26 (t, 3H, J = 7.2) |
| E35 | m-OCH$_3$ | $C_{33}H_{28}FNO_5S_3$ | A | 60.3 | 104-6 | 9.07 s | 8.14 d, J = 10.4 | 7.17 (m, 3H), 6.82-6.64 (m, 9H), 3.72 (s, 3H), 3.70 (s, 3H), 3.69 (s, 3H) | 4.27 (q, 2H, J = 6.8) 1.29 (t, 3H, J = 6.8) |
| E36 | p-CH(CH$_3$)$_2$ | $C_{39}H_{40}FNO_2S_3$ | A | 65.8 | Oil | 9.04 s | 8.14 d, J = 11.2 | 7.18-7.02 (m, 12H), 4.20 (q, 2H, J = 6.8), 2.88-2.81 (m, 3H), 1.33-1.15 (m, 2H) | |
A: purified by silica gel chromatography (petroleum ether-EtOAc)

TABLE 10

Ethyl 4,6,7,8-tetrasubstituted thiophenyl-quinoline-3-carboxylate (E37~40)

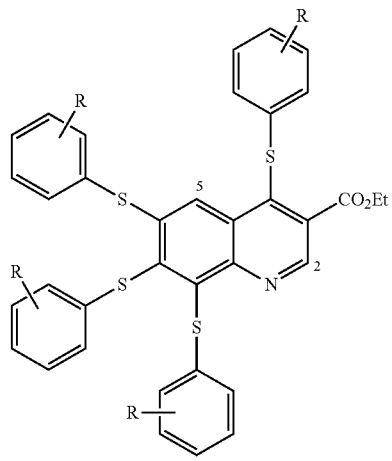

| No | R | Formula | Recrystalized solvent | Yield % | Mp °C. | 2H | 5H | $^1$H-NMR δ ppm in CDCl$_3$ — R (phenyl) | Et |
|---|---|---|---|---|---|---|---|---|---|
| E37 | H | C$_{36}$H$_{27}$NO$_2$S$_4$ | petroleum ether | 98.0 | 91-3 | 8.90 s | 7.88 s | 7.52-7.40 (m, 5H), 7.30-7.04 (m, 13H), 6.85-6.83 (m, 2H) | 4.25 (q, 2H, J = 6.8) 1.27 (t, 3H, J = 6.8) |
| E38 | p-F | C$_{36}$H$_{23}$F$_4$NO$_2$S$_4$ | toluene/hexane | 90.2 | 126-8 | 8.87 s | 7.72 s | 7.40 (dd, 2H, J = 9.8, 5.2), 7.19 (dd, 2H, J = 8.4, 5.2), 7.14-7.10 (m, 4H), 6.93-6.80 (m, 8H) | 4.27 (q, 2H, J = 7.6) 1.27 (t, 3H, J = 7.2) |
| E39 | m-OCH$_3$ | C$_{40}$H$_{35}$NO$_6$S$_4$ | A | 76.9 | oil | 8.92 s | 7.95 s | 7.29 (t, 1H, J = 8.0), 7.09 (t, 1H, J = 7.6), 7.05-6.94 (m, 5H), 6.73-6.58 (m, 7H), 6.44-6.37 (m, 2H), 3.76 (m, 3H), 3.67 (s, 3H), 3.65 (s, 3H), 3.64 (s, 3H) | 4.26 (q, 2H, J = 6.8) 1.27 (t, 3H, J = 7.2) |
| E40 | p-CH(CH$_3$)$_2$ | C$_{48}$H$_{51}$NO$_2$S$_4$ | A | 84.3 | oil | 8.86 s | 7.82 s | 7.34-7.25 (m, 4H), 7.13-7.10 (m, 2H), 7.06-6.95 (m, 8H), 6.77-6.75 (m, 2H), 3.00-2.97 (m, 1H), 2.85-2.76 (m, 3H), 1.34-1.16 (m, 24H) | 4.20 (q, 2H, J = 6.8) 0.86 (t, 3H, J = 5.2) |

A: purified by silica gel chromatography (petroleum ether-EtOAc)

TABLE 11

4-substituted thiophenyl quinoline-3-methanol (F1~4)

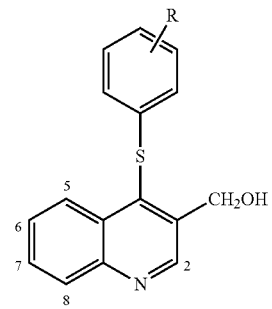

| | | | | | | | | | | | 1H-NMR δ ppm in CDCl3 | |
|---|---|---|---|---|---|---|---|---|---|---|---|---|
| No | R | Formula | Recrystalized solvent | Yield % | Mp ° C. | 2H | 8H | 5H | 6H | 7H | Ar-R | CH2 |
| F1 | H | C16H13NOS | petroleum ether/EtOAc | 64.6 | 144-6 | 9.09 s | 8.43 d, J = 8.4 | 8.14 d, J = 8.4 | 7.73-7.67 m | 7.56-7.52 m | 7.04-6.89 (m, 5H) | 5.03 s |
| F2 | p-F | C16H12FNOS | Et2O | 76.5 | 130-2 | 9.10 s | 8.43 m | 8.12 dd, J = 8.6, 0.8 | 7.72-7.67 m | 7.56-7.52 m | 7.05-7.01 (m, 2H) 6.90-6.85 (m, 2H) | 5.04 s |
| F3 | m-OCH3 | C17H15NO2S | A | 61.5 | 122-4 | 9.10 s | 8.38 d, J = 8.4 | 8.11 d, J = 8.0 | 7.70-7.66 m | 7.54-7.50 m | 7.04 (t, 1H, J = 8.0) 6.65-6.54 (m, 3H) 3.63 (s, 3H) | 5.02 s |
| F4 | p-CH(CH3)2 | C19H19NOS | petroleum ether/EtOAc | 63.9 | 100-2 | 9.09 s | 8.45 d, J = 8.4 | 8.14 d, J = 8.0 | 7.72-7.68 m | 7.56-7.52 m | 7.05-6.96 (m, 4H) 2.82-2.78 (m, 1H), 1.17 (d, 6H, J = 7.2) | 5.02 s |

A: purified by silica gel chromatography (petroleum ether-EtOAc)

TABLE 12

7-chloro-4-substituted thiophenyl-quinoline-3-methanol (F5~8)

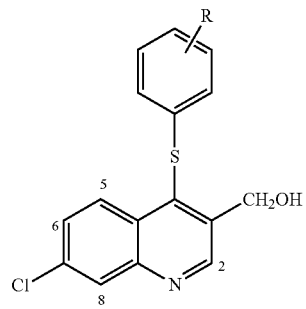

| | | | | | | | | | 1H-NMR δ ppm in CDCl3 | |
|---|---|---|---|---|---|---|---|---|---|---|
| No | R | Formula | Yield* % | Mp ° C. | 2H | 5H | 8H | 6H | Ar-R | CH2 |
| F5 | H | C16H11ClNOS | 52.8 | 122 | 9.11 s | 8.34 d, J = 9.2 | 8.13 d, J = 2.0 | 7.48 dd, J = 8.8, 2.0 | 7.21-7.14 (m, 3H), 7.03-7.09 (m, 2H) | 5.01 s |
| F6 | p-F | C16H11ClFNOS | 63.6 | 142-6 | 9.09 s | 8.31 d, J = 9.2 | 8.11 d, J = 2.0 | 7.48 dd, J = 8.8, 2.0 | 7.05-7.02 (m, 2H), 6.92-6.88 (m, 2H) | 5.02 s |

TABLE 12-continued 7-chloro-4-substituted thiophenyl-quinoline-3-methanol (F5~8)

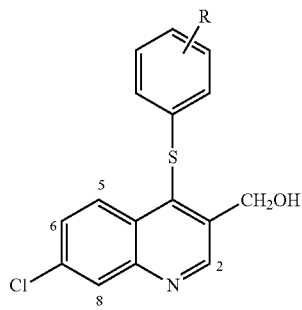

| No | R | Formula | Yield* % | Mp °C. | 2H | 5H | 8H | 6H | $^1$H-NMR δ ppm in CDCl$_3$ R | CH$_2$ |
|---|---|---|---|---|---|---|---|---|---|---|
| F7 | m-OCH$_3$ | C$_{17}$H$_{14}$ClNO$_2$S | 69.8 | 118 | 9.10 s | 8.33 d, J = 8.8 | 8.12 d, J = 2.0 | 7.48 dd, J = 8.8, 2.0 | 7.09 (t, 1H, J = 8.0), 6.69-6.66 (m, 1H), 6.59-6.54 (m, 2H), 3.67 (s, 3H) | 5.02 s |
| F8 | p-CH(CH$_3$)$_2$ | C$_{19}$H$_{18}$ClNOS | 53.3 | 88-90 | 9.09 s | 8.38 d, J = 9.2 | 8.12 d, J = 2.0 | 7.47 dd, J = 8.8, 2.0 | 7.06-6.96 (m, 4H), 2.82-2.79 (m, 1H), 1.17 (d, 6H, J = 7.2) | 5.00 s |

A: purified by silica gel chromatography (petroleum ether-EtOAc)

TABLE 13

6-fluoro-7-chloro-4-substituted thiophenyl--quinoline-3-methanol (F9~12)

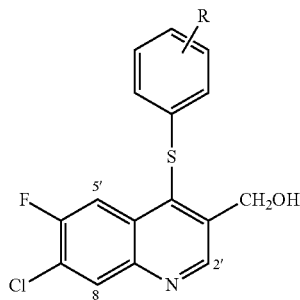

| No | R | Formula | Recrystalized solvent | Yield % | Mp °C. | 2H | 8H | 5H | $^1$H-NMR δ ppm in CDCl$_3$ R | CH$_2$ |
|---|---|---|---|---|---|---|---|---|---|---|
| F9 | H | C$_{16}$H$_{11}$ClFNOS | Toluene | 61.8 | 120-4 | 9.12 s | 8.25 d, J = 6.8 | 8.12 d, J = 10.0 | 7.25-7.18(m, 3H), 7.06-7.03(m, 2H) | 5.02 s |
| F10 | p-F | C$_{16}$H$_{10}$ClF$_2$NOS | Toluene | 62.2 | 154-6 | 9.09 s | 8.23 d, J = 7.6 | 8.11 d, J = 10.4 | 7.07-7.04(m, 2H), 6.95-6.91(m, 2H) | 5.03 s |
| F11 | m-OCH$_3$ | C$_{17}$H$_{13}$ClFNO$_2$S | Toluene | 75.6 | 117-8 | 9.11 s | 8.24 d, J = 7.6 | 8.14 d, J = 10.4 | 7.15-7.11(m, 1H), 6.73-6.70(m, 1H), 6.60-6.57(m, 2H), 3.71(s, 3H) | 5.04 s |
| F12 | p-CH(CH$_3$)$_2$ | C$_{19}$H$_{17}$ClFNOS | A | 73.9 | 132-4 | 9.06 s | 8.19 d, J = 6.8 | 8.13 d, J = 10.8 | 7.06(dd, 2H, J = 6.4, 2.0), 6.96 dd, 2H, J = 6.8, 2.0) 2.81(m, 2H), 1.17(d, 6H, J = 6.8) | 5.00 s |

A: purified by silica gel chromatography (petroleum ether-EtOAc)

TABLE 14

6,7,8-trifluoro-4-substituted thiophenyl-quinoline-3-methanol(F13~16)

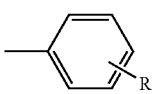

| No | R | Formula | Yield* % | Mp °C. | 2H | 5H | R-phenyl | CH$_2$ |
|---|---|---|---|---|---|---|---|---|
| F13 | H | C$_{16}$H$_{10}$F$_3$NOS | 70.6 | 126-8 | 9.15 s | 8.02-7.97 m | 7.24-7.17(m, 3H), 7.03-7.01(m, 2H) | 5.03 s |
| F14 | p-F | C$_{16}$H$_9$F$_4$NOS | 63.2 | 140-2 | 9.13 s | 8.00-7.95 m | 7.06-7.02(m, 2H), 6.92(t, 2H, J = 7.2) | 5.03 s |
| F15 | m-OCH$_3$ | C$_{17}$H$_{12}$F$_3$NO$_2$S | 63.2 | 100-2 | 9.16 s | 8.03-7.98 m | 7.13(t, 1H, J = 8.4), 6.73-6.70(m, 1H) 6.58-6.55(m, 2H), 3.70(s, 3H) | 5.04 s |
| F16 | p-CH(CH$_3$)$_2$ | C$_{19}$H$_{16}$F$_3$NOS | 76.7 | 99-102 | 9.13 s | 8.05-8.00 m | 7.10-7.06(m, 2H), 6.99-6.96(m, 2H) 2.84-2.81(m, 1H), 1.20-1.17(m, 6H) | 5.02 s |

A: purified by silica gel chromatography (petroleum ether-EtOAc)

TABLE 15

4,7-disubstituted thiophenyl-quinoline-3-methanol(F17~20)

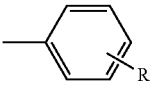

$^1$H-NMR δ ppm in CDCl$_3$

| No | R | Formula | Yield* % | Mp °C. | 2H | 5H | 8H | 6H | R-phenyl | CH$_2$ |
|---|---|---|---|---|---|---|---|---|---|---|
| F17 | H | C$_{22}$H$_{17}$NOS$_2$ | 53.1 | 104 | 9.00 s | 8.27 d, J = 8.8 | 7.83 d, J = 1.6 |  | 7.54-7.52(m, 2H), 7.13-7.08(m, 4H), 7.19-7.12(m, 3H), 6.91-6.87(m, 2H) | 4.97 s |
| F18 | p-F | C$_{22}$H$_{15}$F$_2$NOS$_2$ | 66.6 | 106-8 | 9.00 s | 8.25 d, J = 9.2 | 7.73 d, J = 1.6 | 7.34 dd, J = 9.2, 2.4 | 7.56-7.52(m, 2H), 7.13-7.08(m, 2H), 7.05-7.01(m, 2H), 6.91-6.87(m, 2H) | 4.98 s |
| F19 | m-OCH$_3$ | C$_{24}$H$_{23}$$_{21}$NO$_3$S$_2$ | 49.4 | 82-4 | 9.02 s | 8.28 d, J = 8.8 | 7.88 d, J = 1.6 | 7.39 dd, J = 8.8, 2.0 | 7.29(t, 1H, J = 8.0),7.12-7.06(m, 3H), 6.92-6.89(m, 1H), 6.68-6.65(m, 1H), 6.60-6.55(m, 2H), 3.78(s, 3H), 3.68(s, 3H) | 4.98 s |

TABLE 15-continued 4,7-disubstituted thiophenyl-quinoline-3-methanol(F17~20)

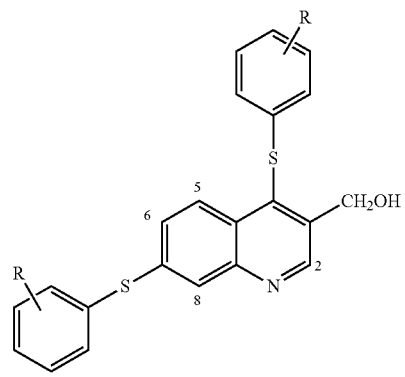

| | | | | | <sup>1</sup>H-NMR δ ppm in CDCl₃ | | | | | |
|---|---|---|---|---|---|---|---|---|---|---|
| No | R | Formula | Yield* % | Mp °C. | 2H | 5H | 8H | 6H | R (aryl) | CH₂ |
| F20 | p-CH(CH₃)₂ | C₂₈H₂₉NOS₂ | 63.5 | 114 | 8.97 s | 8.30 d, J = 9.2 | 7.77 s | 7.36 dd, J = 8.8, 1.6 | 7.48(d, 2H, J = 8.4), 7.26(d, 2H, J = 8.0), 7.04(d, 2H, J = 8.0), 6.95(d, 2H, J = 8.0), 2.95-2.92(m, 1H), 2.83-2.79(m, 1H), 1.28(d, 2H, J = 6.8), 1.17(d, 2H, J = 7.2) | 4.96 s |

A: purified by silica gel chromatography (petroleum ether-EtOAc)

TABLE 16

6-fluoro-4,7-disubstituted thiophenyl-quinoline-3-methanol(F21~24)

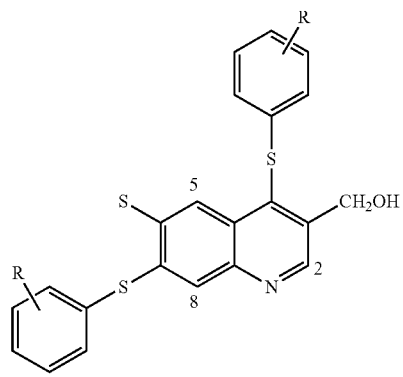

| | | | | | | | | | <sup>1</sup>H-NMR δ ppm in CDCl₃ | |
|---|---|---|---|---|---|---|---|---|---|---|
| No | R | Formula | Recrystalized solvent | Yield % | Mp °C. | 2H | 5H | 8H | R (aryl) | CH₂ |
| F21 | H | C₂₂H₁₆FNOS₂ | A | 50.6 | 88-90 | 8.91 s | 7.97 d, J = 11.2 | 7.60 d, J = 7.2 | 7.54-7.53(m, 2H), 7.40-7.39(m, 3H), 7.18-7.11(m, 3H), 6.99(d, 2H, J = 7.2) | 4.92 s |
| F22 | p-F | C₂₂H₁₄F₃NOS₂ | toluene | 87.5 | 108-10 | 8.95 s | 7.99 d, J = 11.2 | 7.52 d, J = 7.6 | 7.60-7.59(m, 2H), 7.15(t, 2H, J = 8.0) 7.06-7.03(m, 2H), 6.92(t, 2H, J = 8.0) | 4.98 s |
| F23 | m-OCH₃ | C₂₄H₂₀FNO₃S₂ | A | 45.9 | 93-5 | 8.95 s | 8.01 d, J = 11.2 | 7.67 d, J = 6.8 | 7.33(t, 1H, J = 8.0), 7.15-7.08(m, 3H), 6.97-6.94(m, 1H), 6.70-6.67(m, 1H), 6.58-6.56(m, 2H), 3.79(s, 3H), 3.69(s, 3H) | 4.96 s |

TABLE 16-continued 6-fluoro-4,7-disubstituted thiophenyl-quinoline-3-methanol(F21~24)

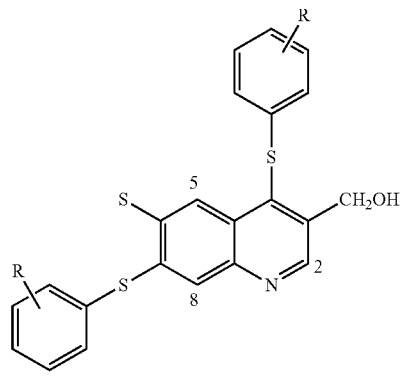

| No | R | Formula | Recrystalized solvent | Yield % | Mp °C. | 2H | 5H | 8H | $^1$H-NMR δ ppm in CDCl$_3$ phenyl-R | CH$_2$ |
|---|---|---|---|---|---|---|---|---|---|---|
| F24 | p-CH(CH$_3$)$_2$ | C$_{28}$H$_{28}$FNOS$_2$ | EtOH/ petroleum ether | 59.8 | 126-8 | 8.91 s | 8.03 d, J = 11.2 | 7.55 d, J = 8.0 | 7.53-7.50(m, 2H), 7.31(d, 2H, J = 8.4), 7.06(d, 2H, J = 8.4), 6.97-6.95(m, 2H), 2.98-2.94(m, 1H), 2.83-2.78(m, 1H), 1.30-1.27(m, 6H), 1.18(d, 6H, J = 6.8) | 4.95 s |

A: purified by silica gel chromatography (petroleum ether-EtOAc)

TABLE 17

6,8-difluoro-4,7-disubstituted thiophenyl-quinoline-3-methanol(F25~28)

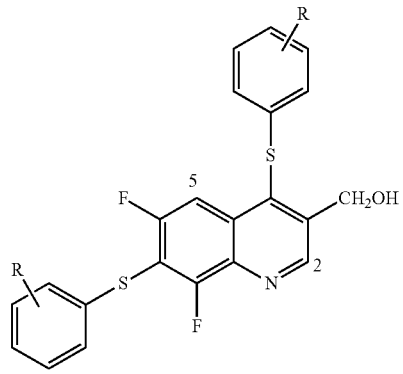

| No | R | Formula | Recrystalized solvent | Yield % | Mp °C. | 2H | 5H | $^1$H-NMR δ ppm in CDCl$_3$ phenyl-R | CH$_2$ |
|---|---|---|---|---|---|---|---|---|---|
| F25 | H | C$_{22}$H$_{15}$F$_2$NOS$_2$ | A | 73.7 | 134-6 | 9.14 s | 7.92 dd, J = 9.6, 2.0 | 7.38-7.25(m, 2H), 7.25-7.14(m, 6H), 7.04-7.02(m, 2H) | 5.02 s |
| F26 | p-F | C$_{22}$H$_{13}$F$_4$NOS$_2$ | Petroleum ether/ EtOH | 75.7 | 149-50 | 9.12 s | 7.88 d, J = 10.0 | 7.45(dd, 2H, J = 7.6, 5.2), 7.06(dd, 2H, J = 8.0, 5.2), 6.98-6.90(m, 4H) | 5.03 s |
| F27 | m-OCH$_3$ | C$_{24}$H$_{19}$F$_2$NO$_3$S$_2$ | A | 57.2 | 122-4 | 9.14 s | 7.93 dd, J = 10.0, 1.6 | 7.18-7.10(m, 2H), 6.93-6.89(m, 2H), 6.77-6.74(m, 2H), 6.59-6.57(m, 2H), 3.73(s, 3H), 3.70(s, 3H) | 5.03 s |
| F28 | p-CH(CH$_3$)$_2$ | C$_{28}$H$_{27}$F$_2$NOS$_2$ | EtOAc | 71.8 | 152-4 | 9.10 s | 7.95 dd, J = 10.4, 2.5 | 7.35(d, 2H, J = 7.4), 7.13-7.07(m, 4H), 7.00-6.97(m, 2H), 2.87-2.81(m, 2H), 1.21-1.18(m, 12H) | 5.01 s |

A: purified by silica gel chromatography (petroleum ether-EtOAc)

TABLE 18

4,6,7-trisubstituted thiophenyl-quinoline-3-methanol(F29~32)

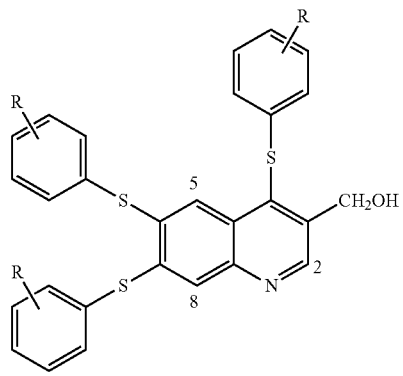

| No | R | Formula | Recrystalized solvent | Yield % | Mp °C. | 2H | 8H | 5H | $^1$H-NMR δ ppm in CDCl$_3$ (aryl-R) | CH$_2$ |
|---|---|---|---|---|---|---|---|---|---|---|
| F29 | H | C$_{28}$H$_{21}$NOS$_3$ | Petroleum ether | 60.9 | 190-3 | 9.13 s | 7.93 s | 7.88 s | 7.60-7.54(m, 5H), 7.44-7.40(m, 5H), 7.19-7.17(m, 3H), 6.88-6.87(m, 2H) | 4.88 s |
| F30 | p-F | C$_{28}$H$_{18}$F$_3$NOS$_3$ | Petroleum ether | 74.1 | 174-6 | 8.91 s | 7.87 s | 7.52 s | 7.57-7.52(m, 2H), 7.34-7.30(m, 2H), 7.14(t, 2H, J = 8.0), 7.01(t, 2H, J = 8.4), 6.88-6.87(m, 4H) | 4.98 s |
| F31 | m-OCH$_3$ | C$_{31}$H$_{27}$NO$_4$S$_3$ | A | 68.7 | 112-5 | 8.90 s | 8.12 s | 7.64 s | 7.32(t, 1H, J = 8.0), 7.19-6.82(m, 8H), 6.64-6.62(m, 1H), 6.43(t, 1H, J = 2.0), 6.39-6.36(m, 1H), 3.78(s, 3H), 3.71(s, 3H), 3.66(s, 3H) | 4.94 s |
| F32 | p-CH(CH$_3$)$_2$ | C$_{37}$H$_{39}$NOS$_3$ | A | 71.8 | 96-8 | 8.84 s | 7.99 s | 7.57 s | 7.50(d, 2H, J = 8.0), 7.29(d, 2H, J = 8.4), 7.18(d, 2H, J = 8.4), 6.99(d, 2H, J = 8.4), 6.74(d, 2H, J = 8.0), 2.97-2.92(m, 2H), 2.84-2.81(m, 2H), 1.30-1.20(m, 18H) | 4.93 s |

A: purified by silica gel chromatography (petroleum ether-EtOAc)

TABLE 19

6-fluoro-4,7,8-trisubstituted thiophenyl-quinoline-3-methanol(F33~36)

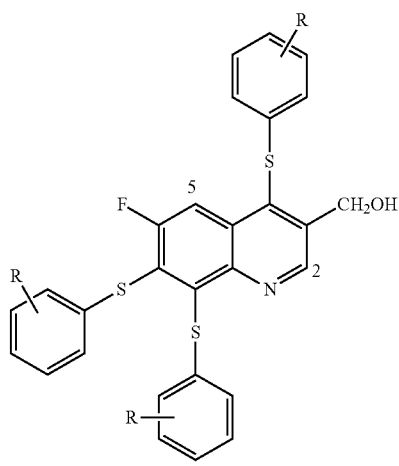

| No | R | Formula | Recrystalized solvent | Yield % | Mp °C. | 2H | 5H | $^1$H-NMR δ ppm in CDCl$_3$ (aryl-R) | CH$_2$ |
|---|---|---|---|---|---|---|---|---|---|
| F33 | H | C$_{28}$H$_{20}$FNOS$_3$ | A | 65.0 | 154-6 | 9.17 s | 8.15 d, J = 10.8 | 7.26-7.04(m, 15H) | 5.00 s |

TABLE 19-continued 6-fluoro-4,7,8-trisubstituted thiophenyl-quinoline-3-methanol(F33~36)

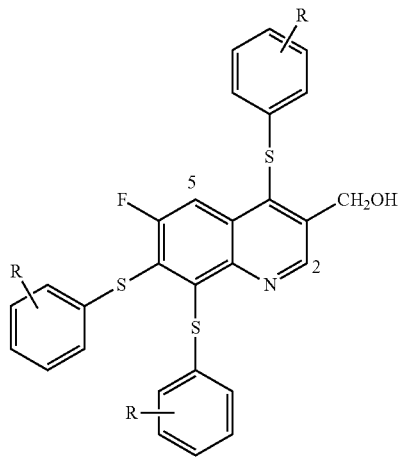

| No | R | Formula | Recrystalized solvent | Yield % | Mp °C. | 2H | 5H | ⟨phenyl-R⟩ | CH$_2$ |
|---|---|---|---|---|---|---|---|---|---|
| F34 | p-F | C$_{28}$H$_{17}$F$_4$NOS$_3$ | Petroleum ether | 78.5 | 200-3 | 9.15 s | 8.10 d, J = 10.8 | 7.26-7.21(m, 5H), 7.08-7.04(m, 2H), 6.95-6.86(m, 5H) | 5.00 s |
| F35 | m-OCH$_3$ | C$_{31}$H$_{26}$FNO$_4$S$_3$ | A | 66.9 | 110-2 | 9.17 s | 8.15 d, J = 10.4 | 7.14-7.04(m, 3H), 6.80-6.78(d, 1H, J = 8.0), 6.75-6.67(m, 5H), 6.64-6.61(m, 1H), 6.59-6.57(m, 2H), 3.73-3.68(m, 9H) | 5.00 s |
| F36 | p-CH(CH$_3$)$_2$ | C$_{37}$H$_{38}$FNOS$_3$ | A | 41.3 | 140-2 | 9.20 s | 8.19 d, J = 10.8 | 7.21-7.02(m, 12H), 2.91-2.82(m, 3H), 1.25-1.18(m, 18H) | 5.03 s |

A: purified by silica gel chromatography (petroleum ether-EtOAc)

TABLE 20

4,6,7,8-tetrasubstituted thiophenyl-quinoline-3-methanol(F37~40)

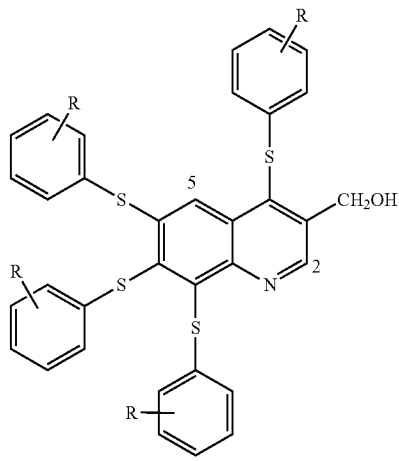

| No | R | Formula | Recrystalized solvent | Yield % | Mp °C. | 2H | 5H | ⟨phenyl-R⟩ | CH$_2$ |
|---|---|---|---|---|---|---|---|---|---|
| F37 | H | C$_{34}$H$_{25}$NOS$_4$ | A | 46.8 | 163-5 | 8.98 s | 7.81 s | 7.39-7.28(m, 5H), 7.20-7.03(m, 13H), 6.72-6.69(m, 2H) | 4.94 s |

TABLE 20-continued

4,6,7,8-tetrasubstituted thiophenyl-quinoline-3-methanol(F37~40)

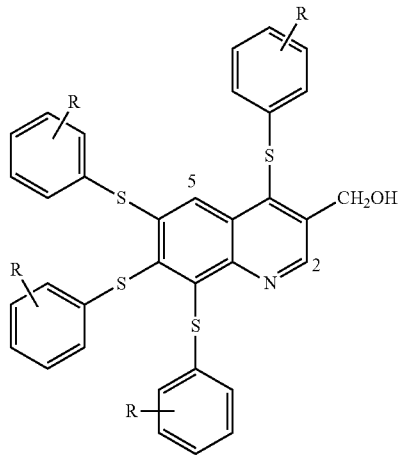

| No | R | Formula | Recrystalized solvent | Yield % | Mp ° C. | 2H | 5H | $^1$H-NMR δ ppm in CDCl$_3$ R (phenyl) | CH$_2$ |
|---|---|---|---|---|---|---|---|---|---|
| F38 | p-F | C$_{34}$H$_{21}$F$_4$NOS$_4$ | EtOH | 87.2 | 190-2 | 9.00 s | 7.61 s | 7.37-7.34(m, 2H), 7.20-7.16(m, 2H), 7.13-7.09(m, 2H), 7.07-7.02(m, 2H), 6.93-6.79(m, 6H), 6.69-6.65(m, 2H) | 4.96 s |
| F39 | m-OCH$_3$ | C$_{38}$H$_{33}$NO$_5$S$_4$ | A | 55.4 | 116-8 | 9.01 s | 7.87 s | 7.22(t, 1H, J = 8.0), 7.09(t, 1H, J = 8.4), 7.04-6.92(m, 5H), 6.73-6.55(m, 7H), 6.30-6.24(m, 2H), 3.70(s, 3H), 3.67(s, 3H), 3.66(s, 3H), 3.64(s, 3H) | 4.94 s |
| F40 | p-CH(CH$_3$)$_2$ | C$_{46}$H$_{49}$NOS$_4$ | A | 55.0 | 170-3 | 8.96 s | 7.78 s | 7.30(d, 2H, J = 7.0), 7.19(d, 2H, J = 8.0), 7.12(d, 2H, J = 7.4), 7.06-6.94(m, 8H), 6.65(d, 2H, J = 7.4), 2.96-2.93(m, 1H), 2.86-2.76(m, 3H), 1.29-1.14(m, 24H) | 4.93 s |

A: purified by silica gel chromatography (petroleum ether-EtOAc).

TABLE 21

4-substituted thiophenyl-3-bromomethyl(or 3-diphenyl-phosphoryl-methyl)-quinoline (G1~4 or B1~4)

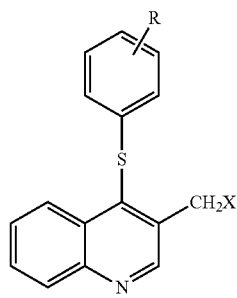

| No | R | X | Formula | Yield % | Mp ° C. |
|---|---|---|---|---|---|
| G1 | H | Br | C$_{16}$H$_{12}$BrNS | 67.2 | 156-60 |
| G2 | p-F | Br | C$_{16}$H$_{11}$BrFNS | 76.5 | 130-2 |
| G3 | m-OCH$_3$ | Br | C$_{17}$H$_{14}$BrNOS | 85.4 | 100 |
| G4 | p-CH(CH$_3$)$_2$ | Br | C$_{19}$H$_{18}$BrNS | — | — |
| B1 | H | P(O)Ph$_2$ | C$_{28}$H$_{23}$NOPS | 81.5 | 228-30 |
| B2 | p-F | P(O)Ph$_2$ | C$_{28}$H$_{22}$FNOPS | 100 | 184-5 |
| B3 | m-OCH$_3$ | P(O)Ph$_2$ | C$_{29}$H$_{25}$NO$_2$PS | 100 | 197-8 |
| B4 | p-CH(CH$_3$)$_2$ | P(O)Ph$_2$ | C$_{31}$H$_{29}$NOPS | 79.4* | 190-2 |

*: two steps' yield

TABLE 22

7-chloro-4-substituted thiophenyl-3-bromomethyl(or 3-diphenyl-phosphoryl-methyl)-quinoline (G5~8 or B5~8)

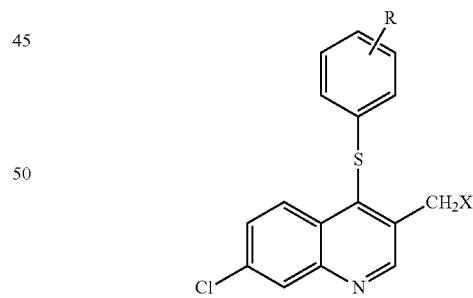

| No | R | X | Formula | Yield % | Mp ° C. |
|---|---|---|---|---|---|
| G5 | H | Br | C$_{16}$H$_{11}$BrClNS | 87.0 | 104-6 |
| G6 | p-F | Br | C$_{16}$H$_{10}$BrClFNS | 83.3 | 112-4 |
| G7 | m-OCH$_3$ | Br | C$_{17}$H$_{13}$BrClNOS | 86.1 | 92-4 |
| G8 | p-CH(CH$_3$)$_2$ | Br | C$_{19}$H$_{17}$BrClNS | 86.5 | 101-2 |
| B5 | H | P(O)Ph$_2$ | C$_{28}$H$_{21}$ClNOPS | 98.7 | 210-2 |
| B6 | p-F | P(O)Ph$_2$ | C$_{28}$H$_{20}$ClFNOPS | 100 | 192-4 |
| B7 | m-OCH$_3$ | P(O)Ph$_2$ | C$_{29}$H$_{23}$ClNO$_2$PS | 92.9 | 194-6 |
| B8 | p-CH(CH$_3$)$_2$ | P(O)Ph$_2$ | C$_{31}$H$_{27}$ClNOPS | 99.8 | 238-40 |

*: two steps' yield

TABLE 23

7-chloro-6-fluoro-4-substituted thiophenyl-3-bromomethyl(or 3-diphenyl-phosphoryl-methyl)-quinoline (G9~12 or B9~12)

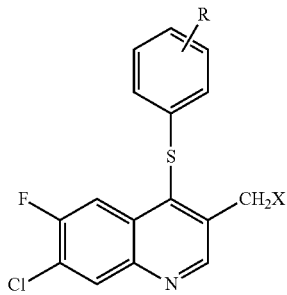

| No  | R          | X        | Formula             | Yield % | Mp ° C. |
|-----|------------|----------|---------------------|---------|---------|
| G9  | H          | Br       | C16H10BrClFNS       | 85      | 130-2   |
| G10 | p-F        | Br       | C16H9BrClF2NS       | 84.5    | 156-7   |
| G11 | m-OCH3     | Br       | C17H12BrClFNOS      | 83      | 108-10  |
| G12 | p-CH(CH3)2 | Br       | C19H16BrClFNS       | 85.0    | 132-4   |
| B9  | H          | P(O)Ph2  | C28H20ClFNOPS       | 88.9    | 238-40  |
| B10 | p-F        | P(O)Ph2  | C28H19ClF2NOPS      | 100     | 250-2   |
| B11 | m-OCH3     | P(O)Ph2  | C29H22ClFNO2PS      | 87.8    | 216-8   |
| B12 | p-CH(CH3)2 | P(O)Ph2  | C31H26ClFNOPS       | 100     | 234-6   |

TABLE 24

6,7,8-trifluoro-4-substituted thiophenyl-3-bromomethyl(or 3-diphenyl-phosphoryl-methyl)-quinoline (G13~16 or B13~16)

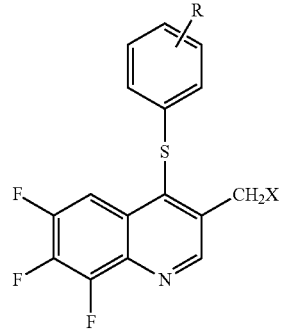

| No  | R          | X        | Formula           | Yield % | Mp ° C. |
|-----|------------|----------|-------------------|---------|---------|
| G13 | H          | Br       | C16H9BrF3NS       | 86.8    | 98-100  |
| G14 | p-F        | Br       | C16H8BrF4NS       | —       | —       |
| G15 | m-OCH3     | Br       | C17H11BrF3NOS     | 80.3    | 112-4   |
| G16 | p-CH(CH3)2 | Br       | C19H15BrF3NS      | 86.6    | 86-8    |
| B13 | H          | P(O)Ph2  | C28H19F3NOPS      | 96.9    | 244-5   |
| B14 | p-F        | P(O)Ph2  | C28H18F4NOPS      | 84.2*   | 212-3   |
| B15 | m-OCH3     | P(O)Ph2  | C29H21F3NO2PS     | 99.1    | 206-8   |
| B16 | p-CH(CH3)2 | P(O)Ph2  | C31H25F3NOPS      | 87.9    | 236-8   |

*: two steps' yield

TABLE 25

4,7-disubstituted thiophenyl-3-bromomethyl(or 3-diphenyl-phosphoryl-methyl)-quinoline (G17~20 or B17~20)

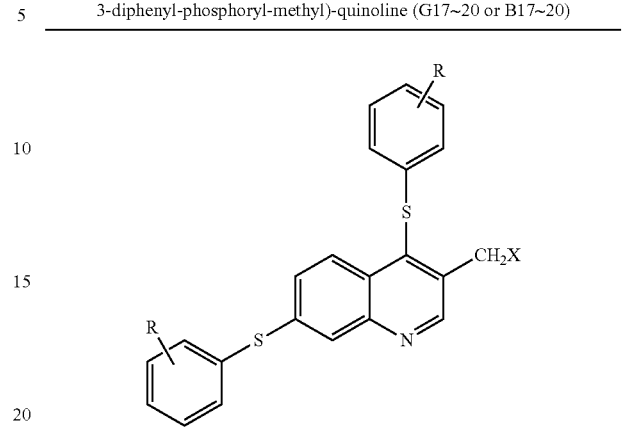

| No  | R          | X        | Formula         | Yield % | Mp ° C. |
|-----|------------|----------|-----------------|---------|---------|
| G17 | H          | Br       | C22H16BrNS2     | —       | —       |
| G18 | p-F        | Br       | C22H14BrF2NS2   | —       | —       |
| G19 | m-OCH3     | Br       | C24H20BrNO2S2   | —       | —       |
| G20 | p-CH(CH3)2 | Br       | C28H28BrNS2     | 81.9    | 87-90   |
| B17 | H          | P(O)Ph2  | C34H26NOPS2     | 71.6*   | 238-40  |
| B18 | p-F        | P(O)Ph2  | C34H24F2NOPS2   | 89.8*   | 213-5   |
| B19 | m-OCH3     | P(O)Ph2  | C36H30NO3PS2    | 87.8*   | 190-2   |
| B20 | p-CH(CH3)2 | P(O)Ph2  | C40H38NOPS2     | 100     | 200-2   |

*: two steps' yield

TABLE 26

6-fluoro-4,7-disubstituted thiophenyl-3-bromomethyl(or 3-diphenyl-phosphoryl-methyl)-quinoline (G21~24 or B21~24)

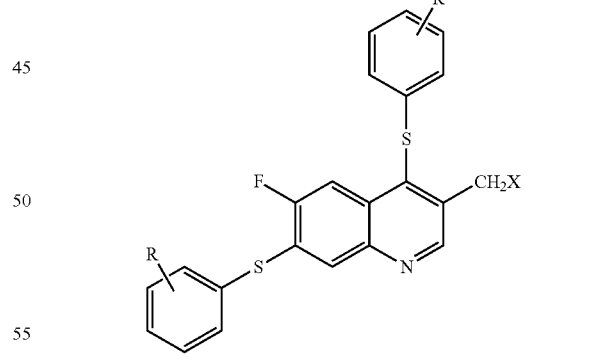

| No  | R          | X        | Formula         | Yield % | Mp ° C. |
|-----|------------|----------|-----------------|---------|---------|
| G21 | H          | Br       | C22H15BrFNS2    | —       | 104     |
| G22 | p-F        | Br       | C22H13BrF3NS2   | 89.8    | 150-2   |
| G23 | m-OCH3     | Br       | C24H19BrFNO2S2  | —       | oil     |
| G24 | p-CH(CH3)2 | Br       | C28H27BrFNS2    | 74.2    | 145-7   |
| B21 | H          | P(O)Ph2  | C34H25FNOPS2    | 62.0*   | 238-41  |
| B22 | p-F        | P(O)Ph2  | C34H23F3NOPS2   | 100     | 246-8   |
| B23 | m-OCH3     | P(O)Ph2  | C36H29FNO3PS2   | 84.0*   | 229-30  |
| B24 | p-CH(CH3)2 | P(O)Ph2  | C40H37FNOPS2    | 96.3    | 250-1   |

*two steps' yield

TABLE 27

6,8-difluoro-4,7-disubstituted thiophenyl-3-bromomethyl(or 3-diphenyl-phosphoryl-methyl)-quinoline (G25~28 or B25~28)

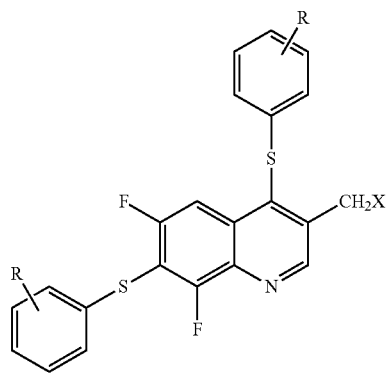

| No | R | X | Formula | Yield % | Mp ° C. |
|---|---|---|---|---|---|
| G25 | H | Br | $C_{22}H_{14}BrF_2NS_2$ | 76.6 | 120-2 |
| G26 | p-F | Br | $C_{22}H_{12}BrF_4NS_2$ | — | — |
| G27 | m-OCH$_3$ | Br | $C_{24}H_{18}BrF_2NO_2S_2$ | — | — |
| G28 | p-CH(CH$_3$)$_2$ | Br | $C_{28}H_{26}BrF_2NS_2$ | 80.3 | 116-7 |
| B25 | H | P(O)Ph$_2$ | $C_{34}H_{24}F_2NOPS_2$ | 72.9 | 246-8 |
| B26 | p-F | P(O)Ph$_2$ | $C_{34}H_{22}F_4NOPS_2$ | 72.4* | 250-2 |
| B27 | m-OCH$_3$ | P(O)Ph$_2$ | $C_{36}H_{28}F_2NO_3PS_2$ | 85.4* | 184-5 |
| B28 | p-CH(CH$_3$)$_2$ | P(O)Ph$_2$ | $C_{40}H_{36}F_2NOPS_2$ | 98.7 | 236-40 |

*two steps' yield

TABLE 28

4,6,7-trisubstituted thiophenyl-3-bromomethyl(or 3-diphenyl-phosphoryl-methyl)-quinoline (G29~32 or B29~32)

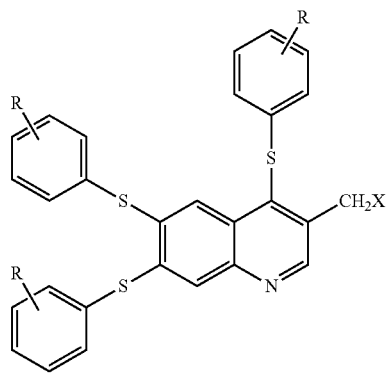

| No | R | X | Formula | Yield % | Mp ° C. |
|---|---|---|---|---|---|
| G29 | H | Br | $C_{28}H_{20}BrNS_3$ | 88.9 | 140-2 |
| G30 | p-F | Br | $C_{28}H_{17}BrF_3NS_3$ | 82.2 | 156-8 |
| G31 | m-OCH$_3$ | Br | $C_{31}H_{26}BrNO_3S_3$ | — | — |
| G32 | p-CH(CH$_3$)$_2$ | Br | $C_{37}H_{38}BrNS_3$ | 69.3 | 104-7 |
| B29 | H | P(O)Ph$_2$ | $C_{40}H_{30}NOPS_3$ | 94.2 | 246-8 |
| B30 | p-F | P(O)Ph$_2$ | $C_{40}H_{27}F_3NOPS_3$ | 90.7 | 261-3 |
| B31 | m-OCH$_3$ | P(O)Ph$_2$ | $C_{43}H_{36}NO_4PS_3$ | 82.1* | 156-8 |
| B32 | p-CH(CH$_3$)$_2$ | P(O)Ph$_2$ | $C_{49}H_{48}NOPS_3$ | 97.1 | 231-3 |

*two steps' yield

TABLE 29

6-fluoro-4,7,8-trisubstituted thiophenyl-3-bromomethyl(or 3-diphenyl-phosphoryl-methyl)-quinoline (G33~36 or B33~36)

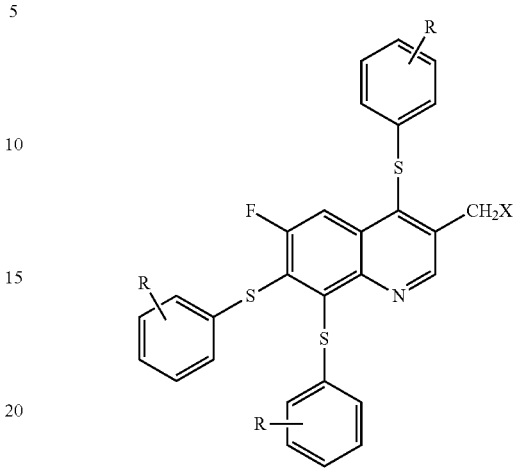

| No | R | X | Formula | Yield % | Mp ° C. |
|---|---|---|---|---|---|
| G33 | H | Br | $C_{28}H_{19}BrFNS_3$ | 86.7 | 150-2 |
| G34 | p-F | Br | $C_{28}H_{16}BrF_4NS_3$ | 90.5 | 141-2 |
| G35 | m-OCH$_3$ | Br | $C_{31}H_{25}BrFNO_3S_3$ | — | — |
| G36 | p-CH(CH$_3$)$_2$ | Br | $C_{37}H_{37}BrFNS_3$ | 82.0 | 135-8 |
| B33 | H | P(O)Ph$_2$ | $C_{40}H_{29}FNOPS_3$ | 86.2 | 238-40 |
| B34 | p-F | P(O)Ph$_2$ | $C_{40}H_{26}F_4NOPS_3$ | 100 | 229-31 |
| B35 | m-OCH$_3$ | P(O)Ph$_2$ | C43H35FNO4PS3 | 69.5* | 178-80 |
| B36 | p-CH(CH$_3$)$_2$ | P(O)Ph$_2$ | $C_{49}H_{47}FNOPS_3$ | 100 | 212-6 |

*two steps' yield

TABLE 30

4,6,7,8-tetrasubstituted thiophenyl-3-bromomethyl(or 3-diphenyl-phosphoryl-methyl)-quinoline (G37~40 or B37~40)

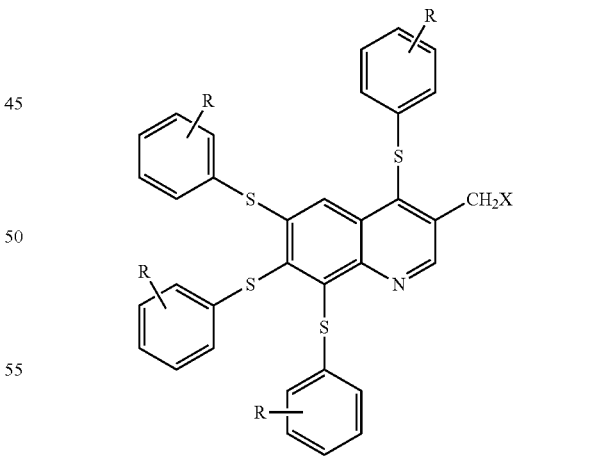

| No | R | X | Formula | Yield % | Mp ° C. |
|---|---|---|---|---|---|
| G37 | H | Br | $C_{34}H_{24}BrNS_4$ | 100 | 139-41 |
| G38 | p-F | Br | $C_{34}H_{20}BrF_4NS_4$ | 87.8 | 173-5 |
| G39 | m-OCH$_3$ | Br | $C_{38}H_{32}BrNO_4S_4$ | — | — |
| G40 | p-CH(CH$_3$)$_2$ | Br | $C_{46}H_{48}BrNS_4$ | — | Oil |
| B37 | H | P(O)Ph$_2$ | $C_{46}H_{34}NOPS_4$ | 95.4 | 222-4 |
| B38 | p-F | P(O)Ph$_2$ | $C_{46}H_{30}F_4NOPS_4$ | 82.8 | 225-7 |

TABLE 30-continued 4,6,7,8-tetrasubstituted thiophenyl-3-bromomethyl(or 3-diphenyl-phosphoryl-methyl)-quinoline (G37~40 or B37~40)

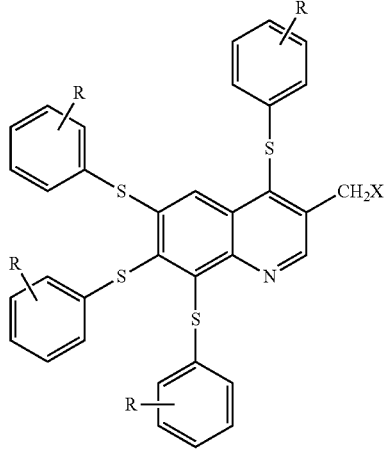

| No | R | X | Formula | Yield % | Mp ° C. |
|---|---|---|---|---|---|
| B39 | m-OCH₃ | P(O)Ph₂ | C₅₀H₄₂NO₅PS₄ | 93.9* | 104-6 |
| B40 | p-CH(CH₃)₂ | P(O)Ph₂ | C₅₈H₅₈NOPS₄ | 78.8 | 160-4 |

*two steps' yield

TABLE 31 tert-butyl (3R, 5S, 6E)-7-(4-substituted thiophenylquinoline-3-yl]-3,5-dihydroxy-3,5-O-isopropylidene-6-heptenoate (D1~4)

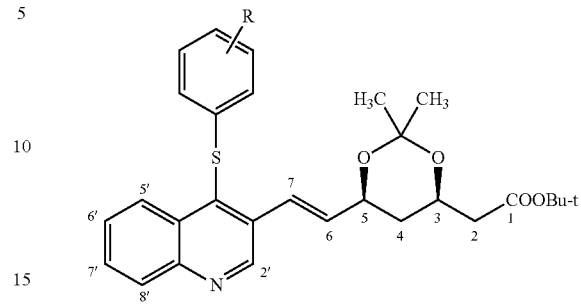

| No | R | Formula | [α]$_D$ | Yield* % | Mp ° C. |
|---|---|---|---|---|---|
| D1 | H | C₃₀H₃₆NO₄S | −9.3, c = 1, CH₂Cl₂ | 29.6 | 135-6 |
| D2 | p-F | C₃₀H₃₅FNO₄S | −9.4, c = 1, CHCl₃ | 26.7 | 110-2 |
| D3 | m-OCH₃ | C₃₁H₃₈NO₅S | −3.4, c = 1, CH₂Cl₂ T = 35° C. | 22.2 | 106-8 |
| D4 | p-CH(CH₃)₂ | C₃₃H₄₂NO₄S | +1.5 c = 0.68, Acetone | 28.5 | 107-8 |

*purified by silica gel chromatography (petroleum ether-EtOAc).

TABLE 32

¹H-NMR data of D1~4 (δ ppm in CDCl₃)

¹H-NMR δ ppm in CDCl₃

| No | 2'H | 8'H | 5'H | 6'H | 7'H | 7H | R (aryl) | 6H | 5H | 3H | 2H | 4H | 2 × CH₃ & t-Bu |
|---|---|---|---|---|---|---|---|---|---|---|---|---|---|
| D1 | 9.13 s | 8.45 d, J = 8.0 | 8.10 d, J = 8.4 | 7.67 t, J = 7.6 | 7.53 t, J = 8.0 | 7.31 d, J = 16.0 | 7.19-7.04 (m, 5H) | 6.32 dd, J = 16.2, 6.0 | 4.56-4.52 m | 4.32-4.30 m | 2.48-2.28 m | 1.62-1.24 (m, 17H) | |
| D2 | 9.10 s | 8.45 dd, J = 8.6, 1.2 | 8.10 d, J = 8.4 | 7.70-7.66 m | 7.57-7.52 m | 7.30 dd, J = 16.2, 0.8 | 7.08-7.05 (m, 2H), 6.90-6.86 (m, 2H) | 6.30 dd, J = 16.4, 6.4 | 4.57-4.53 m | 4.34-4.30 m | 2.49-2.29 m | 1.67-1.62 (m, 1H), 1.34-1.25 (m, 1H) | 1.54-1.44 (m, 15H) |
| D3 | 9.14 s | 8.43 d, J = 8.0 | 8.10 d, J = 8.4 | 7.68 t, J = 6.8 | 7.53 t, J = 8.0 | 7.21 d, J = 16.0 | 7.08 (t, 1H, J = 8.0) 6.66-6.59 (m, 3H) 3.67 (s, 3H) | 6.34 dd, J = 16.4, 6.0 | 4.59-4.54 m | 4.33-4.31 m | 2.48-2.29 m | 1.65-1.64 (m, 1H), 1.35-1.27 (m, 1H) | 1.51-1.43 (m, 15H) |
| D4 | 9.12 s | 8.49-8.47 m | 8.09 d, J = 8.0 | 7.69-7.65 m | 7.55-7.51 m | 7.35 d, J = 16.0 | 7.04-6.98 (m, 4H) 2.82-2.79 (m, 1H), 1.18 (d, 6H, J = 7.2) | 6.32 dd, J = 16.2, 6.4 | 4.57-4.53 m | 4.34-4.30 m | 2.48-2.28 m | 1.67-1.62 (m, 1H), 1.36-1.28 (m, 1H) | 1.51-1.44 (m, 15H) |

TABLE 33

(3R, 5S, 6E)-7-(7-fluoro-4-substituted thiophenylquinoline-3-yl]-3,5-dihydroxy-3,5-O-isopropylidene-6-heptenoate (D5~8)

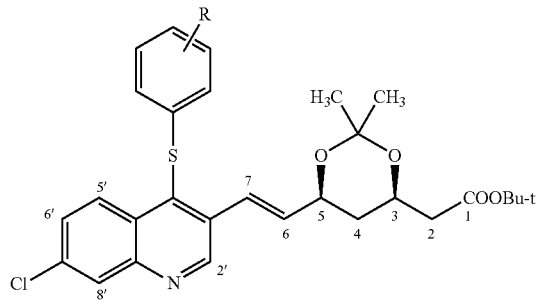

| No | R | Formula | $[\alpha]_D$ | Yield* % | Mp °C. |
|---|---|---|---|---|---|
| D5 | H | $C_{30}H_{35}ClNO_4S$ | +4.9 c = 1, acetone | 31.9 | 130-2 |
| D6 | p-F | $C_{30}H_{34}ClFNO_4S$ | +11.9 c = 1, acetone | 20.3 | 151-3 |
| D7 | m-OCH$_3$ | $C_{31}H_{37}ClNO_5S$ | +7.8 c = 1, acetone | 25.0 | 96-8 |
| D8 | p-CH(CH$_3$)$_2$ | $C_{33}H_{41}ClNO_4S$ | +1.9 c = 1, CH$_2$Cl$_2$ | 33.6 | oil |

TABLE 35

(3R, 5S, 6E)-7-(7-fluoro-6-fluoro-4-substituted thiophenylquinoline-3-yl]-3,5-dihydroxy-3,5-O-isopropylidene-6-heptenoate (D9~12)

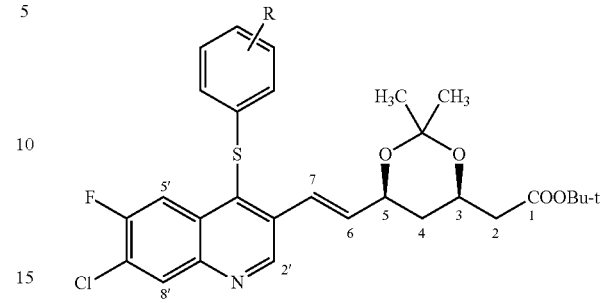

| No | R | Formula | $[\alpha]_D$ | Yield* % | Mp °C. |
|---|---|---|---|---|---|
| D9 | H | $C_{30}H_{34}ClFNO_4S$ | −17.7 c = 1, CHCl$_3$ | 46.5 | 131-3 |
| D10 | p-F | $C_{30}H_{33}ClF_2NO_4S$ | +11.6 c = 1, acetone | 69.5 | 120-1 |
| D11 | m-OCH$_3$ | $C_{31}H_{36}ClFNO_5S$ | −11.3 c = 1, CHCl$_3$ | 60.6 | 83-5 |
| D12 | p-CH(CH$_3$)$_2$ | $C_{33}H_{40}ClFNO_4S$ | +7.1 c = 1.1, acetone | 56.1 | oil |

TABLE 34

$^1$H-NMR data of D5~8 ($\delta$ ppm in CDCl$_3$)

$^1$H-NMR $\delta$ ppm in CDCl$_3$

| No | 2'H | 5'H | 8'H | 6'H | 7H | ⌬R | 6H | 5H | 3H | 2H | 4H | 2 × CH$_3$ & t-Bu |
|---|---|---|---|---|---|---|---|---|---|---|---|---|
| D5 | 9.11 s | 8.38 d, J = 9.2 | 8.09 d, J = 2.0 | 7.46 dd, J = 8.8, 2.0 | 7.28 d, J = 16.8 | 7.20-7.02 (m, 5H) | 6.32 dd, J = 16.4, 5.6 | 4.56-4.51 m | 4.34-4.27 m | 2.47-2.27 m | | 1.63-1.23 m, 17H |
| D6 | 9.09 s | 8.39 d, J = 8.8 | 8.09 d, J = 2.0 | 7.50-7.47 m | 7.26 d, J = 16.4 | 7.08-7.04 (m, 2H) 6.92-6.87 (m, 2H) | 6.30 dd, J = 16.0, 5.6 | 4.57-4.53 m | 4.35-4.29 m | 2.49-2.29 m | | 1.67-1.24 m, 17H |
| D7 | 9.12 s | 8.36 d, J = 9.2 | 8.09 d, J = 1.6 | 7.46 dd, J = 9.2, 2.4 | 7.28 dd, J = 16.0, 0.8 | 7.10-7.06 (m, 1H) 6.68-6.58 (m, 3H) 3.68 (s, 3H) | 6.33 dd, J = 16.2, 6.0 | 4.58-4.53 m | 4.33-4.30 m | 2.48-2.28 m | | 1.65-1.25, m, 17H |
| D8 | 9.09 s | 8.38 d, J = 8.8 | 8.06 d, J = 2.0 | 7.45 dd, J = 9.0, 1.6 | 7.30 d, J = 16.0 | 7.04-6.95 (m, 4H) 2.81-2.78 (m, 1H) 1.16 (d, 6H, J = 6.8) | 6.30 dd, J = 16.0, 5.6 | 4.56-4.52 m | 4.32-4.29 m | 2.46-2.27 m | | 1.65-1.22 m, 17H |

*purified by silica gel chromatography (petroleum ether-EtOAc)

TABLE 36

¹H-NMR data of D9~12 (δ ppm in CDCl₃)
¹H-NMR δ ppm in CDCl₃

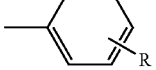

| No | 2'H | 8'H | 5'H | 7H | R | 6H | 5H | 3H | 2H | 4H, 2 × CH₃ & t-Bu |
|---|---|---|---|---|---|---|---|---|---|---|
| D9 | 9.08 s | 8.18-8.14 m | | 7.24 dd, J = 15.8, 1.2 | 7.22-7.12 (m, 3H) 7.05-7.03 (m, 2H) | 6.34 dd, J = 16.4, 5.6 | 4.56-4.52 m | 4.33-4.28 m | 2.47-2.27 m | 1.64-1.23 m, 17H |
| D10 | 9.06 s | 8.18-8.16 m | | 7.28 d, J = 15.2 | 7.09-7.05 (m, 2H) 6.91-6.89 (m, 2H) | 6.33 dd, J = 16.4, 5.2 | 4.57-4.53 m | 4.34-4.31 m | 2.49-2.29 m | 1.67-1.26 m, 17H |
| D11 | 9.08 s | 8.17-8.13 m | | 7.24 dd, J = 17.2, 0.8 | 7.10 (t, 1H, J = 8.4) 6.70-6.58 (m, 3H) 3.69 (s, 3H) | 6.35 dd, J = 16.4, 6.0 | 4.58-4.54 m | 4.33-4.29 m | 2.48-2.28 m | 1.66-1.24 m, 17H |
| D12 | 9.07 s | 8.18-8.14 m | | 7.31 d, J = 16.4 | 7.06-6.97 (m, 4H) 2.83-2.80 (m, 1H) 1.18 (d, 6H, J = 6.8) | 6.35 dd, J = 16.4, 5.6 | 4.58-4.54 m | 4.33-4.31 m | 2.48-2.28 m | 1.66-1.24 m, 17H |

*purified by silica gel chromatography (petroleum ether-EtOAc).

TABLE 37

(3R, 5S, 6E)-7-(6,7,8-trifluoro-4-substituted thiophenylquinoline-3-yl]-3,5-dihydroxy-3,5-O-isopropylidene-6-heptenoate (D13~16)

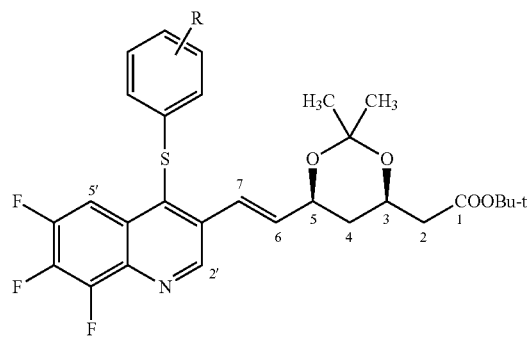

| No | R | Formula | [α]_D | Yield* % | Mp °C. |
|---|---|---|---|---|---|
| D13 | H | C₃₀H₃₃F₃NO₄S | +5.9 c = 1, acetone | 55.8 | 169-71 |
| D14 | p-F | C₃₀H₃₂F₄NO₄S | +15.4 c = 1, THF | 70.8 | 126-8 |

TABLE 37-continued (3R, 5S, 6E)-7-(6,7,8-trifluoro-4-substituted thiophenylquinoline-3-yl]-3,5-dihydroxy-3,5-O-isopropylidene-6-heptenoate (D13~16)

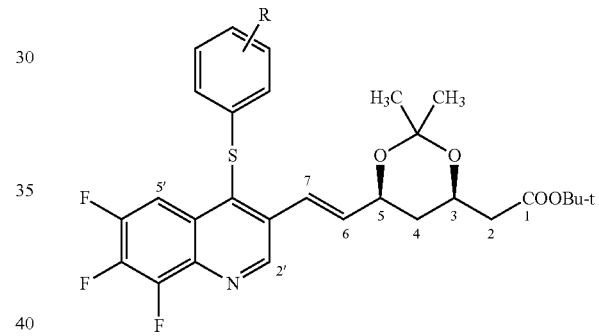

| No | R | Formula | [α]_D | Yield* % | Mp °C. |
|---|---|---|---|---|---|
| D15 | m-OCH₃ | C₃₁H₃₅F₃NO₅S | +11.4 c = 1, acetone | 21.8 | 132-4 |
| D16 | p-CH(CH₃)₂ | C₃₃H₃₉F₃NO₄S | +7.5 c = 0.32, acetone | 58.3 | 94-96 |

*purified by silica gel chromatography (petroleum ether-EtOAc)

TABLE 38

¹H-NMR data of D13~16 (δ ppm in CDCl₃)
¹H-NMR δ ppm in CDCl₃

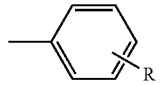

| No | 2'H | 5'H | 7H | R | 6H | 5H | 3H | 2H | 4H 2 × CH₃ & t-Bu |
|---|---|---|---|---|---|---|---|---|---|
| D13 | 9.11 s | 8.07-8.04 m | 7.29-7.15 (m, 4H), | 7.05-7.03 (m, 2H) | 6.34 dd, J = 16.8, 6.0 | 4.56-4.52 m | 4.32-4.29 m | 2.47-2.27 m | 1.64-1.21 m, 17H |
| D14 | 9.07 s | 8.07-8.02 m | 7.24 d, J = 16.0 | 7.07-7.04 (m, 2H), 6.93-6.88 (m, 2H) | 6.30 dd, J = 16.0, 5.6 | 4.56-4.52 m | 4.33-4.28 m | 2.47-2.27 m | 1.66-1.19, m, 17H |

TABLE 38-continued

¹H-NMR data of D13~16 (δ ppm in CDCl₃)

¹H-NMR δ ppm in CDCl₃

| No | 2'H | 5'H | 7H | (aryl-R) | 6H | 5H | 3H | 2H | 4H | 2 × CH₃ & t-Bu |
|---|---|---|---|---|---|---|---|---|---|---|
| D15 | 9.11 s | 8.06-8.00 m | 7.27 d, J = 16.0 | 7.10 (t, 1H, J = 8.0) 6.71-6.58 (m, 1H), 6.60-6.58 (m, 2H) 3.70 (s, 3H) | 6.36 dd, J = 16.4, 5.6 | 4.58-4.54 m | 4.34-4.28 m | 2.48-2.28 m | | 1.66-1.23, m, 17H |
| D16 | 9.11 s | 8.09-8.04 m | 7.31 dd, J = 16.4, 1.2 | 7.08-6.98 (m, 4H) 2.84-2.81 (m, 1H) 1.19 (d, 6H, J = 6.8) | 6.34 dd, J = 16.0, 5.6 | 4.58-4.54 m | 4.33-4.30 m | 2.48-2.28 m | | 1.68-1.25 m, 17H |

TABLE 39

(3R, 5S, 6E)-7-(4,7-disubstituted thiophenylquinoline-3-yl]-3,5-dihydroxy-3,5-O-isopropylidene-6-heptenoate (D17~20)

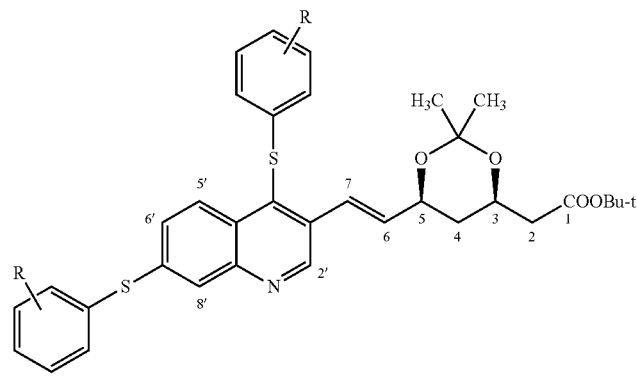

| No | R | Formula | [α]_D | Yield* % | Mp ° C. |
|---|---|---|---|---|---|
| D17 | H | C₃₆H₄₀NO₄S₂ | +0.8 c = 1, THF | 26.2 | 109-10 |
| D18 | p-F | C₃₆H₃₈F₂NO₄S₂ | +6.4 c = 0.7, acetone | 45.7 | 155-7 |
| D19 | m-OCH₃ | C₃₈H₄₄NO₆S₂ | −3.6 c = 1, CH₂Cl₂ | 52.8 | oil |
| D20 | p-CH(CH₃)₂ | C₄₂H₅₂NO₄S₂ | −10.2 c = 0.84, CH₂Cl₂ | 21.7 | 107-8 |

*purified by silica gel chromatography (petroleum ether-EtOAc).

TABLE 40

¹H-NMR data of D17~20 (δ ppm in CDCl₃)

¹H-NMR δ ppm in CDCl₃

| No | 2'H | 5'H | 8'H | 6'H | 7H | (aryl-R) | 6H | 5H | 3H | 2H | 4H | 2 × CH₃ & t-Bu |
|---|---|---|---|---|---|---|---|---|---|---|---|---|
| D17 | 9.05 s | 8.32 d, J = 9.2 | 7.81 d, J = 1.6 | 7.54 dd, J = 6.6, 1.6 | | 7.39-7.36 (m, 4H) 7.29-7.25 (m, 2H) 7.19-7.03 (m, 5H) | 6.29 dd, J = 16.2, 6.0 | 4.55-4.51 m | 4.32-4.29 m | 2.47-2.28 m | | 1.62-1.24 m, 17H |
| D18 | 9.01 s | 8.32 d, J = 8.8 | 7.70 d, J = 1.6 | 7.34 dd, J = 10.0, 1.6 | 7.24 d, J = 16.4 | 7.56-7.52 (m, 2H) 7.12-7.02 (m, 4H) 6.90-6.86 (m, 2H) | 6.26 dd, J = 16.4, 6.0 | 4.55-4.51 m | 4.32-4.29 m | 2.48-2.28 m | | 1.65-1.23 m, 17H |
| D19 | 9.05 s | 8.30 d, J = 8.8 | 7.84 d, J = 1.2 | 7.46 dd, J = 9.0, 2.0 | | 7.30-7.24 (m, 2H) 7.11-7.05 (m, 3H) 6.91-6.88 (m, 1H), 6.66-6.59 (m, 3H) 3.77 (s, 3H), 3.67 (s, 3H) | 6.30 dd, J = 16.0, 5.6 | 4.56-4.52 m | 4.32-4.29 m | 2.47-2.27 m | | 1.64-1.25, m, 17H |

TABLE 40-continued

¹H-NMR data of D17~20 (δ ppm in CDCl₃)
¹H-NMR δ ppm in CDCl₃

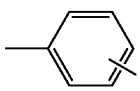

| No | 2'H | 5'H | 8'H | 6'H | 7H | (aryl-R) | 6H | 5H | 3H | 2H | 4H | 2 × CH₃ & t-Bu |
|---|---|---|---|---|---|---|---|---|---|---|---|---|
| D20 | 9.05 s | 8.36 d, J = 8.8 | 7.77 d, J = 1.6 | 7.38 dd, J = 9.0, 1.6 | | 7.51-7.49 (m, 2H), 7.30-7.28 (m, 3H), 7.07-7.00 (m, 4H), 2.98-2.95 (m, 1H), 2.85-2.82 (m, 1H), 1.31 (d, 6H, J = 6.8), 1.21 (d, 6H, J = 7.2) | 6.30 dd, J = 16.2, 5.6 | 4.58-4.54 m | 4.35-4.32 m | 2.49-2.30 m | | 1.67-1.35 m, 17H |

TABLE 41

(3R, 5S, 6E)-7-(6-fluoro-4,7-disubstituted thiophenylquinoline-3-yl]-3,5-dihydroxy-3,5-O-isopropylidene-6-heptenoate (D21~24)

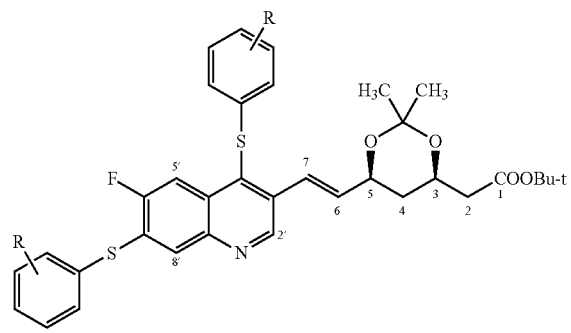

| No | R | Formula | [α]_D | Yield* % | Mp ° C. |
|---|---|---|---|---|---|
| D21 | H | C₃₆H₃₉FNO₄S₂ | +1.2 c = 1, acetone | 67.4 | oil |
| D22 | p-F | C₃₆H₃₇F₃NO₄S₂ | +5.3 c = 0.88, acetone | 35.6 | 106-8 |
| D23 | m-OCH₃ | C₃₈H₄₃FNO₆S₂ | −2.4 c = 1, acetone | 59.3 | 123-5 |
| D24 | p-CH(CH₃)₂ | C₄₂H₅₁FNO₄S₂ | −6.1 c = 1., CH₂Cl₂ | 45.4 | 94-5 |

*purified by silica gel chromatography (petroleum ether-EtOAc)

TABLE 42

¹H-NMR data of D21~24 (δ ppm in CDCl₃)
¹H-NMR δ ppm in CDCl₃

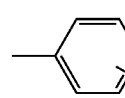

| No | 2'H | 5'H | 8'H | 7H | (aryl-R) | 6H | 5H | 3H | 2H | 4H | 2 × CH₃ & t-Bu |
|---|---|---|---|---|---|---|---|---|---|---|---|
| D21 | 8.97 s | 8.05 d, J = 10.8 | 7.60 d, J = 7.2 | 7.23 dd, J = 16.4, 1.2 | 7.58-7.55 (m, 2H), 7.44-7.40 (m, 3H), 7.21-7.11 (m, 3H), 7.05-7.03 (m, 2H) | 6.29 dd, J = 16.4, 6.0 | 4.55-4.50 m | 4.31-4.28 m | 2.47-2.26 m | | 1.62-1.20 m, 17H |
| D22 | 8.94 s | 8.05 d, J = 11.2 | | 7.59-7.50 (m, 3H), 7.25-7.04 (m, 5H), 6.93-6.88 (m, 2H) | | 6.27 dd, J = 16.4, 5.6 | 4.55-4.51 m | 4.32-4.29 m | 2.48-2.28 m | | 1.65-1.25 m, 17H |
| D23 | 8.98 s | 8.04 d, J = 11.2 | 7.65 d, J = 7.6 | 7.35-7.30 (m, 1H), 7.27-7.23 (m, 1H), 7.14-7.07 (m, 3H), 6.96-6.93 (m, 1H), 6.68-6.59 (m, 3H), 3.79 (s, 3H), 3.69 (s, 3H) | | 6.30 dd, J = 16.0, 5.6 | 4.56-4.52 m | 4.32-4.29 m | 2.47-2.27 m | | 1.63-1.20 m, 17H |

TABLE 42-continued $^1$H-NMR data of D21~24 (δ ppm in CDCl$_3$)

$^1$H-NMR δ ppm in CDCl$_3$

| No | 2'H | 5'H | 8'H | 7H | ⟨—⟩R | 6H | 5H | 3H | 2H | 4H | 2 × CH$_3$ & t-Bu |
|---|---|---|---|---|---|---|---|---|---|---|---|
| D24 | 8.95 s | 8.05 d, J = 11.6 | | | 7.53-7.49 (m, 3H), 7.30-7.25 (m, 3H), 7.05-6.96 (m, 4H), 2.96-2.93 (m, 1H), 2.82-2.79 (m, 1H), 1.28 (d, 6H, J = 6.8), 1.17 (d, 6H, J = 7.2) | 6.33 dd, J = 16.0, 5.6 | 4.55-4.51 m | 4.31-4.27 m | 2.46-2.26 m | | 1.64-1.41 m, 17H |

TABLE 43

(3R, 5S, 6E)-7-(6,8-difluoro-4,7-disubstituted thiophenylquinoline-3-yl]-3,5-dihydroxy-3,5-O-isopropylidene-6-heptenoate (D25~28)

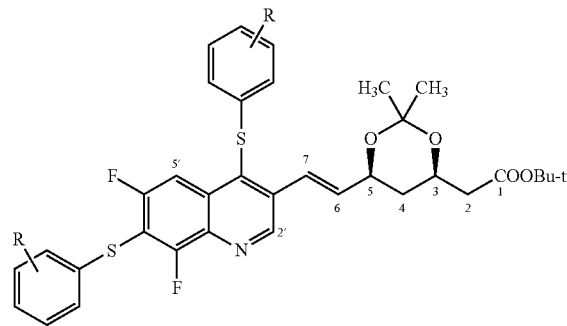

| No | R | Formula | [α]$_D$ | Yield* % | Mp ° C. |
|---|---|---|---|---|---|
| D25 | H | C$_{36}$H$_{38}$F$_2$NO$_4$S$_2$ | −1.8 c = 1, CH$_2$Cl$_2$ | 20.5 | 178-80 |
| D26 | p-F | C$_{36}$H$_{36}$F$_4$NO$_4$S$_2$ | +7.6 c = 1, CH$_2$Cl$_2$ | 47.5 | 167-70 |

TABLE 43-continued (3R, 5S, 6E)-7-(6,8-difluoro-4,7-disubstituted thiophenylquinoline-3-yl]-3,5-dihydroxy-3,5-O-isopropylidene-6-heptenoate (D25~28)

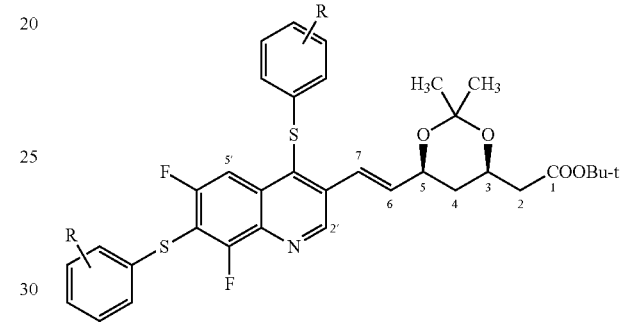

| No | R | Formula | [α]$_D$ | Yield* % | Mp ° C. |
|---|---|---|---|---|---|
| D27 | m-OCH$_3$ | C$_{38}$H$_{42}$F$_2$NO$_6$S$_2$ | +9.7 c = 0.78, acetone | 52.9 | 119-21 |
| D28 | p-CH(CH$_3$)$_2$ | C$_{42}$H$_{50}$F$_2$NO$_4$S$_2$ | +10.4 c = 1, THF | 42.6 | 107-8 |

*purified by silica gel chromatography (petroleum ether-EtOAc)

TABLE 44

$^1$H-NMR data of D25~28 (δ ppm in CDCl$_3$)

$^1$H-NMR δ ppm in CDCl$_3$

| No | 2'H | 5'H | 7H | ⟨—⟩R | 6H | 5H | 3H | 2H | 4H | 2 × CH$_3$ & t-Bu |
|---|---|---|---|---|---|---|---|---|---|---|
| D25 | 9.09 s | 7.97 dd J = 10.0, 1.2 | 7.39-7.37 (m, 3H), 7.29-7.15 (m, 6H) 7.07-7.05 (m, 2H) | | 6.36 dd, J = 16.4, 5.6 | 4.56-4.53 m | 4.31-4.29 m | 2.47-2.27 m | | 1.62-1.23 m, 17H |
| D26 | 9.03 s | 7.96 dd J = 10.4, 2.0 | 7.25 dd, J = 16.4, 1.2 | 7.47-7.43 (m, 2H) 7.09-7.06 (m, 2H) 6.99-6.89 (m, 4H) | 6.34 dd, J = 16.0, 5.6 | 4.57-4.53 m | 4.33-4.30 m | 2.49-2.28 m | | 1.67-1.23 m, 17H |
| D27 | 9.10 s | 7.95 dd J = 10.4, 2.0 | 7.27 d, J = 16.0 | 7.17-7.09 (m, 2H), 6.93-6.89 (m, 2H) 6.76-6.60 (m, 4H) 3.73 (s, 3H), 3.69 (s, 3H) | 6.38 dd, J = 16.4, 5.6 | 4.58-4.54 m | 4.32-4.29 m | 2.47-2.28 m | | 1.65-1.22, m, 17H |

TABLE 44-continued

¹H-NMR data of D25~28 (δ ppm in CDCl₃)
¹H-NMR δ ppm in CDCl₃

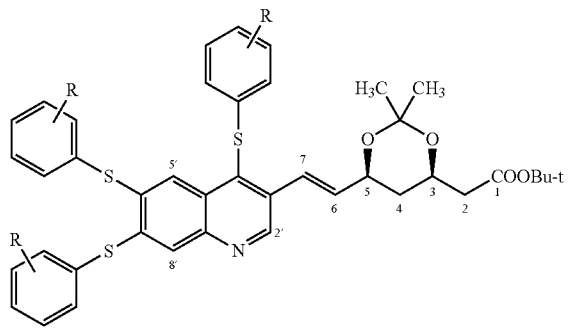

| No | 2'H | 5'H | 7H | | 6H | 5H | 3H | 2H | 2 × CH₃ 4H & t-Bu |
|---|---|---|---|---|---|---|---|---|---|
| D28 | 9.08 s | 7.98 dd J = 10.0, 1.2 | 7.36-7.29 (m, 3H), 7.13-6.99 (m, 6H), 2.87-2.81 (m, 2H), 1.22-1.19 (m, 12H) | | 6.36 dd, J = 16.0, 5.6 | 4.58-4.54 m | 4.34-4.30 m | 2.48-2.28 m | 1.68-1.25 m, 17H |

TABLE 45

(3R, 5S, 6E)-7-(4,7,6-trisubstituted thiophenylquinoline-3-yl]-3,5-dihydroxy-3,5-O-isopropylidene-6-heptenoate (D29~32)

| No | R | Formula | [α]_D | Yield* % | Mp °C. |
|---|---|---|---|---|---|
| D29 | H | C₄₂H₄₄NO₄S₃ | −10.2 c = 1.0 CH₂Cl₂ | 80.4 | 138-40 |
| D30 | p-F | C₄₂H₄₁F₃NO₄S₃ | +4.2 c = 1, acetone | 29.4 | 158-60 |
| D31 | m-OCH₃ | C₄₅H₅₀NO₇S₃ | −7.6 c = 1.04 CH₂Cl₂ | 58.6 | oil |
| D32 | p-CH(CH₃)₂ | C₅₁H₆₂NO₄S₃ | −8.3 c = 0.86 CH₂Cl₂ | 36.6 | 110-1 |

*purified by silica gel chromatography (petroleum ether-EtOAc)

TABLE 46

¹H-NMR data of D29~32 (δ ppm in CDCl₃)
¹H-NMR δ ppm in CDCl₃

| No | 2'H | 5'H | 8'H | 7H | | 6H | 5H | 3H | 2H | 2 × CH₃ 4H & t-Bu |
|---|---|---|---|---|---|---|---|---|---|---|
| D29 | 8.95 s | 8.13 s | 7.57 s | 7.54-7.52 (m, 2H), 7.43-7.39 (m, 3H), 7.32-7.24 (m, 6H), 7.14-7.09 (m, 3H), 6.86-6.84 (m, 2H) | | 6.27 dd J = 16.0, 5.6 | 4.55-4.50 m | 4.31-4.28 m | 2.46-2.26 m | 1.64-1.25 m, 17H |
| D30 | 8.95 s | 7.98 s | 7.50 s | 7.56-7.51 (m, 2H), 7.36-7.32 (m, 2H), 7.28-7.23 (m, 3H), 7.15-7.11 (m, 2H), 7.04-7.00 (m, 2H), 6.86-6.84 (m, 2H) | | 6.29 dd J = 16.0, 5.6 | 4.57-4.53 m | 4.33-4.30 m | 2.48-2.28 m | 1.69-1.28 m, 17H |
| D31 | 8.96 s | 8.18 s | 7.63 s | 7.33-6.82 (m, 10H), 6.63-6.60 (m, 1H), 6.44-6.40 (m, 2H), 3.77 (s, 3H), 3.70 (s, 3H), 3.65 (s, 3H) | | 6.28 dd J = 16.4, 6.0 | 4.55-4.51 m | 4.31-4.28 m | 2.46-2.27 m | 1.64-1.22 m, 17H |

TABLE 46-continued $^1$H-NMR data of D29~32 (δ ppm in CDCl$_3$)
$^1$H-NMR δ ppm in CDCl$_3$

| No | 2'H | 5'H | 8'H | 7H | ⟨Ar⟩-R | 6H | 5H | 3H | 2H | 4H | 2 × CH$_3$ & t-Bu |
|---|---|---|---|---|---|---|---|---|---|---|---|
| D32 | 8.91 s | 8.04 s | 7.53 s | 7.49 (d, 2H, J = 8.0), 7.32-7.25 (m, 5H), 7.19 (d, 2H, J = 8.4), 6.99 (d, 2H, J = 8.8), 6.76 (d, 2H, J = 8.0), 2.98-2.91 (m, 2H), 2.82-2.46 (m, 1H), 1.31-1.19 (m, 18H) | | 6.25 dd, J = 16.0, 5.6 | 4.56-4.52 m | 4.32-4.29 m | 2.46-2.27 m | | 1.66-1.34 m, 17H |

TABLE 47

(3R, 5S, 6E)-7-(6-fluoro-4,7,8-trisubstituted thiophenylquinoline-3-yl]-3,5-dihydroxy-3,5-O-isopropylidene-6-heptenoate (D33~36)

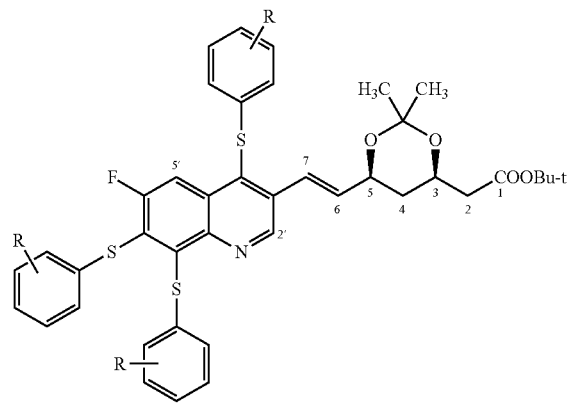

| No | R | Formula | [α]$_D$ | Yield* % | Mp ° C. |
|---|---|---|---|---|---|
| D33 | H | C$_{34}$H$_{26}$FNO$_3$S$_3$ | −0.8 c = 1, CH$_2$Cl$_2$ | 59.2 | 159-61 |
| D34 | p-F | C$_{42}$H$_{40}$F$_4$NO$_4$S$_3$ | +9.2 c = 1, acetone | 60.2 | 194-6 |
| D35 | m-OCH$_3$ | C$_{45}$H$_{49}$FNO$_7$S$_3$ | +10.0 c = 1, acetone | 80.0 | oil |
| D36 | p-CH(CH$_3$)$_2$ | C$_{51}$H$_{61}$FNO$_4$S$_3$ | +2.9 c = 1, acetone | 57.3 | 111-2 |

*purified by silica gel chromatography (petroleum ether-EtOAc).

TABLE 48

$^1$H-NMR data of D33~36 (δ ppm in CDCl$_3$)
$^1$H-NMR δ ppm in CDCl$_3$

| No | 2'H | 5'H | 7H | ⟨Ar⟩-R | 6H | 5H | 3H | 2H | 4H | 2 × CH$_3$ & t-Bu |
|---|---|---|---|---|---|---|---|---|---|---|
| D33 | 9.13 s | 8.19 d J = 10.8 | | 7.27-7.06 (m, 16H) | 6.33 dd, J = 16.0, 5.6 | 4.54-4.50 m | 4.32-4.28 m | 2.47-2.27 m | | 1.61-1.18 m, 17H |
| D34 | 9.10 s | 8.17 d, J = 10.4 | | 7.27-7.19 (m, 5H), 7.10-7.05 (m, 2H), 6.94-6.86 (m, 6H) | 6.31 dd, J = 16.0, 5.2 | 4.54-4.53 m | 4.33-4.29 m | 2.48-2.28 m | | 1.65-1.19 m, 17H |
| D35 | 9.13 s | 8.18 d, J = 10.4 | 7.25 dd J = 16.4, 1.2 | 7.13-7.03 (m, 3H), 6.80-6.58 (m, 9H), 3.70-3.67 (m, 9H) | 6.44 dd, J = 16.4, 6.0 | 4.56-4.52 m | 4.31-4.28 m | 2.47-2.27 m | | 1.64-1.20, m, 17H |

TABLE 48-continued $^1$H-NMR data of D33~36 (δ ppm in CDCl$_3$)
$^1$H-NMR δ ppm in CDCl$_3$

| No | 2'H | 5'H | 7H | | 6H | 5H | 3H | 2H | 2 × CH$_3$<br>4H   & t-Bu |
|---|---|---|---|---|---|---|---|---|---|
| D36 | 9.13<br>s | 8.17<br>d,<br>J = 10.4 | 7.28<br>d,<br>J = 16.0 | 7.13 (t, 4H, J = 8.4)<br>7.07-6.99 (m, 8H)<br>2.86-2.79 (m, 3H)<br>1.20-1.18 (m, 18H) | 6.32<br>dd,<br>J = 16.4,<br>6.0 | 4.56-4.51<br>m | 4.32-4.29<br>m | 2.47-2.27<br>m | 1.65-1.22<br>m, 17H |

TABLE 49

(3R, 5S, 6E)-7-(4,6,7,8-tetrasubstituted
thiophenylquinoline-3-yl]-3,5-dihydroxy-3,5-O-isopropylidene-
6-heptenoate (D37~40)

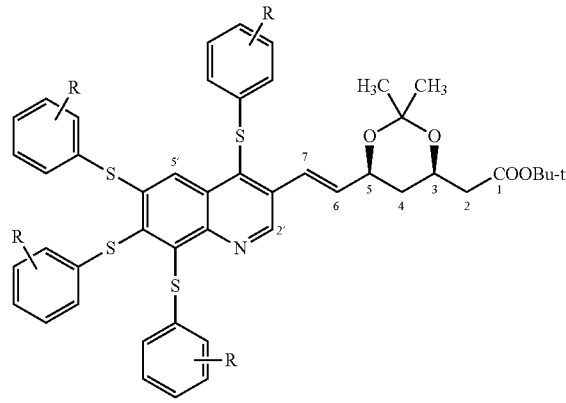

| No | R | Formula | [α]$_D$ | Yield*<br>% | Mp<br>° C. |
|---|---|---|---|---|---|
| D37 | H | C$_{48}$H$_{48}$NO$_4$S$_4$ | +2.7<br>c = 1,<br>THF | 38.1 | 160-2 |
| D38 | p-F | C$_{48}$H$_{44}$F$_4$NO$_4$S$_4$ | +8.4<br>c = 1,<br>acetone | 35.5 | 169-71 |

TABLE 49-continued (3R, 5S, 6E)-7-(4,6,7,8-tetrasubstituted
thiophenylquinoline-3-yl]-3,5-dihydroxy-3,5-O-isopropylidene-
6-heptenoate (D37~40)

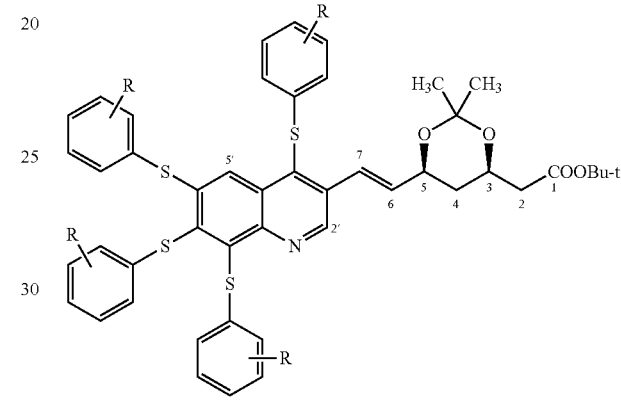

| No | R | Formula | [α]$_D$ | Yield*<br>% | Mp<br>° C. |
|---|---|---|---|---|---|
| D39 | m-OCH$_3$ | C$_{52}$H$_{56}$NO$_8$S$_4$ | +10.4<br>c = 1,<br>acetone | 76.7 | oil |
| D40 | p-CH(CH$_3$)$_2$ | C$_{60}$H$_{72}$NO$_4$S$_4$ | +6.9<br>c = 1,<br>acetone | 70.9 | 144-6 |

*purified by silica gel chromatography (petroleum ether-EtOAc)

TABLE 50

$^1$H-NMR data of D37~40 (δ ppm in CDCl$_3$)
$^1$H-NMR δ ppm in CDCl$_3$

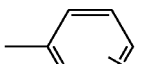

| No | 2'H | 5'H | 7H | | 6H | 5H | 3H | 2H | 2 × CH$_3$<br>4H   & t-Bu |
|---|---|---|---|---|---|---|---|---|---|
| D37 | 9.00<br>s | 7.87<br>s | | 7.42-7.02 (m, 19H),<br>6.74-6.72 (m, 2H) | 6.28<br>dd,<br>J = 16.4,<br>6.0 | 4.54-4.49<br>m | 4.30-4.287<br>m | 2.46-2.26<br>m | 1.63-1.22<br>m, 17H |
| D38 | 8.99<br>s | 7.71<br>s | | 7.40-7.37 (m, 2H), 7.25-7.03 (m, 6H),<br>6.93-6.79 (m, 7H), 6.73-6.69 (m, 2H) | 6.30<br>dd,<br>J = 16.4,<br>6.0 | 4.56-4.52<br>m | 4.31-4.28<br>m | 2.47-2.27<br>m | 1.67-1.24<br>m, 17H |
| D39 | 8.94<br>s | 8.03<br>s | | 7.39-7.29 (m, 3H), 7.17-6.96 (m, 6H),<br>6.75-6.55 (m, 8H), 3.80-3.63 (m, 9H),<br>2.07 (s, 3H) | 6.32<br>dd,<br>J = 16.4,<br>5.6 | 4.65-4.61<br>m | 4.36-4.33<br>m | 2.50-2.31<br>m | 1.77-1.23,<br>m, 17H |

TABLE 50-continued $^1$H-NMR data of D37~40 (δ ppm in CDCl$_3$)

$^1$H-NMR δ ppm in CDCl$_3$

| No | 2'H | 5'H | 7H | 6H | 5H | 3H | 2H | 4H | 2 × CH$_3$ & t-Bu |
|---|---|---|---|---|---|---|---|---|---|
| D40 | 8.99 s | 7.84 s | 7.32-7.21 (m, 6H), 7.14-7.11 (m, 2H), 7.05-6.94 (m, 7H), 6.67-6.65 (m, 2H), 2.97-2.94 (m, 1H), 2.85-2.76 (m, 3H), 1.30-1.14 (m, 24H) | 6.28 dd, J = 16.0, 6.0 | 4.54-4.52 m | 4.31-4.28 m | 2.47-2.27 m | | 1.65-1.34. m, 17H |

TABLE 51

(4R, 6S)-6-[(E)-2-(4-substituted thiophenylquinoline-3-yl)-ethenyl]-3,4,5,6-tetrahydro-4-hydroxy-2H-pyran-2-one (A1~4)

| No | R | Formula | [α]$_D$ | Yield* (%) | Mp (° C.) | MS EI$^+$ (M + 1) |
|---|---|---|---|---|---|---|
| A1 | H | C$_{22}$H$_{19}$NO$_3$S | +26.7, c = 0.94, CH$_2$Cl$_2$ | 91.7 | 102-4 | 378 |
| A2 | p-F | C$_{22}$H$_{18}$FNO$_3$S | +28.9, c = 0.47, CH$_2$Cl$_2$ | 82.2 | 130-2 | 396 |
| A3 | m-OCH$_3$ | C$_{23}$H$_{21}$NO$_4$S | +24.2, c = 0.88, CH$_2$Cl$_2$ | 95.6 | 132-5 | 408 |
| A4 | p-CH(CH$_3$)$_2$ | C$_{25}$H$_{25}$NO$_3$S | +28.9, c = 0.84, CH$_2$Cl$_2$ | 37.8 | 147-8 | 420 |

*purified by silica gel chromatography (petroleum ether-EtOAc).

TABLE 52

$^1$H-NMR data of A1~4 (δ ppm in CDCl$_3$)

| No | 2″H | 8″H | 5″H | 6″H | 7″H | 2'H | R (phenyl) | 1'H | 6H | 4H | 3H | 5H |
|---|---|---|---|---|---|---|---|---|---|---|---|---|
| A1 | 9.29 s | 8.38 d, J = 8.4 | 8.09 d, J = 7.6 | 7.80-7.75 m | 7.67-7.63 m | 7.32, dd, J = 16.4, 1.2 | 7.24 (t, 2H, J = 7.6), 7.17 (t, 1H, J = 7.2) 7.08-7.06 (m, 2H) | 6.75, dd, J = 16.0, 6.0 | 5.31-5.26 m | 4.15-4.12 m | 2.71-2.42 m | 1.95-1.77 m |
| A2 | 9.08 s | 8.46, d, J = 8.0 | 8.11 d, J = 8.4 | 7.73-7.69 m | 7.76, t, J = 7.2 | 7.40 dd, J = 16.2, 1.2 | 7.08-7.04 (m, 2H), 6.91-6.87 (m, 2H) | 6.34, dd, J = 16.0, 6.0 | 5.38-5.34 m | 4.42-4.39 m | 2.80-2.63 m | 2.07-1.83 m |

TABLE 52-continued

¹H-NMR data of A1~4 (δ ppm in CDCl₃)

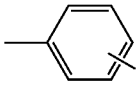

| No | 2"H | 8"H | 5"H | 6"H | 7"H | 2'H | R | 1'H | 6H | 4H | 3H | 5H |
|---|---|---|---|---|---|---|---|---|---|---|---|---|
| A3 | 9.09 s | 8.47, d, J = 8.4 | 8.11, d, J = 8.8 | 7.71, t, J = 7.6 | 7.56, t, J = 8.0 | 7.37, d, J = 16.4 | 7.07 (t, 1H, J = 8.0), 6.67-6.57 (m, 3H), 3.68 (s, 3H) | 6.34, dd, J = 16.2, 5.6 | 5.36-5.33 m | 4.35-4.33 m | 2.77-2.61 m | 2.03-1.82 m |
| A4 | 9.09 s | 8.51, d, J = 8.4 | 8.12, d, J = 8.0 | 7.71, t, J = 8.0 | 7.56, t, J = 8.0 | 7.41, d, J = 16.8 | 7.06-7.00 (m, 4H), 2.85-2.74 (m, 1H), 1.18 (d, 6H, J = 6.8) | 6.33, dd, J = 16.4, 6.0 | 5.34 s | 4.36 s | 2.72-2.63 m | 2.02-1.82 m |

TABLE 53

(4R, 6S)-6-[(E)-2-(7-chloro-4-substituted thiophenylquinoline-3-yl)-ethenyl]-3,4,5,6-tetrahydro-4-hydroxy-2H-pyran-2-one (A5~8)

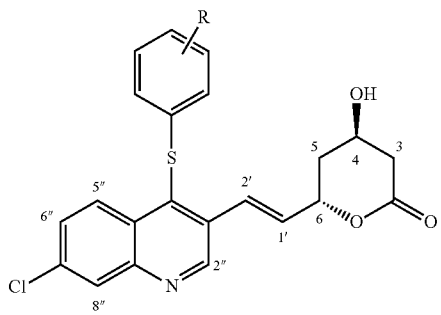

| No | R | Formula | [α]_D | Yield* (%) | Mp (° C.) | MS EI⁺ (M + 1) |
|---|---|---|---|---|---|---|
| A5 | H | C₂₂H₁₈ClNO₃S | +25.0, c = 1, CH₂Cl₂ | 48.7 | 158-9 | 412 |
| A6 | p-F | C₂₂H₁₇ClFNO₃S | +21.1, c = 1, CH₂Cl₂ | 48.7 | 179-81 | 430 |
| A7 | m-OCH₃ | C₂₃H₂₀ClNO₄S | +22.3, c = 1, CH₂Cl₂ | 57.5 | 140-2 | 442 |
| A8 | p-CH(CH₃)₂ | C₂₅H₂₄ClNO₃S | +14.1, c = 1, CH₂Cl₂ | 41.0 | 170 | 454 |

*purified by silica gel chromatography (petroleum ether-EtOAc)

TABLE 54

¹H-NMR data of A5~8 (δ ppm in CDCl₃)

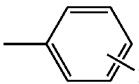

| No | 2"H | 5"H | 8"H | 6"H | 2'H | R | 1'H | 6H | 4H | 3H | 5H |
|---|---|---|---|---|---|---|---|---|---|---|---|
| A5 | 9.07 s | 8.38, d, J = 9.2 | 8.09, d, J = 2.0 | 7.48, dd, J = 9.2, 2.4 | 7.34, dd, J = 16.4, 1.6 | 7.20-7.01 (m, 5H) | 6.34, dd, J = 16.4, 6.0 | 5.37-5.32 m | 4.37-4.33 m | 2.76-2.62 m | 2.05-1.78 m |
| A6 | 9.06 s | 8.38, d, J = 8.8 | 8.09, d, J = 2.0 | 7.50, dd, J = 9.2, 2.0 | 7.37, dd, J = 16.0, 0.8 | 7.07-7.03 (m, 2H) 6.93-6.88 (m, 2H) | 6.34, dd, J = 15.8, 5.6 | 5.39-5.34 m | 4.42-4.38 m | 2.79-2.64 m | 2.09-1.81 m |

TABLE 54-continued

¹H-NMR data of A5~8 (δ ppm in CDCl₃)

| No | 2"H | 5"H | 8"H | 6"H | 2'H | —⟨phenyl⟩—R | 1'H | 6H | 4H | 3H | 5H |
|---|---|---|---|---|---|---|---|---|---|---|---|
| A7 | 9.07 s | 8.38, d, J = 9.2 | 8.09, d J = 1.6 | 7.49, dd, J = 9.2, 2.0 | 7.34, dd, J = 16.0, 0.8 | 7.08 (t, 1H, J = 8.0) 6.68-6.55 (m, 3H), 3.69 (s, 3H) | 6.34, dd, J = 16.4, 6.0 | 5.37-5.32 m | 4.34-4.32 m | 2.76-2.62 m | 2.05-1.79 m |
| A8 | 9.07 s | 8.42, d, J = 8.8 | 8.10, d, J = 2.0 | 7.49, dd, J = 8.8, 2.0 | 7.37, dd, J = 16.0, 0.8 | 7.06-6.96 (m, 4H), 2.85-2.80 (m, 1H) 1.18 (d, 6H, J = 6.8) | 6.33, dd, J = 16.4, 6.0 | 5.36-5.32 m | 4.38-4.35 m | 2.78-2.62 m | 2.04-1.79 m |

TABLE 55

(4R, 6S)-6-[(E)-2-(7-chloro-6-fluoro-4-substituted thiophenylquinoline-3-yl)-ethenyl]-
3,4,5,6-tetrahydro-4-hydroxy-2H-pyran-2-one (A9~12)

| No | R | Formula | [α]_D | Yield* (%) | Mp (° C.) | MS EI⁺ (M + 1) |
|---|---|---|---|---|---|---|
| A9 | H | C₂₂H₁₇ClFNO₃S | +18.3, c = 1, CHCl₃ | 63.0 | 172-4 | 430 |
| A10 | p-F | C₂₂H₁₆ClF₂NO₃S | +25.1, c = 1, CH₂Cl₂ | 75.0 | 192-4 | 448 |
| A11 | m-OCH₃ | C₂₃H₁₉ClFNO₄S | +21.1, c = 1, CH₂Cl₂ | 62.2 | 150-3 | 460 |
| A12 | p-CH(CH₃)₂ | C₂₅H₂₃ClFNO₃S | +16.2, c = 1, CH₂Cl₂ | 63.7 | 175-7 | 472 |

*purified by silica gel chromatography (petroleum ether-EtOAc)

TABLE 56

¹H-NMR data of A9~12 (δ ppm in CDCl₃)

| No | 2"H | 8"H | 5"H | 2'H | —⟨phenyl⟩—R | 1'H | 6H | 4H | 3H | 5H |
|---|---|---|---|---|---|---|---|---|---|---|
| A9 | 9.05 s | 8.19-8.15 m | | 7.35, dd, J = 16.0, 1.2 | 7.22-7.15(m, 3H), 7.05-7.02(m, 2H) | 6.36, dd, J = 16.2, 6.0 | 5.37-5.32 m | 4.37-4.33 m | 2.77-2.61 m | 2.05-1.79 m |
| A10 | 9.03 s | 8.19-8.15 m | | 7.37, dd, J = 16.6, 0.8 | 7.08-7.03(m, 2H), 6.95-6.90(m, 2H) | 6.36, dd, J = 16.2, 5.6 | 5.39-5.35 m | 4.42-4.40 m | 2.79-2.64 m | 2.09-1.80 m |

TABLE 56-continued

¹H-NMR data of A9~12 (δ ppm in CDCl₃)

| No | 2"H | 8"H | 5"H | 2'H | R | 1'H | 6H | 4H | 3H | 5H |
|---|---|---|---|---|---|---|---|---|---|---|
| A11 | 9.04 s | 8.19-8.15 m | | 7.34, dd, J = 16.4, 1.2 | 7.10(t, 1H, J = 8.0), 6.70-6.67(m, 1H), 6.61-6.56(m, 2H), 3.71(s, 3H) | 6.36, dd, J = 16.2, 5.6 | 5.37-5.33 m | 4.37-4.33 m | 2.77-2.61 m | 2.05-1.80 m |
| A12 | 9.02 s | 8.19-8.15 m | | 7.37, d, J = 16.8 | 7.06(d, 2H, J = 8.4), 6.96(d, 2H, J = 8.8) 2.85-2.78(m, 1H), 1.18(d, 6H, J = 7.2) | 6.35, dd, J = 16.4, 6.0 | 5.38-5.33 m | 4.39-4.36 m | 2.72-2.62 m | 2.04-1.78 m |

TABLE 57

(4R,6S)-6-[(E)-2-(6,7,8-trifluoro-4-substitutedthiophenylquinoline-3-yl)-ethenyl]-3,4,5,6-tetrahydro-4-hydroxy-2H-pyran-2-one(A13~16)

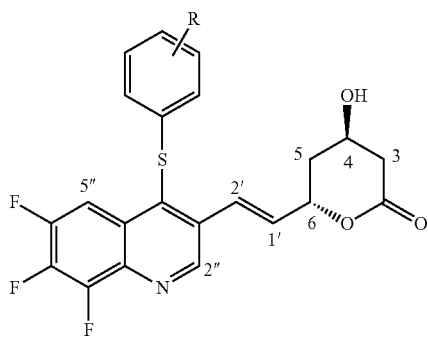

| No | R | Formula | [α]_D | Yield* (%) | Mp (° C.) | MS EI⁺ (M + 1) |
|---|---|---|---|---|---|---|
| A13 | H | C₂₂H₁₆F₃NO₃S | +27.7, c = 1, CH₂Cl₂ | 81.4 | 177-8 | 432 |
| A14 | p-F | C₂₂H₁₅F₄NO₃S | +26.2, c = 1, CH₂Cl₂ | 50.9 | 183-5 | 450 |
| A15 | m-OCH₃ | C₂₃H₁₅F₃NO₄S | +25.5, c = 0.6, CH₂Cl₂ | 54.7 | 168-70 | 462 |
| A16 | p-CH(CH₃)₂ | C₂₅H₂₂F₃NO₃S | +18.7, c = 1, CH₂Cl₂ | 62.0 | 169-71 | 474 |

*: purified by silica gel chromatography (petroleum ether-EtOAc)

TABLE 59

(4R,6S)-6-[(E)-2-(4,7-disubstituted thiophenylquinoline-3-yl)-ethenyl]-3,4,5,6-tetrahydro-4-hydroxy-2H-pyran-2-one(A17~20)

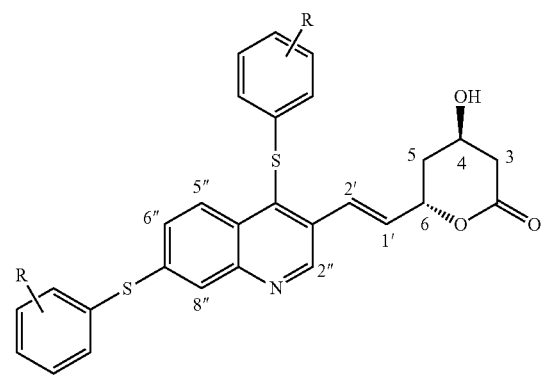

| No | R | Formula | [α]_D | Yield* (%) | Mp (° C.) | MS EI⁺ (M + 1) |
|---|---|---|---|---|---|---|
| A17 | H | C₂₈H₂₃NO₃S₂ | +17.8, c = 0.8, CH₂Cl₂ | 64.6 | 138-40 | 486 |

TABLE 58

¹H-NMR data of A13~16 (δ ppm in CDCl₃)

| No | 2"H | 5"H | 2'H | R | 1'H | 6H | 4H | 3H | 5H |
|---|---|---|---|---|---|---|---|---|---|
| A13 | 9.08 s | 8.08-8.03 m | 7.35, dd, J = 16.4, 1.6 | 7.23-7.14(m, 3H) 7.04-7.02(m, 2H) | 6.36, dd, J = 16.0, 5.6 | 5.37-5.32 m | 4.37-4.35 m | 2.76-2.62 m | 2.05-1.77 m |
| A14 | 9.07 s | 8.08-8.03 m | 7.36, d, J = 16.4 | 7.09-7.05(m, 2H) 6.95-6.91(m, 2H) | 6.36, dd, J = 16.4, 6.0 | 5.40-5.35 m | 4.41 s | 2.79-2.65 m | 2.08-1.79 m |
| A15 | 9.08 s | 8.08-8.03 m | 7.33, dd, J = 16.0, 1.2 | 7.11(t, 1H, J = 8.0) 6.72-6.55(m, 3H), 3.71(s, 3H) | 6.36, dd, J = 16.4, 6.0 | 5.38-5.33 m | 4.37-4.35 m | 2.77-2.62 m | 2.06-1.79 m |
| A16 | 9.08 s | 8.11-8.06 m | 7.37, d, J = 16.4 | 7.09-7.00(m, 4H), 2.86-2.79(m, 1H), 1.22-1.18(m, 6H) | 6.35, dd, J = 16.0, 5.6 | 5.37-5.32 m | 4.39-4.36 m | 2.78-2.62 m | 2.03-2.78 m |

TABLE 59-continued (4R,6S)-6-[(E)-2-(4,7-disubstituted thiophenylquinoline-3-yl)-ethenyl]-3,4,5,6-tetrahydro-4-hydroxy-2H-pyran-2-one(A17~20)

| No | R | Formula | $[\alpha]_D$ | Yield* (%) | Mp (°C.) | MS EI⁺ (M+1) |
|---|---|---|---|---|---|---|
| A18 | p-F | $C_{30}H_{27}NO_5S_2$ | +12.2, c = 0.97, $CH_2Cl_2$ | 75.9 | 140-2 | 522 |
| A19 | m-OCH₃ | $C_{30}H_{27}NO_5S_2$ | +15.9, c = 1, $CH_2Cl_2$ | 52.8 | 48-51 | 546 |
| A20 | p-CH(CH₃)₂ | $C_{34}H_{35}NO_3S_2$ | +7.4, c = 1, $CH_2Cl_2$ | 66.5 | 109-12 | 570 |

*: purified by silica gel chromatography (petroleum ether-EtOAc)

TABLE 61

(4R,6S)-6-[(E)-2-(6-fluoro-4,7-disubstituted thiophenylquinoline-3-yl)-ethenyl]-3,4,5,6-tetrahydro-4-hydroxy-2H-pyran-2-one(A21~24)

| No | R | Formula | $[\alpha]_D$ | Yield* (%) | Mp (°C.) | MS EI⁺ (M+1) |
|---|---|---|---|---|---|---|
| A21 | H | $C_{28}H_{22}FNO_3S_2$ | +8.0, c = 0.8, $CH_2Cl_2$ | 82.2 | 92-4 | 504 |
| A22 | p-F | $C_{28}H_{20}F_3NO_3S_2$ | +2.4, c = 1, $CH_2Cl_2$ | 67.0 | 128-30 | 540 |

TABLE 60

¹H-NMR data of A17~20 (δ ppm in CDCl₃)

| No | 2″H | 5″H | 8″H | 6″H | 2′H (R) | 1′H | 6H | 4H | 3H | 5H |
|---|---|---|---|---|---|---|---|---|---|---|
| A17 | 9.00 s | 8.32, d, J = 8.8 | 7.80 s | 7.55-7.52 m | 7.41-7.31(m, 6H), 7.19-7.01(m, 5H) | 6.29, dd, J = 16.2, 6.4 | 5.33-5.29 m | 4.33-4.31 m | 2.75-2.59 m | 2.01-1.78 m |
| A18 | 9.00 s | 8.31, d, J = 9.2 | 7.69, d, J = 1.6 | | 7.56-7.53(m, 2H), 7.36-7.32(m, 2H), 7.13-7.19(m, 2H), 7.05-7.02(m, 2H), 6.91-6.86(m, 2H) | 6.29, dd, J = 16.2, 6.4 | 5.36-5.32 m | 4.38 s | 2.78-2.62 m | 2.08-1.80 m |
| A19 | 9.01 s | 8.33, d, J = 8.8 | 7.84, d, J = 2.0 | 7.40, dd, J = 8.8, 2.0 | 7.34-7.26(m, 2H), 7.12-7.05(m, 3H), 6.93-6.90(m, 1H), 6.68-6.56(m, 3H), 3.78(s, 3H), 3.69(s, 3H) | 6.30, dd, J = 16.2, 6.0 | 5.35-5.30 m | 4.34-4.32 m | 2.76-2.60 m | 2.03-1.80 m |
| A20 | 9.01 s | 8.37, d, J = 8.8 | 7.78, d, J = 1.6 | 7.40, dd, J = 6.6, 2.0 | 7.51(d, 2H, J = 8.4), 7.35-7.28(m, 3H), 7.08-6.98(m, 4H), 2.99-2.95(m, 1H), 2.85-2.80(m, 1H), 1.31(d, 6H, J = 7.2), 1.20(d, 6H, J = 7.2) | 6.31, dd, J = 16.2, 6.0 | 5.35-5.32 m | 4.37 s | 2.79-2.62 m | 2.03-1.82 m |

TABLE 61-continued (4R,6S)-6-[(E)-2-(6-fluoro-4,7-disubstituted thiophenylquinoline-3-yl)-ethenyl]-3,4,5,6-tetrahydro-4-hydroxy-2H-pyran-2-one(A21~24)

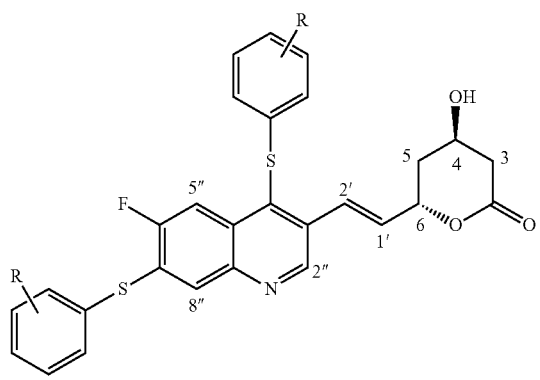

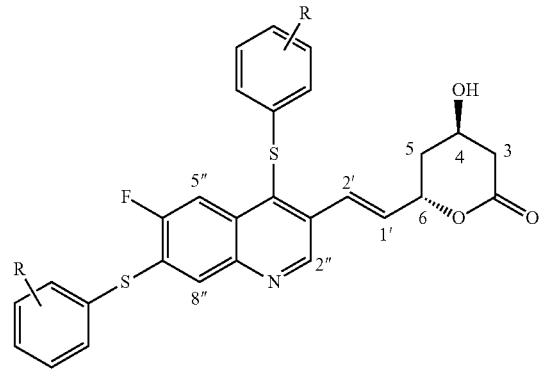

| No | R | Formula | $[\alpha]_D$ | Yield* (%) | Mp (° C.) | MS EI+ (M + 1) |
|---|---|---|---|---|---|---|
| A23 | m-OCH$_3$ | C$_{30}$H$_{26}$FNO$_5$S$_2$ | +6.0, c = 1, CH$_2$Cl$_2$ | 67.9 | 133-4 | 564 |
| A24 | p-CH(CH$_3$)$_2$ | C$_{34}$H$_{34}$FNO$_3$S$_2$ | +2.9, c = 1, CH$_2$Cl$_2$ | 45.8 | 134-6 | 588 |

*: purified by silica gel chromatography (petroleum ether-EtOAc)

TABLE 62

$^1$H-NMR data of A21~24 (δ ppm in CDCl$_3$)

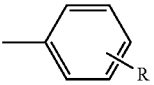

| No | 2"H | 8"H | 5"H | 2'H | R | 1'H | 6H | 4H | 3H | 5H |
|---|---|---|---|---|---|---|---|---|---|---|
| A21 | 8.93 s | 8.06, d, J = 11.2 | | 7.60-7.56(m, 3H), 7.45-7.42(m, 3H), 7.32(dd, 1H, J = 16.8, 1.6), 7.21-7.11(m, 3H), 7.04-7.01(m, 2H) | | 6.30, dd, J = 16.4, 6.0 | 5.34- 5.29 m | 4.33-4.31 m | 2.74-2.59 m | 2.05-1.77 m |
| A22 | 8.92 s | 8.04, d, J = 11.2 | 7.49, d, J = 7.6 | 7.33, dd, J = 16.0, 0.8 | 7.60-7.56(m, 2H), 7.17-7.13(m, 2H) 7.07-7.03(m, 2H), 6.93-6.88(m, 2H) | 6.30, dd, J = 16.0, 5.6 | 5.36-5.32 m | 4.38-4.36 m | 2.77-2.67 m | 2.05-1.79 m |
| A23 | 8.93 s | 8.06, d, J = 11.2 | | 7.36-7.29(m, 2H), 7.16-7.07(m, 3H), 6.98-6.95(m, 1H), 6.69-6.67(m, 1H), 6.60-6.56(m, 2H), 3.80(s, 3H), 3.70(s, 3H) | | 6.30, dd, J = 16.0, 5.6 | 5.34-5.30 m | 4.33-4.31 m | 2.75-2.59 m | 2.02-1.79 m |
| A24 | 8.91 s | 8.06, d J = 11.2 | | 7.55-7.50(m, 3H), 7.36-7.25(m, 3H), 7.07-6.95(m, 4H), 3.00-2.93(m, 1H), 2.85-2.78(m, 1H), 1.30(d, 6H, J = 6.4), 1.18(d, 6H, J = 6.4), | | 6.29, dd, J = 16.4, 6.4 | 5.34- 5.29 m | 4.35-4.33 m | 2.75-2.59 m | 2.03-1.78 m |

TABLE 63

(4R,6S)-6-[(E)-2-(6,8-difluoro-4,7-disubstituted thiophenylquinoline-3-yl)-ethenyl]-3,4,5,6-tetrahydro-4-hydroxy-2H-pyran-2-one(A25~28)

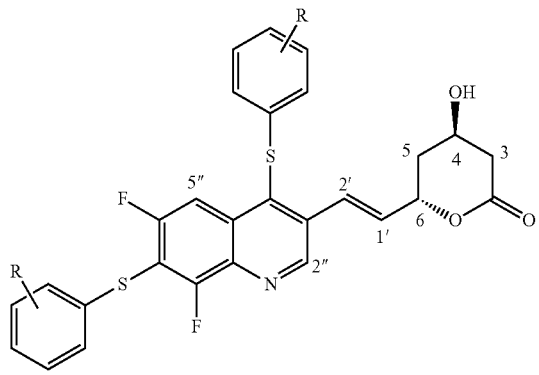

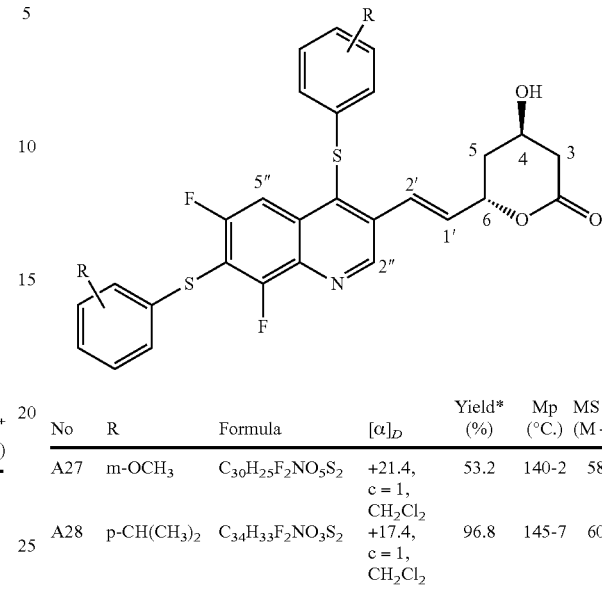

| No | R | Formula | [α]$_D$ | Yield* (%) | Mp (°C.) | MS EI$^+$ (M + 1) |
|---|---|---|---|---|---|---|
| A25 | H | $C_{28}H_{21}F_2NO_3S_2$ | +23.7, c = 1, $CH_2Cl_2$ | 59.8 | 186-8 | 522 |
| A26 | p-F | $C_{28}H_{19}F_4NO_3S_2$ | +20.4, c = 1, $CH_2Cl_2$ | 64.2 | 156-8 | 558 |
| A27 | m-OCH$_3$ | $C_{30}H_{25}F_2NO_5S_2$ | +21.4, c = 1, $CH_2Cl_2$ | 53.2 | 140-2 | 582 |
| A28 | p-CH(CH$_3$)$_2$ | $C_{34}H_{33}F_2NO_3S_2$ | +17.4, c = 1, $CH_2Cl_2$ | 96.8 | 145-7 | 606 |

*: purified by silica gel chromatography (petroleum ether-EtOAc)

TABLE 64

$^1$H-NMR data of A25~28 (δ ppm in CDCl$_3$)

| No | 2″H | 5″H | 2′H | R-C$_6$H$_4$- | 1′H | 6H | 4H | 3H | 5H |
|---|---|---|---|---|---|---|---|---|---|
| A25 | 9.06 s | 7.98, dd J = 10.0, 1.2 | | 7.39-7.32(m, 3H), 7.28-7.14(m, 6H), 7.06-7.04(m, 2H) | 6.38, dd, J = 16.0, 5.6 | 5.37-5.32 m | 4.36-4.34 m | 2.76-2.61 m | 2.06-1.76 m |
| A26 | 9.04 s | 7.95, dd J=10.0, 2.0 | 7.35, dd, J = 16.4, 1.2 | 7.47-7.44(m, 2H), 7.09-7.05(m, 2H), 7.00-6.90(m, 4H) | 7.37, dd, J = 16.4, 5.6 | 5.39-5.34 m | 4.40-4.39 m | 2.78-2.64 m | 2.08-1.78 m |
| A27 | 9.06 s | 7.97, dd J = 10.0, 0.8 | 7.33, d, J = 16.0 | 7.18-7.08(m, 2H), 6.93-6.90(m, 2H), 6.77-6.57(m, 4H), 3.74(s, 3H), 3.68(s, 3H) | 6.38, dd, J = 16.4, 5.6 | 5.37-5.34 m | 4.36-4.34 m | 2.76-2.61 m | 2.04-1.77 m |
| A28 | 9.04 s | 7.99, dd J = 10.4, 1.2 | | 7.38-7.34(m, 3H), 7.13-7.06(m, 4H) 6.99-6.97(m, 2H), 2.87-2.80(m, 2H), 1.21-1.17(m, 6H) | 6.36, dd, J = 16.4, 6.0 | 5.35-5.32 m | 4.36-4.35 m | 2.77-2.61 m | 2.02-1.78 m |

TABLE 65

(4R,6S)-6-[(E)-2-(4,6,7-trisubstituted thiophenylquinoline-3-yl)-ethenyl]-3,4,5,6-tetrahydro-4-hydroxy-2H-pyran-2-one(A29~32)

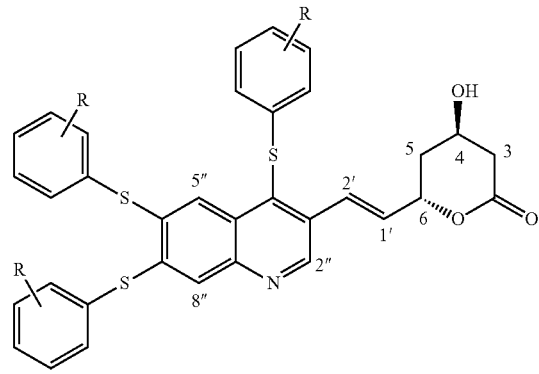

| No | R | Formula | $[\alpha]_D$ | Yield* (%) | Mp (° C.) | MS EI+ (M+1) |
|---|---|---|---|---|---|---|
| A29 | H | $C_{34}H_{27}NO_3S_3$ | +19.7, c = 1, $CH_2Cl_2$ | 81.5 | 190-2 | 594 |
| A30 | p-F | $C_{34}H_{24}F_3NO_3S_3$ | +18.0, c = 1, $CH_2Cl_2$ | 84.2 | 180-1 | 648 |
| A31 | m-OCH$_3$ | $C_{37}H_{33}NO_6S_3$ | +21.4, c = 1, $CH_2Cl_2$ | 67.7 | 57-59 | 684 |
| A32 | p-CH(CH$_3$)$_2$ | $C_{43}H_{45}NO_3S_3$ | +21.4, c = 0.73, $CH_2Cl_2$ | 50.3 | 182-4 | 720 |

*: purified by silica gel chromatography (petroleum ether-EtOAc)

TABLE 67

(4R,6S)-6-[(E)-2-(6-fluoro-4,7,8-trisubstituted thiophenylquinoline-3-yl)-ethenyl]-3,4,5,6-tetrahydro-4-hydroxy-2H-pyran-2-one(A33~36)

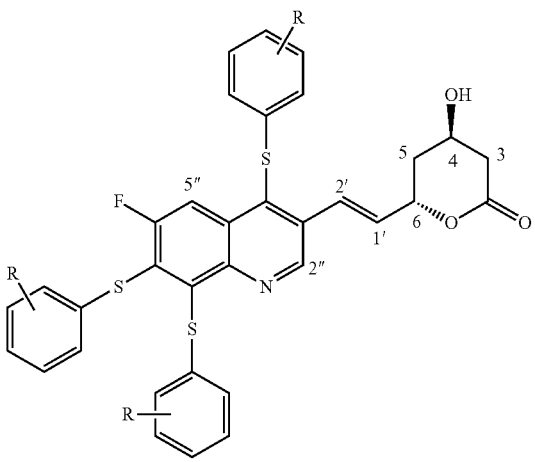

| No | R | Formula | $[\alpha]_D$ | Yield* (%) | Mp (° C.) | MS EI+ (M+1) |
|---|---|---|---|---|---|---|
| A33 | H | $C_{34}H_{26}FNO_3S_3$ | +15.4, c = 0.9, $CH_2Cl_2$ | 65.7 | 138-9 | 612 |
| A34 | p-F | $C_{34}H_{23}F_4NO_3S_3$ | +14.3, c = 1, $CH_2Cl_2$ | 52.4 | 194-6 | 665 |

TABLE 66

$^1$H-NMR data of A29~32 (δ ppm in CDCl$_3$)

| No | 2″H | 8″H | 5″H | 2′H | R (phenyl) | 1′H | 6H | 4H | 3H | 5H |
|---|---|---|---|---|---|---|---|---|---|---|
| A29 | 8.91 s | 8.12 s | 7.57 s | 7.55-7.53(m, 2H), 7.43-7.40(m, 3H) 7.35-7.27(m, 6H), 7.14-7.10(m, 3H), 6.85-6.83(m, 2H) | | 6.29, dd, J = 16.0, 6.0 | 5.32 m | 4.34-4.33 m | 2.75-2.63 m | 2.03-1.80 m |
| A30 | 8.91 s | 7.96 s | 7.50 s | 7.57-5.73(m, 2H), 7.38-7.33(m, 3H), 7.16-7.12(m, 2H), 7.05-7.00(m, 2H), 6.87-6.80(m, 4H) | | 6.29, dd, J = 16.0, 6.0 | 5.38-5.33 m | 4.41-4.39 m | 2.79-2.62 m | 2.09-1.84 m |
| A31 | 8.91 s | 8.19 s | 7.61 s | 7.34-7.28(m, 2H), 7.21-6.83(m, 8H), 6.64-6.61(m, 1H), 6.46-6.38(m, 2H), 3.79(s, 3H), 3.73(s, 3H), 3.67(s, 3H) | | 6.28, dd, J = 16.0, 6.0 | 5.33-5.29 m | 4.33-4.31 m | 2.75-2.58 m | 2.03-1.80 m |
| A32 | 8.88 s | 8.04 s | | 7.54-7.49(m, 3H), 7.37-7.26(m, 5H), 7.20(d, 2H, J = 8.0), 6.79(d, 2H, J = 8.0), 6.75(d, 2H, J = 8.4), 2.98-2.91(m, 2H), 2.84-2.81(m, 1H), 1.31-1.26(m, 12H), 1.20(d, 6H, J = 7.2) | | 6.27, dd, J = 16.4, 6.0 | 5.34-5.29 m | 4.36-4.34 m | 2.76-2.59 m | 2.04-1.82 m |

TABLE 67-continued (4R,6S)-6-[(E)-2-(6-fluoro-4,7,8-trisubstituted thiophenylquinoline-3-yl)-ethenyl]-3,4,5,6-tetrahydro-4-hydroxy-2H-pyran-2-one(A33~36)

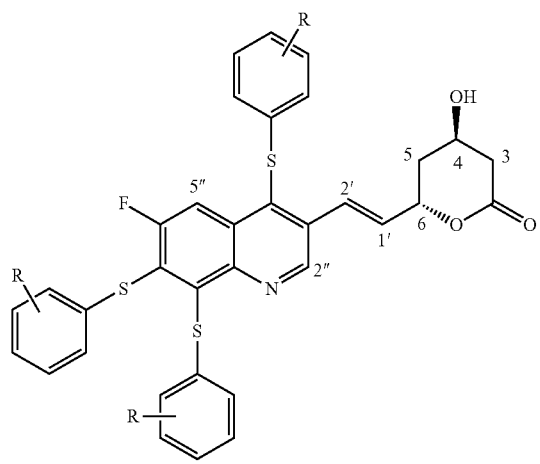

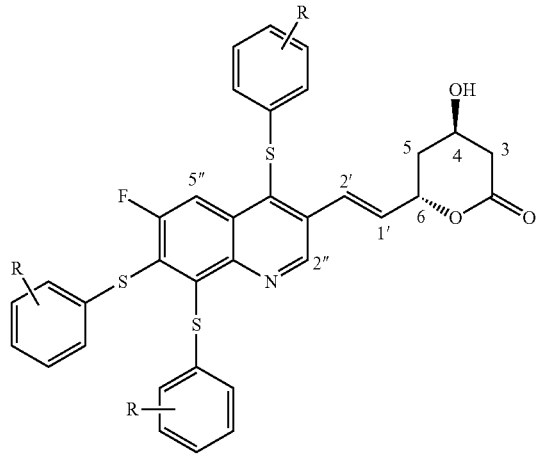

| No | R | Formula | $[\alpha]_D$ | Yield* (%) | Mp (° C.) | MS EI+ (M + 1) |
|---|---|---|---|---|---|---|
| A35 | m-OCH$_3$ | C$_{37}$H$_{32}$FNO$_6$S$_3$ | +17.9, c = 0.94, CH$_2$Cl$_2$ | 41.4 | oil | 702 |
| A36 | p-CH(CH$_3$)$_2$ | C$_{43}$H$_{44}$FNO$_3$S$_3$ | +16.6, c = 1, CH$_2$Cl$_2$ | 69.1 | 156-8 | 738 |

*: purified by silica gel chromatography (petroleum ether-EtOAc)

TABLE 68

$^1$H-NMR data of A33~36 (δ ppm in CDCl$_3$)

| No | 2″H | 5″H | 2′H | (phenyl-R) | 1′H | 6H | 4H | 3H | 5H |
|---|---|---|---|---|---|---|---|---|---|
| A33 | 9.10 s | 8.19, d, J = 10.8 | 7.32, dd, J = 16.2, 1.2 | 7.22-7.04(m, 15H) | 6.33, dd, J = 16.4, 5.6 | 5.34-5.29 m | 4.34-4.30 m | 2.74-2.59 m | 2.04-1.74 m |
| A34 | 9.11 s | 8.20, d, J = 10.4 | 7.32, dd, J = 16.4, 1.2 | 7.13-7.05(m, 3H), 6.81-6.58(m, 9H), 3.71-3.69(m, 9H) | 6.34, dd, J= 16.0, 6.0 | 5.34-5.29 m | 4.34-4.32 m | 2.76-2.60 m | 2.02-1.77 m |
| A35 | 9.09 s | 8.16, d, J = 10.4 | 7.33, dd, J = 16.0, 1.2 | 7.27-7.20(m, 4H), 7.09-7.06(m, 2H), 6.95-6.87(m, 6H) | 7.34, dd, J = 16.4, 5.6 | 5.37-5.32 m | 4.39-4.38 m | 2.78-2.63 m | 2.06-1.77 m |
| A36 | 9.11 s | 8.17, d, J = 10.8 | 7.34, d, J = 16.4 | 7.14(t, 4H, J = 8.4), 7.08-7.02(m, 6H), 6.98(d, 2H, J = 8.0) 2.85-2.80(m, 3H), 1.20-1.18(m, 18H) | 6.33, dd, J = 16.0, 5.6 | 5.35-5.32 m | 4.35-4.33 m | 2.80-2.64 m | 1.99-1.79 m |

TABLE 69

(4R,6S)-6-[(E)-2-(4,6,7,8-tetrasubstituted thiophenylquinoline-3-yl)-ethenyl]-3,4,5,6-tetrahydro-4-hydroxy-2H-pyran-2-one(A37~40)

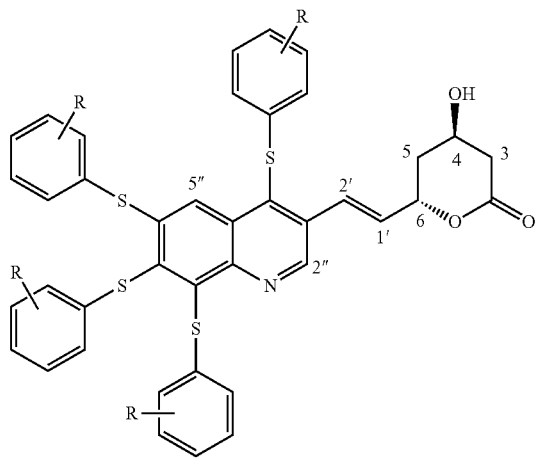

| No | R | Formula | $[\alpha]_D$ | Yield* (%) | Mp (° C.) | MS EI+ (M + 1) |
|---|---|---|---|---|---|---|
| A37 | H | $C_{40}H_{31}NO_3S_4$ | +31.1, c = 0.92, THF | 69.6 | 200-3 | 702 |
| A38 | p-F | $C_{40}H_{27}F_4NO_3S_4$ | +25.5, c = 1, THF | 75.5 | 218-20 | 774 |
| A39 | m-OCH$_3$ | $C_{44}H_{39}NO_7S_4$ | +28.2, c = 1, CH$_2$Cl$_2$ | 80.0 | oil | 822 |
| A40 | p-CH(CH$_3$)$_2$ | $C_{52}H_{55}NO_3S_4$ | +21.9, c = 1, acetone | 81.5 | 162-4 | 870 |

*: purified by silica gel chromatography (petroleum ether-EtOAc)

TABLE 71

In vitro inhibition on HMG CoA reductase of some quinoline compounds A ($IC_{50}$)

| No | $IC_{50}$(Mm) |
|---|---|
| rosuvastatin | 9.03 |
| atorvastatin | 13.22 |
| Fluvastatin | 21.21 |
| A16 | 3.21 |
| A23 | 3.64 |
| A40 | 4.35 |
| A21 | 4.41 |
| A14 | 7.93 |
| A11 | 9.24 |
| A24 | 10.60 |
| A13 | 10.67 |
| A34 | 11.94 |
| A4 | 12.65 |
| A32 | 14.15 |
| A31 | 15.37 |
| A20 | 15.75 |
| A2 | 18.56 |
| A12 | 22.05 |
| A29 | 32.55 |
| A22 | 38.93 |
| A27 | 49.67 |
| A35 | 74.55 |

TABLE 70

$^1$H-NMR data of A37~40 (δ ppm in CDCl$_3$)

| No | 2″H | 5″H | 2′H | 1′H | 6H | 4H | 3H | 5H |
|---|---|---|---|---|---|---|---|---|
| A37 | 8.98 s | 7.87 s | 7.43-7.25(m, 6H), 7.19-7.04(m, 13H), 6.74-6.72(m, 2H) | 6.30, dd, J = 16.4, 6.0 | 5.33-5.29 m | 4.35-4.34 m | 2.75-2.59 m | 2.03-1.79 m |
| A38 | 9.17 s | 7.73 s | 7.51-7.48(m, 2H), 7.33-7.27(m, 2H), 7.23-7.17(m, 3H), 7.14-6.97(m, 8H), 6.84-6.75(m, 3H) | | 5.31-5.23 m | 5.14 s | 2.71-2.42 m | 1.94-1.75 m |
| A39 | 9.00 s | 7.95 s | 7.32(dd, J = 16.4, 1.2) | 7.26-7.22(m, 2H), 7.11-6.94(m, 6H), 6.74-6.57(m, 6H), 6.34-6.27(m, 3H), 3.72-3.66(m, 12H) | 5.32 s | 4.35-4.33 m | 2.75-2.63 m | 2.03-1.83 m |
| A40 | 8.97 s | 7.84 s | 7.37-7.31(m, 3H), 7.22(d, 2H, J = 8.0), 7.13(d, 2H, J = 7.2), 7.06-6.95(m, 8H), 6.66(d, 2H, J = 8.0), 2.97-2.94(m, 1H), 2.85-2.77(m, 3H), 1.29-1.16(m, 24H) | 6.29, dd, J = 16.0, 5.6 | 5.31 s | 4.35 s | 2.75-2.59 m | 2.02-1.79 m |

What is claimed is:
1. A quinoline compound of formula A or a stereoisomer thereof,

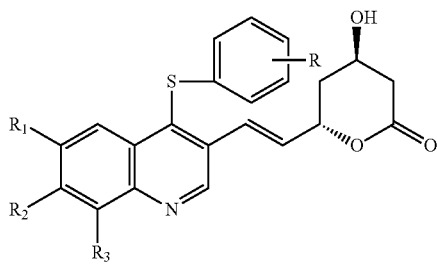

Wherein
$R_1$, $R_2$ and $R_3$ are independently selected from the groups consisting of hydrogen, halogen, the group shown in formula H,

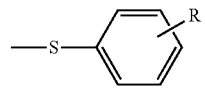

Wherein
R is selected from the group consisting of hydrogen, halogen, C1~4 alkyl or C1~4 alkoxy.
2. The compound according to claim 1, wherein halogen is F or Cl.
3. The compound according to claim 1, wherein R is methyl, ethyl, propyl, isopropyl, cyclopropyl, methoxy, ethoxy, propoxy, or isopropoxy.
4. The quinoline compound or stereoisomer according to claim 1, selected from:
(4R,6S)-6-[(E)-2-(6,7,8-trifluoro-4-(4-isopropylthiophenyl)quinoline-3-yl)-ethenyl]-3,4,5,6-tetrahydro-4-hydroxy-2H-pyran-2-one;
(4R,6S)-6-[(E)-2-(6-fluoro-4,7-di-(3-methoxythiophenyl)quinoline-3-yl)-ethenyl]-3,4,5,6-tetrahydro-4-hydroxy-2H-pyran-2-one;
(4R,6S)-6-[(E)-2-(4,6,7,8-tetra-(3-methoxythiophenyl)quinoline-3-yl)-ethenyl]-3,4,5,6-tetrahydro-4-hydroxy-2H-pyran-2-one;
(4R,6S)-6-[(E)-2-(6-fluoro-4,7-di-(thiophenyl)quinoline-3-yl)-ethenyl]-3,4,5,6-tetrahydro-4-hydroxy-2H-pyran-2-one;
(4R,6S)-6-[(E)-2-(6,7,8-trifluoro-4-(4-fluorothiophenyl)quinoline-3-yl)-ethenyl]-3,4,5,6-tetrahydro-4-hydroxy-2H-pyran-2-one;
(4R,6S)-6-[(E)-2-(7-chloro-6-fluoro-4-(3-methoxythiophenyl)quinoline-3-yl)-ethenyl]-3,4,5,6-tetrahydro-4-hydroxy-2H-pyran-2-one;
(4R,6S)-6-[(E)-2-(6-fluoro-4,7-di-(4-isopropylthiophenyl)quinoline-3-yl)-ethenyl]-3,4,5,6-tetrahydro-4-hydroxy-2H-pyran-2-one;
(4R,6S)-6-[(E)-2-(6,7,8-trifluoro-4-thiophenylquinoline-3-yl)-ethenyl]-3,4,5,6-tetrahydro-4-hydroxy-2H-pyran-2-one;
(4R,6S)-6-[(E)-2-(6-fluoro-4,7,8-tri-(4-fluorothiophenyl)quinoline-3-yl)-ethenyl]-3,4,5,6-tetrahydro-4-hydroxy-2H-pyran-2-one;
or (4R,6S)-6-[(E)-2-(4-(4-isopropylthiophenyl)quinoline-3-yl)-ethenyl]-3,4,5,6-tetrahydro-4-hydroxy-2H-pyran-2-one.
5. A method of preparation of the quinoline compound or stereoisomer according to claim 1, wherein compound D reacts under acid condition.
6. The method of the preparation according to claim 5, wherein the acid is $CF_3COOH$, $CH_3COOH$ or HCl.
7. The method of the preparation according to claim 5, wherein the volume percentage of acid in solvent is 5-40%.
8. The method of the preparation according to claim 7, wherein the volume percentage of acid in solvent is 20%.
9. The method according to claim 5, wherein the temperature is 0° C.~80° C.
10. The method according to claim 9, wherein the temperature is 25° C.
11. The method according to claim 5, wherein the reaction time is between 1~8 hours.
12. The method according to claim 5, wherein the solvent is selected from one or more of the following: THF, t-BuOMe, $CH_2Cl_2$, $CHCl_3$, and toluene.
13. A method of inhibiting HMG CA reductase or treating diseases resulting from hyperlipemia, which comprise administering an effective amount of the compound or stereoisomer according to claim 1.

* * * * *